United States Patent [19]
Caron et al.

[11] Patent Number: 6,041,020
[45] Date of Patent: Mar. 21, 2000

[54] GAS-COUPLED LASER ACOUSTIC DETECTION

[75] Inventors: James N. Caron; James B. Mehl; Karl V. Steiner, all of Newark, Del.

[73] Assignee: University of Delaware, Newark, Del.

[21] Appl. No.: 08/840,968

[22] Filed: Apr. 21, 1997

[51] Int. Cl.[7] .................................................. H04R 14/00
[52] U.S. Cl. ........................ 367/149; 356/340; 356/341; 73/653
[58] Field of Search ............................ 367/149; 356/340, 356/341; 73/653

[56] References Cited

U.S. PATENT DOCUMENTS

| | | | |
|---|---|---|---|
| 3,528,743 | 9/1970 | Scott et al. | 73/653 |
| 3,709,599 | 1/1973 | Iten | 356/28 |
| 3,745,350 | 7/1973 | Hill et al. | 250/218 |
| 5,280,272 | 1/1994 | Nagashima et al. | 340/630 |
| 5,504,719 | 4/1996 | Jacobs | 367/149 |
| 5,566,135 | 10/1996 | MacLeod | 367/149 |

*Primary Examiner*—J. Woodrow Eldred
*Attorney, Agent, or Firm*—Connolly & Hutz

[57] ABSTRACT

The investigation, development and application of a laser-based ultrasonic inspection system to the problems of evaluating polymer/graphite composite materials has been realized. The use of lasers to generate and detect ultrasonic waveforms in materials provides a means to detect material properties remotely. The study consisted of three main aspects: 1) A confocal Fabry-Perot (CFP) based system has been devolved which uses light reflected from the CFP interferometer to derive the ultrasonic signal. This allows higher frequency components of the detected waveforms to be discerned when compared to a CFP-based system using light transmitted through the CFP interferometer. 2) Thermoelastic and ablative laser generation of acoustic pulses in polymer/graphite composite materials has been investigated. Thermoelastic generation of ultrasound occurs when thermal energy deposited by a pulsed laser creates a localized expansion in the material. Ablative generation of ultrasound results from the creation of a plasma above the surface when the laser pulse surpasses an intensity threshold. 3) A novel technique, designated Gas-Coupled Laser Acoustic Detection (GCLAD), has been realized, in which the ultrasonic wave is detected optically after it has been transmitted from sample to air. This technique has the advantage of being independent of surface reflectivity and optical smoothness, and has comparable sensitivity to the CFP-based system.

13 Claims, 72 Drawing Sheets

//6,041,020//

GAS-COUPLED LASER ACOUSTIC DETECTION

The U.S. Government has a paid-up license in this invention and may have the right in limited circumstances to require the patent owner to license others on reasonable terms as provided for by the terms of grant No. DAAL03-92-G-0114 awarded by the Army Research Office/ University Research Initiative.

The original premise of this project was to examine the prospect of using a laser-based ultrasonic inspection system for evaluation of polymer/graphite composite materials. The generality has been narrowed for this study by concentrating on three aspects: the development of a confocal Fabry-Perot based detection system which derives the ultrasonic signal from light reflected from, as opposed to transmitted through, the CFP interferometer; investigation of the effects and consequences of thermoelastic and ablative generation on polymer/graphite composite materials; and the detection of acoustic waves in air, after transmission through a material, by a laser beam deflection technique. The laser beam deflection technique, designated Gas-coupled Laser Acoustic Detection (GCLAD), was discovered during the course of the project and offers an alternative to interferometric detection. Although these topics were investigated with polymer/ graphite composites in mind, much of this work also applies to the larger field of laser ultrasonics.

-continued

BRIEF DESCRIPTION OF THE DRAWINGS

Figure 32:
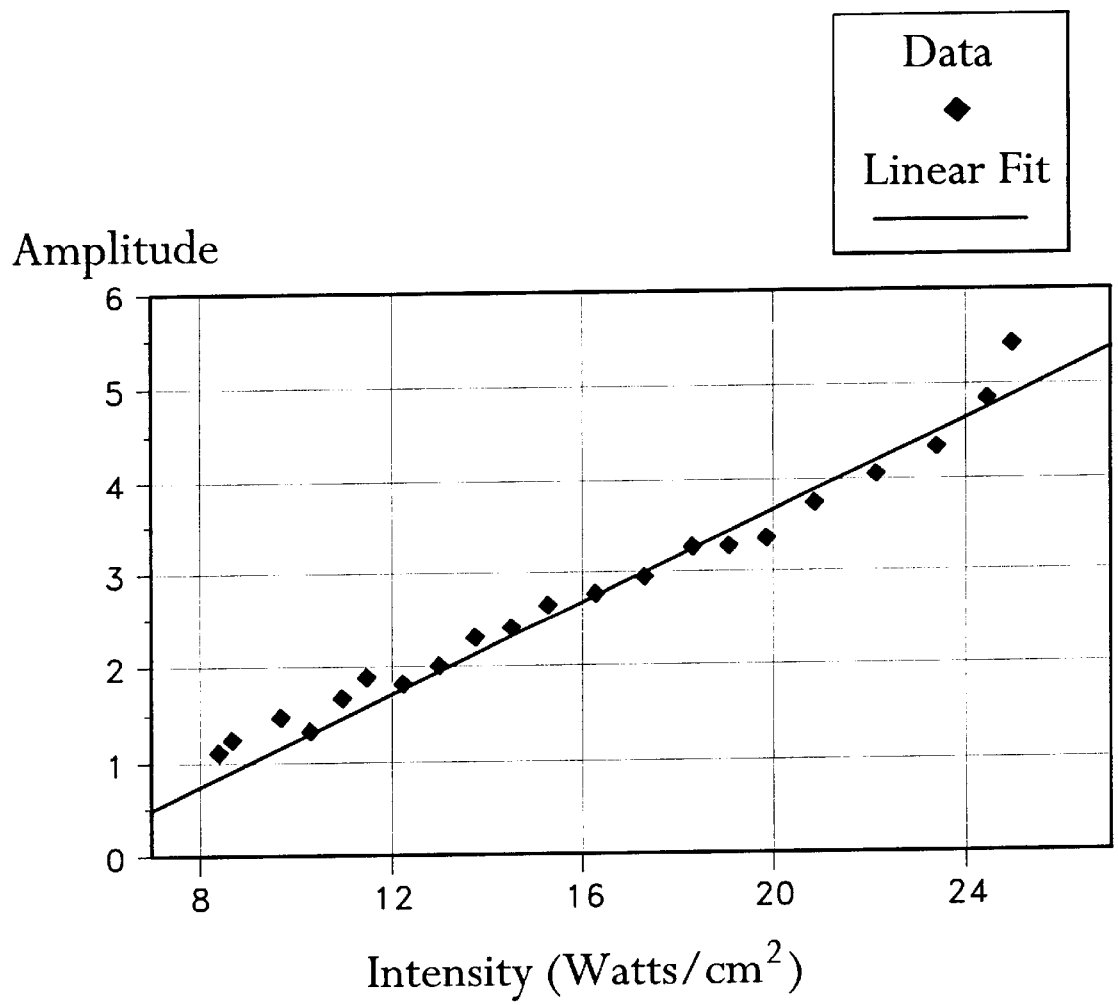

FIG. 32 Graph showing the dependence of the ablation detector with a narrow field of view on the source laser intensity. The linear fir reveals a threshold above 5 W/cm$^2$ with an R$^2$ value of 0.971.

Figure 33:
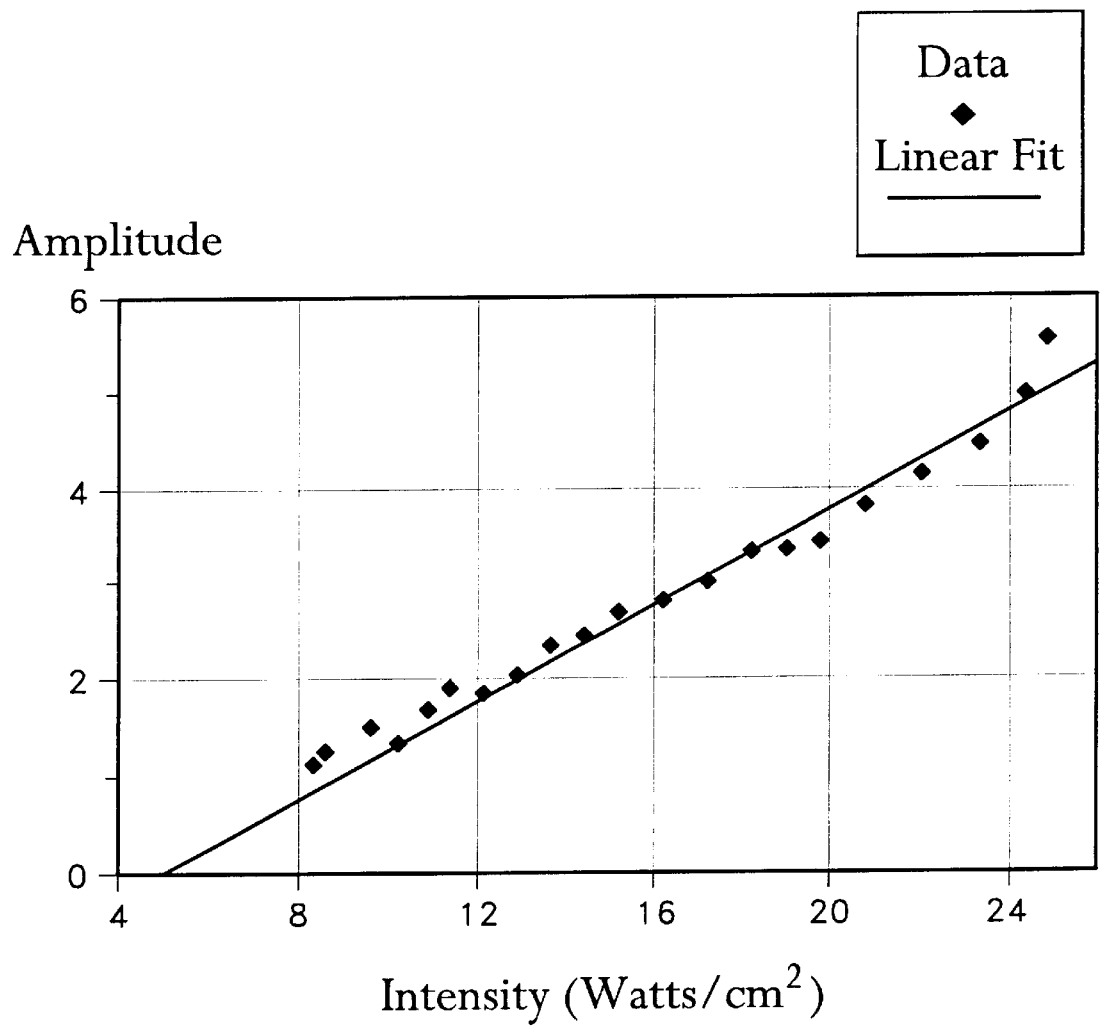

FIG. 33 Graph showing plume signal amplitudes with the ablation detector placed in line with the cylindrical axis of the ablation plume. The linear fit shows a threshold above 5 W/cm$^2$ with R$^2$ = 0.994.

Figure 34:
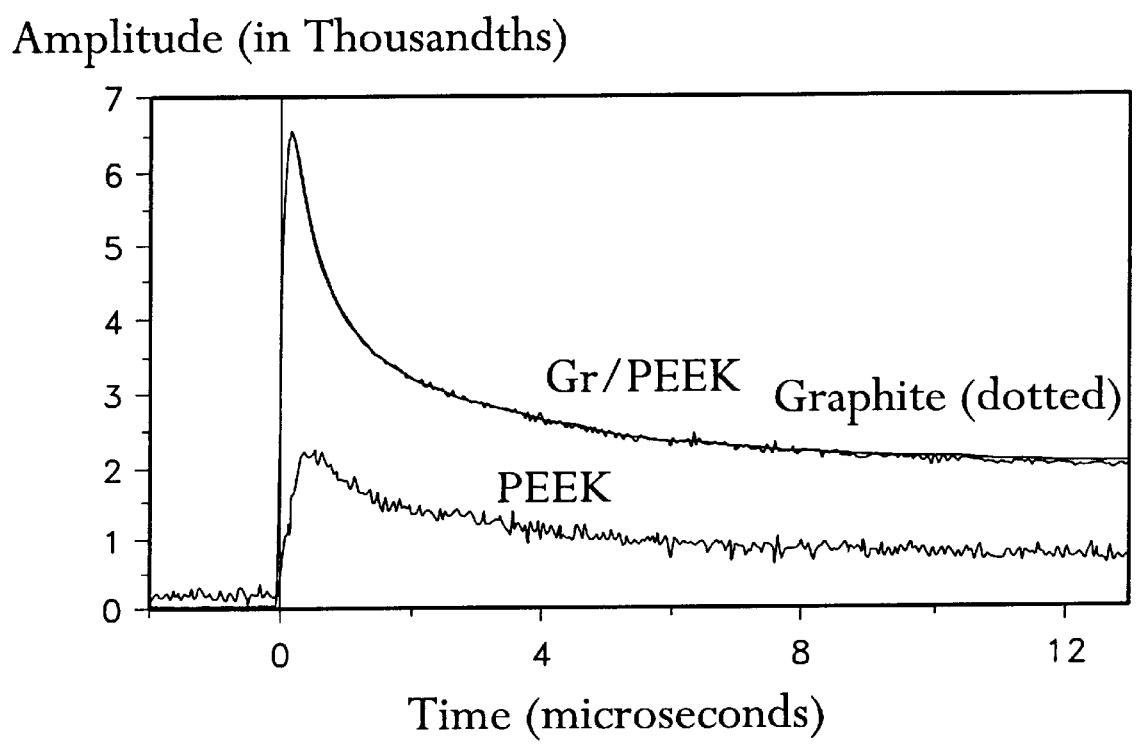

FIG. 34 Graph showing a comparison of the ablation plumes of pure PEEK, pure graphite, and a graphite/PEEK polymer. The resemblance of the graphite and the composite signals indicate that the ablation plume is mostly a result of the ablation of the graphite fibers in the composite. (Gr/PEEK data was multiplied by a scale factor to fit graphite data).

Figure 35:
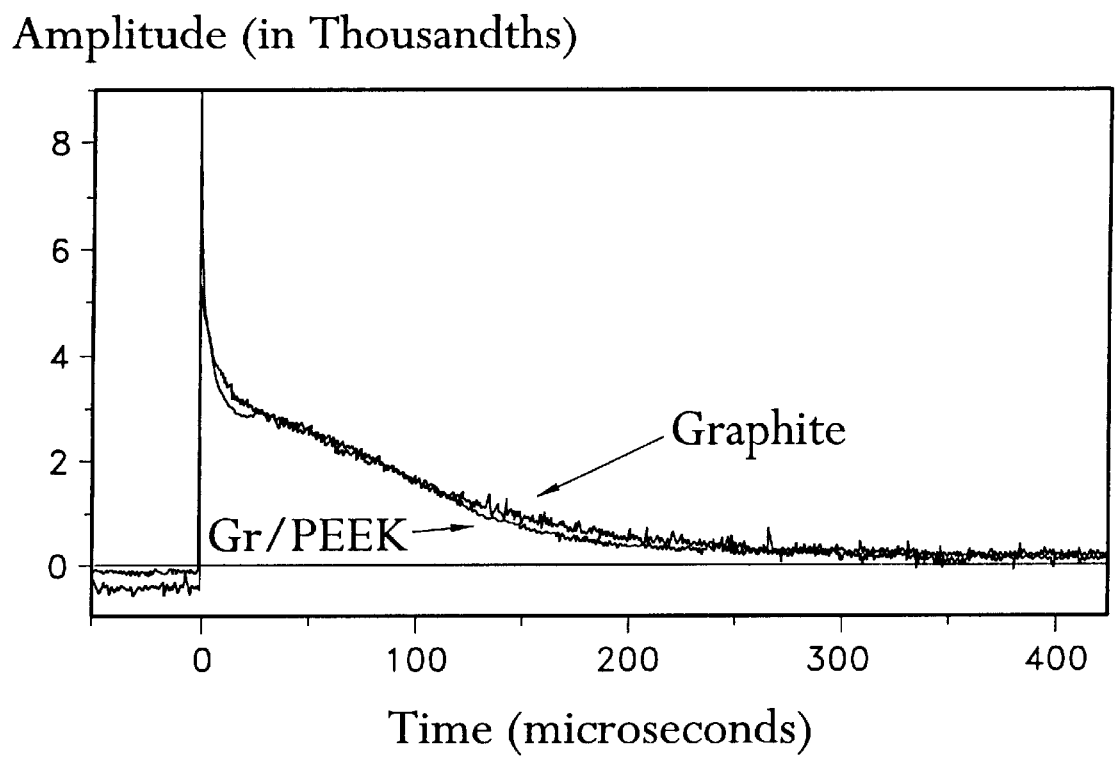

FIG. 35 Graph showing pure graphite and composite ablation plume signals on a longer time scale. The signal persists past 300 μs.

Figure 36:

FIG. 36 Micrograph of a virgin surface on 2.9 mm graphite/PEEK composite.

Figure 37:
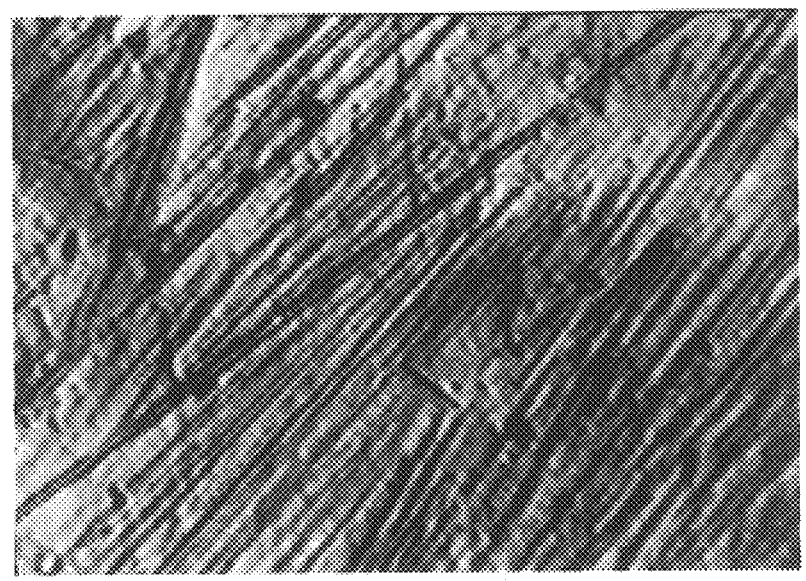

FIG. 37 Micrograph of a surface after being struck by 20 pulses in the moderate thermoelastic regime on 8.9 mm graphite/PEEK composite. Slight polymer melting is observed.

Figure 38:
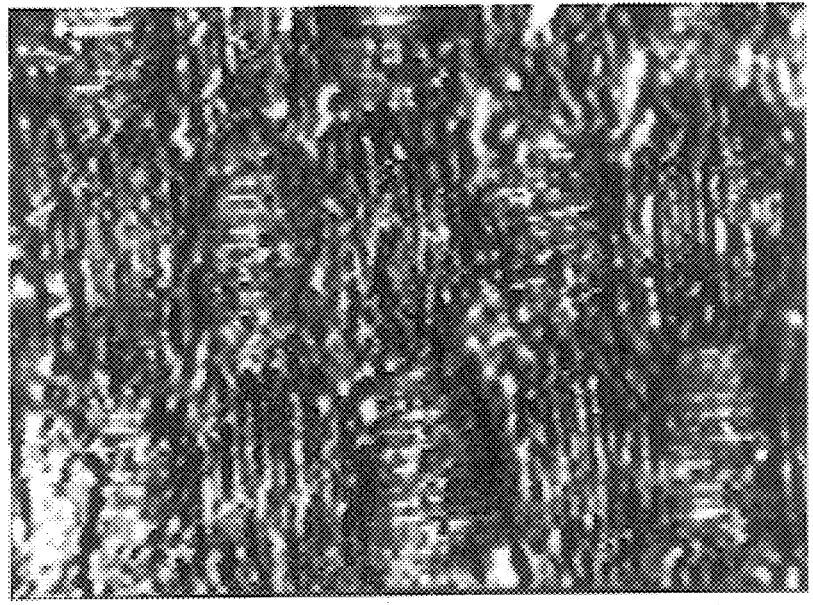

FIG. 38 Micrograph of a virgin surface on 8.9 mm graphite/epoxy composite.

Figure 39:

FIG. 39 Micrograph of a surface after being struck by 20 pulses in the moderate thermoelastic regime. Increased amounts of epoxy result from the melting of the epoxy and the thermal expansion of the fibers.

Figure 40:
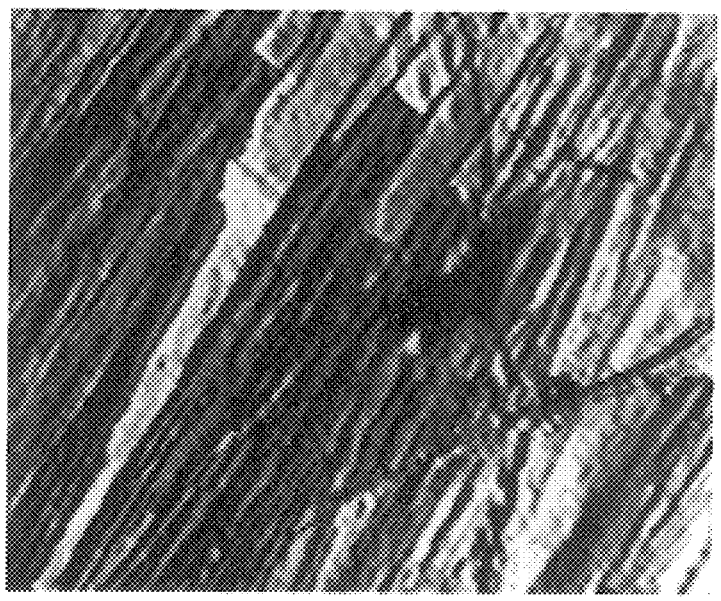

FIG. 40 Micrograph of the laser damage created by one shot in the ablation regime on 2.9 mm graphite/PEEK composite. The jagged edges of polymer indicate that ablation in the graphite fibers shatter the thin polymer surface.

Figure 41:
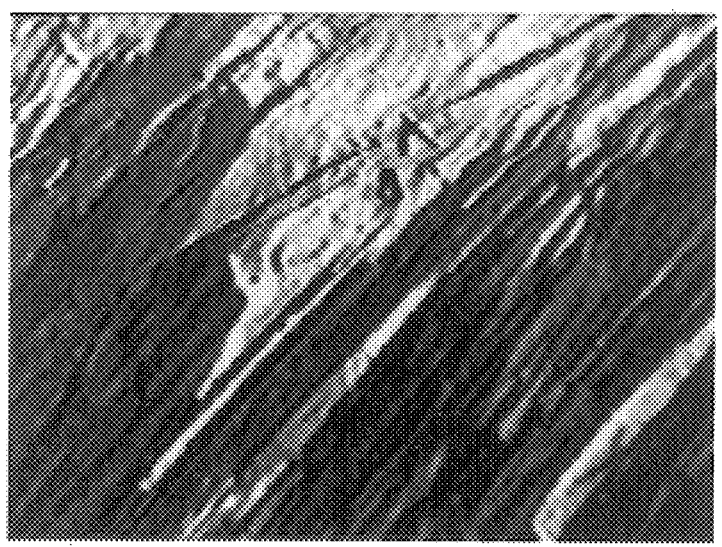

FIG. 41 Micrograph of the laser damage created by 20 shots in the ablation regime on 2.9 mm graphite/PEEK composite. The jagged edges of polymer indicate that ablation in the graphite fibers shatter the thin polymer surface.

Figure 42:
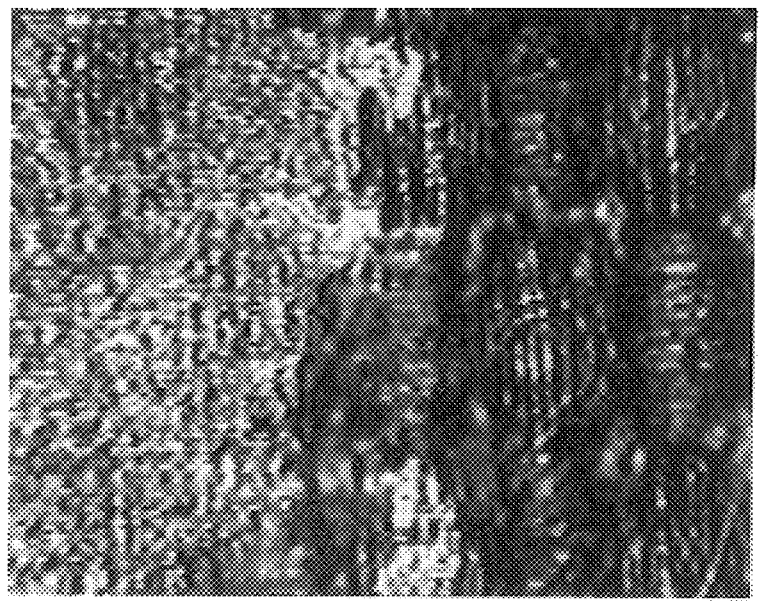

FIG. 42 Micrograph of the laser damage created by one shot in the ablation regime on 8.9 mm graphite/epoxy composite. The top woven fibers are ablated with one shot.

Figure 43:

FIG. 43 Micrograph of the laser damage created by 20 shots in the ablation regime on 8.9 mm graphite/epoxy composite. The top woven fibers are ablated with one shot.

Figure 44:
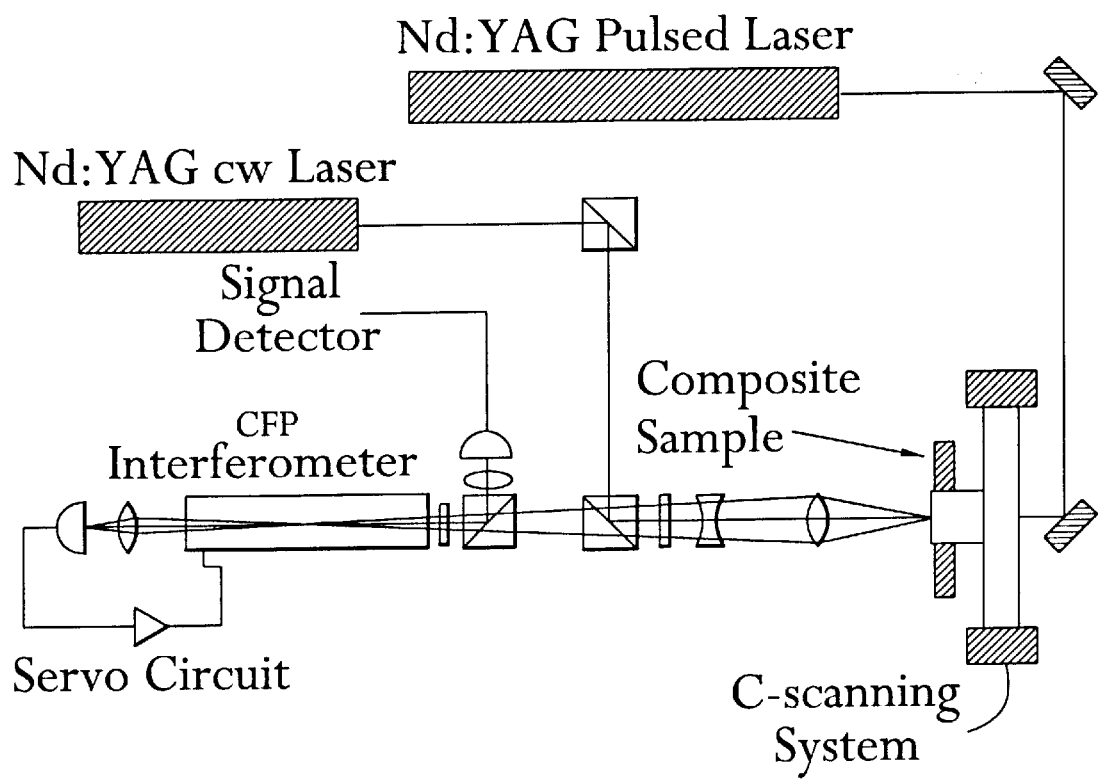

FIG. 44 Diagram of the laser ultrasonic C-scanning system. Two screw-driven arms move the sample in two directions in front of the stationary laser beams. A Macintosh computer controls the positioning and data acquisition.

Figure 45:
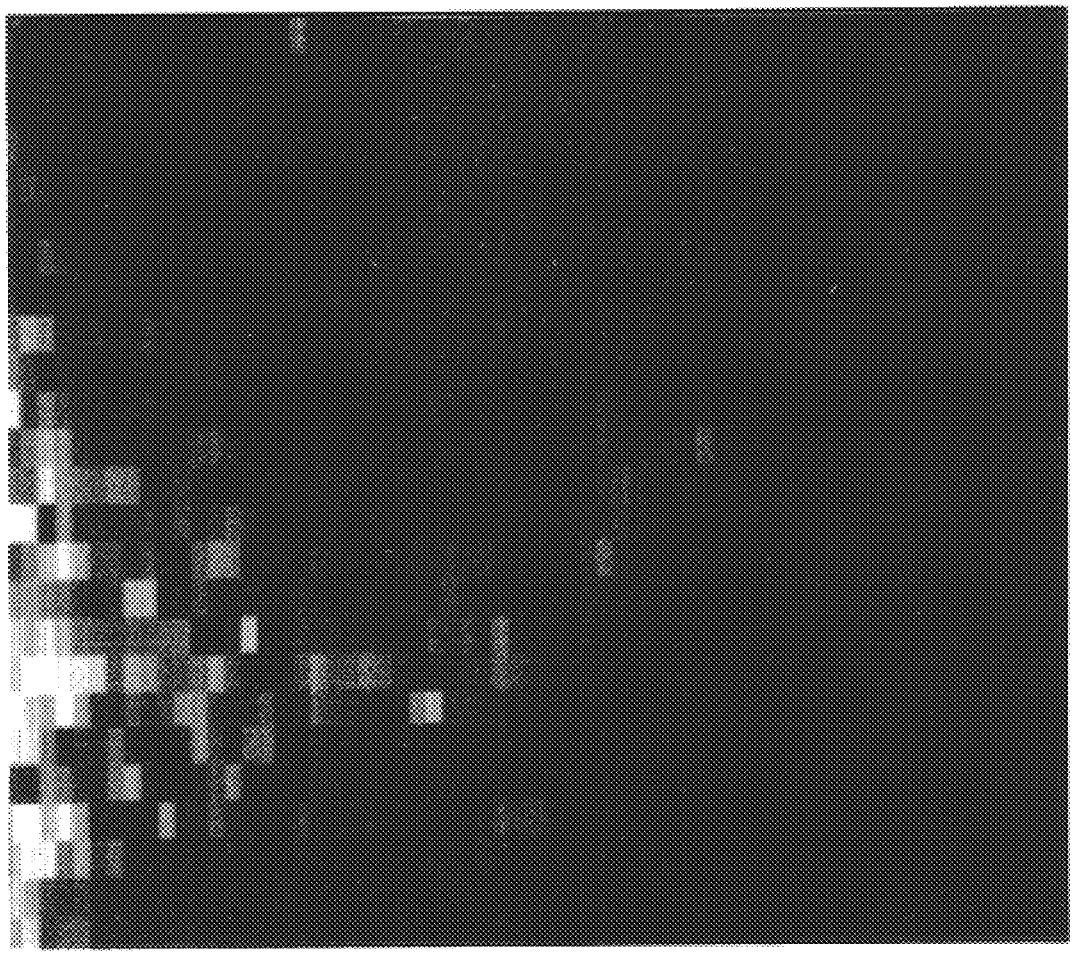

FIG. 45 Laser ultrasonic C-scan of an 8.9 mm thick quasi-isotropic graphite/epoxy composite. The sample was embedded with an artificial Teflon flaw possessing the surface are similar to that of a quarter. Lighter areas show good reception of the longitudinal waves.

Figure 46:
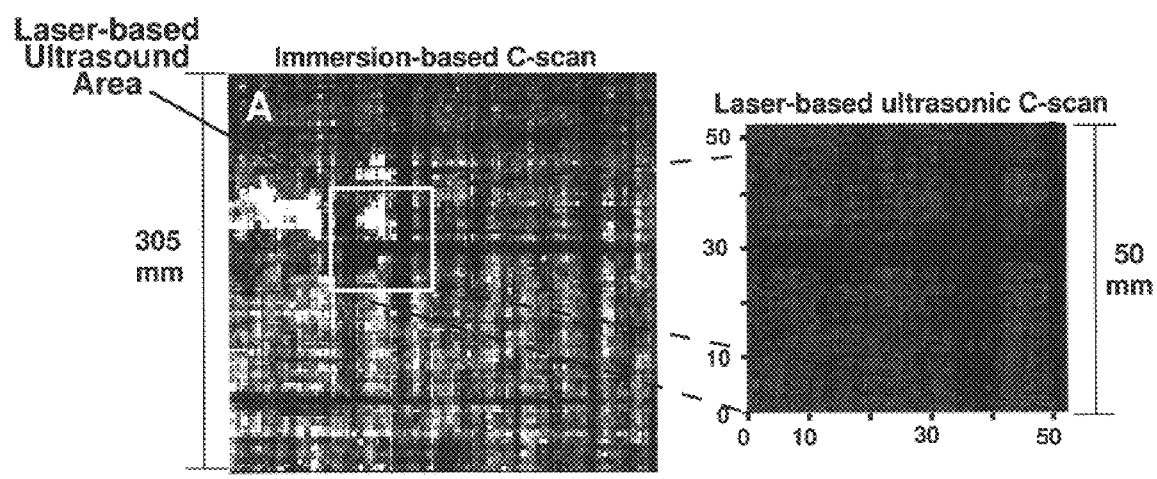

FIG. 46 Laser ultrasonic C-scan of a tow-placed panel (AS-4/PEKK, [0/90]$_{2S}$) alongside an immersion-based C-scan of the same panel.

Figure 47:
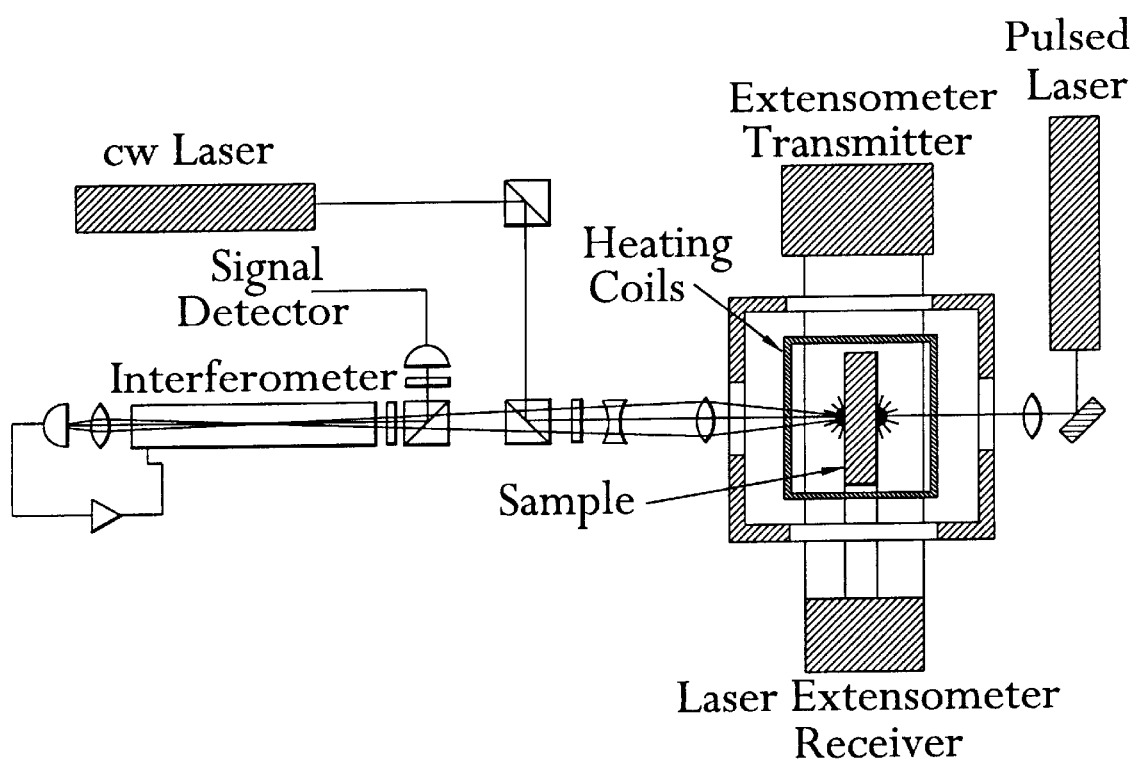

FIG. 47 Diagram of experimental configuration for the study of ultrasonic at elevated temperatures. An oven and a laser extensometer are inserted into the system to measure the dependence of ultrasonic velocity on material temperature.

Figure 48:
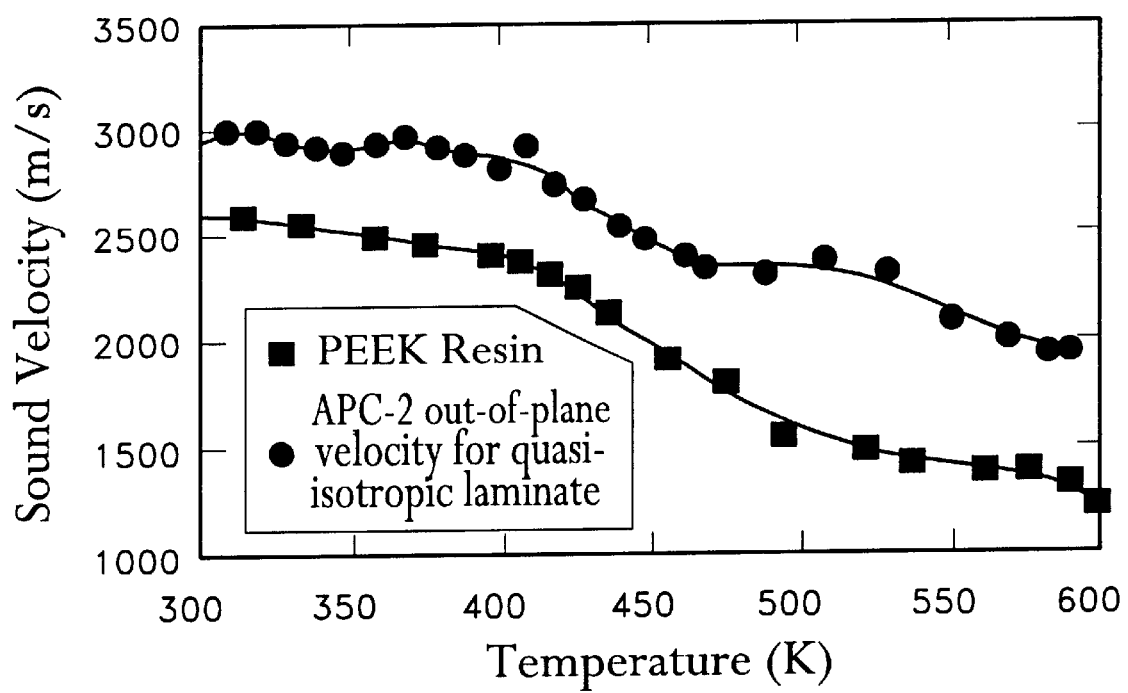

FIG. 48 Graph of dependence of material temperature on sound velocity for pure PEEK and 16 ply quasi-isotropic laminates of graphite/PEEK APC2 composite. The change in slope marks the glass transition temperature in the polymer.

Figure 49:
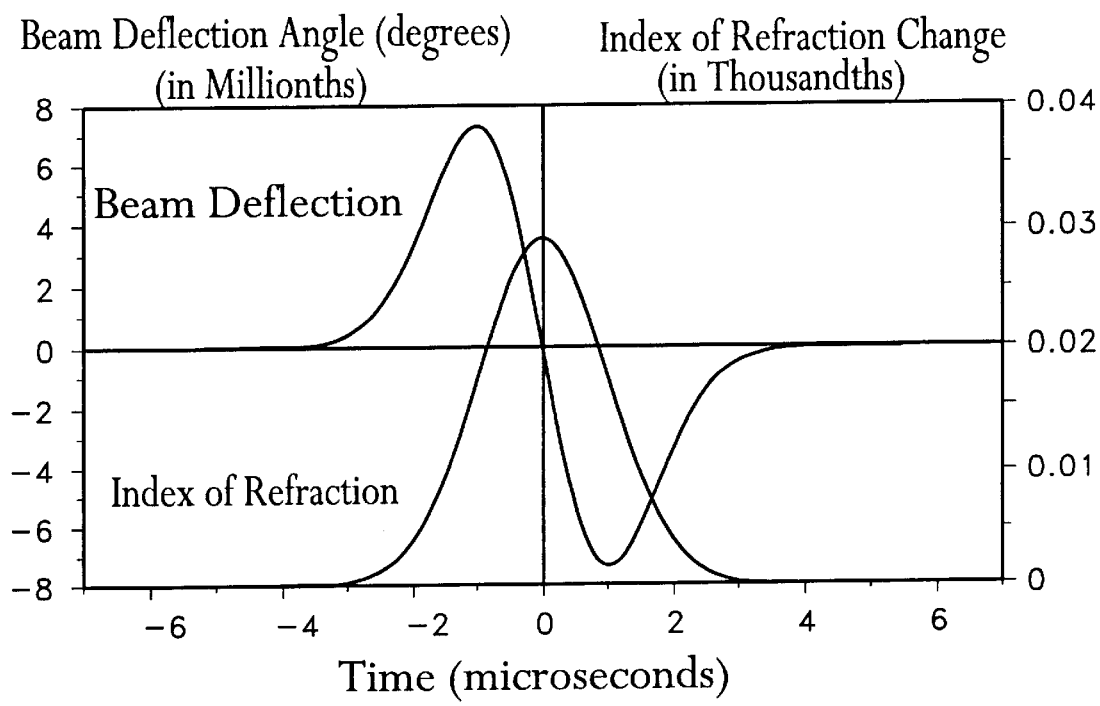

FIG. 49 Graph showing computer simulation of the beam deflection caused by a Gaussian-shaped disturbance in air's index of refraction. The original disturbance is also shown.

Figure 50:
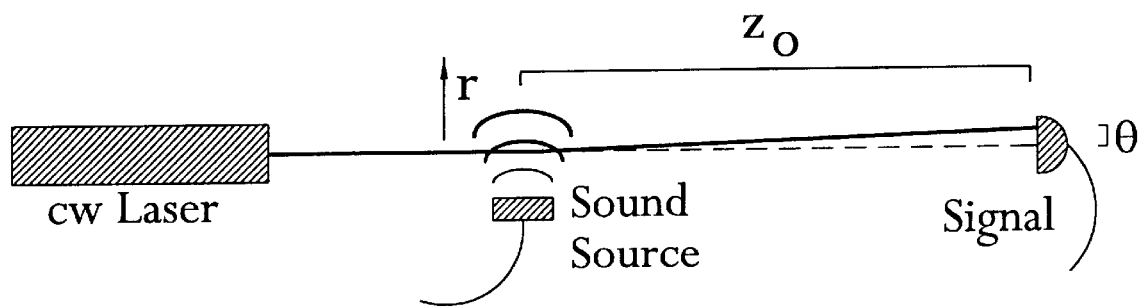

FIG. 50 Diagram of simplified set-up for gas-coupled laser acoustic detection (GCLAD). The change in the index of refraction if the gas medium which results from the acoustic wave slightly deflects the laser beam from its original position on the photodetector.

Figure 51:
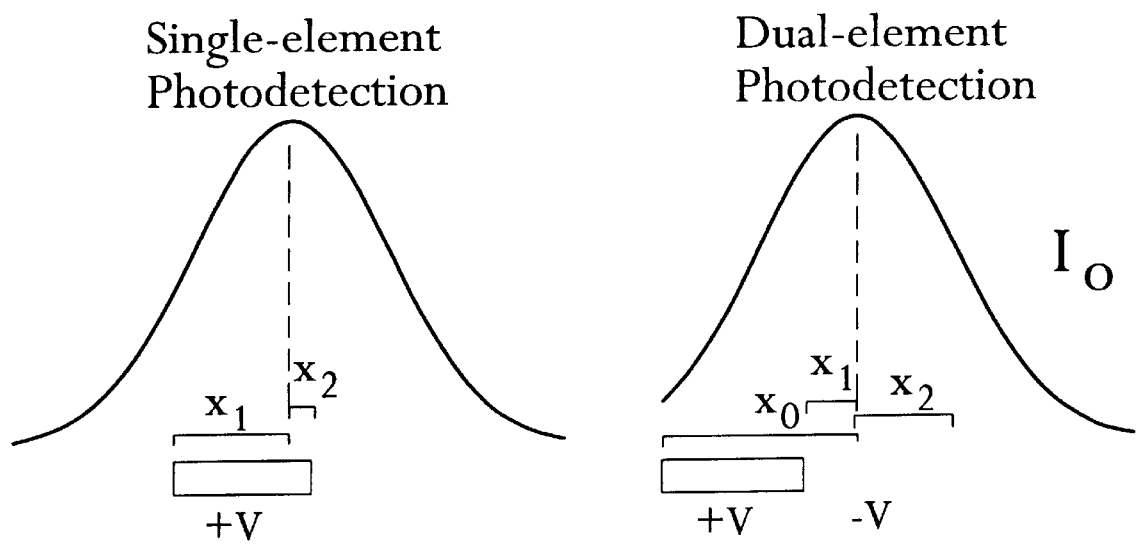

FIG. 51 Diagram of the Gaussian intensity distribution and aperture parameters for single-element and dual-element photodetection. Beam deflection detection results from the change in position of the beam, $z_0\theta$, with respect to the static position of the photodiodes.

Figure 52:
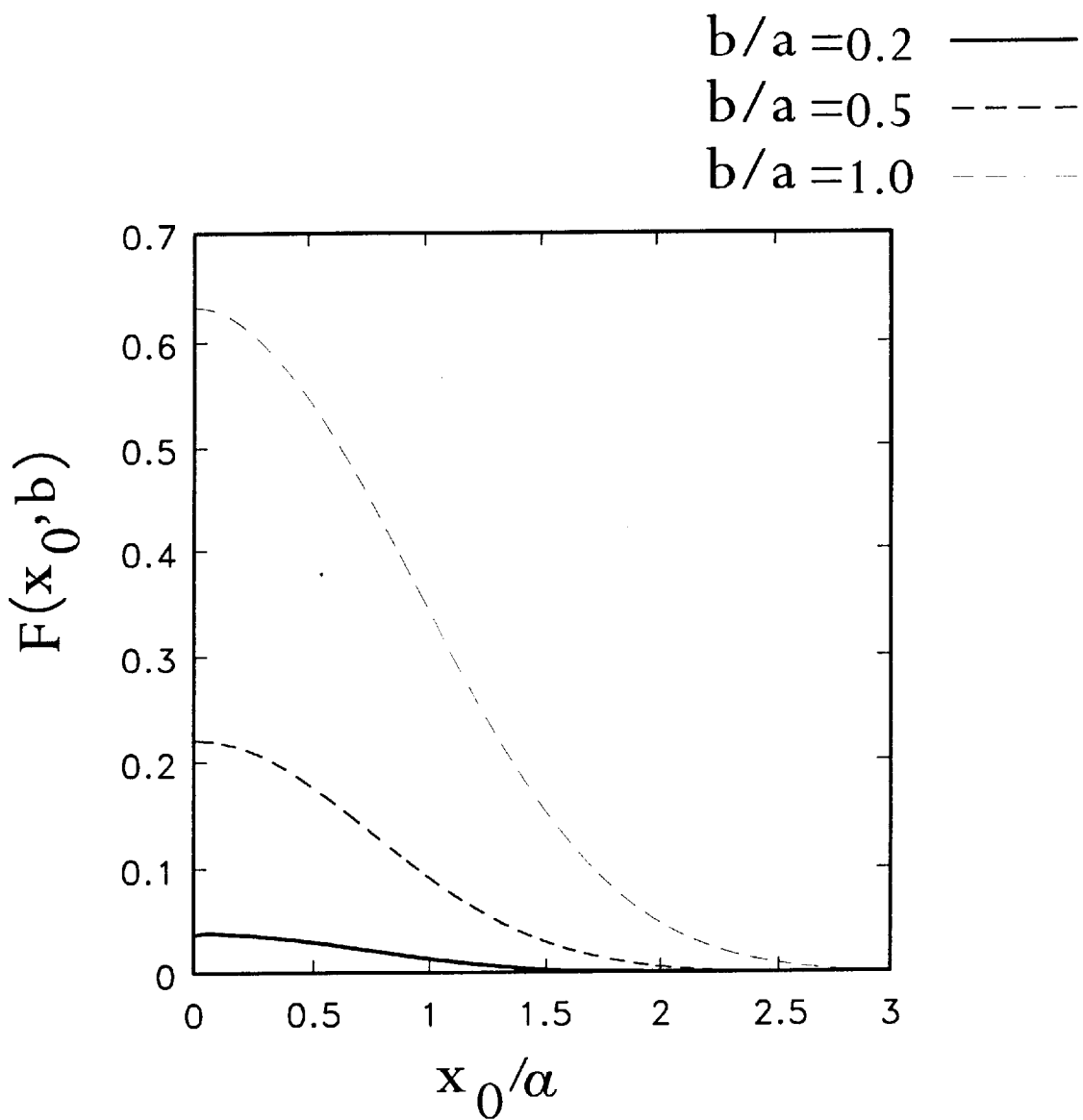

FIG. 52 Graph showing computational results of circular integration of a Gaussian intensity distribution. The plots represent different aperture diameters.

Figure 53:
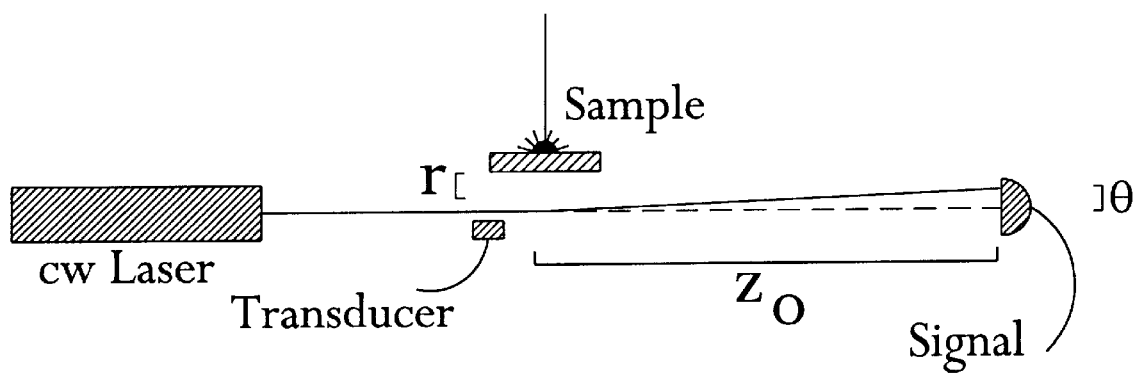

FIG. 53 Diagram of experimental arrangement for the investigation of GCLAD properties. The probe beam is directed to parallel to the sample surface to intercept the airborne acoustic waveform.

Figure 54:
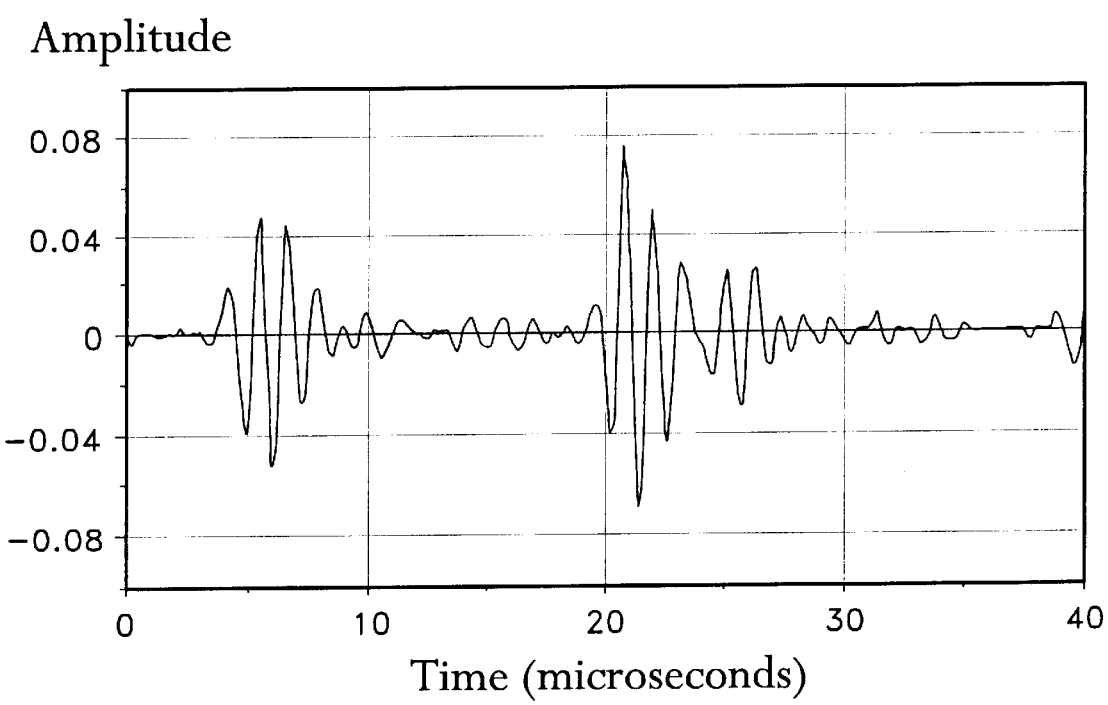

FIG. 54 A waveform generated by a contact transducer in a 8.8 mm thick carbon/epoxy composite, transmitted to air, and detected by GCLAD.

Figure 55:
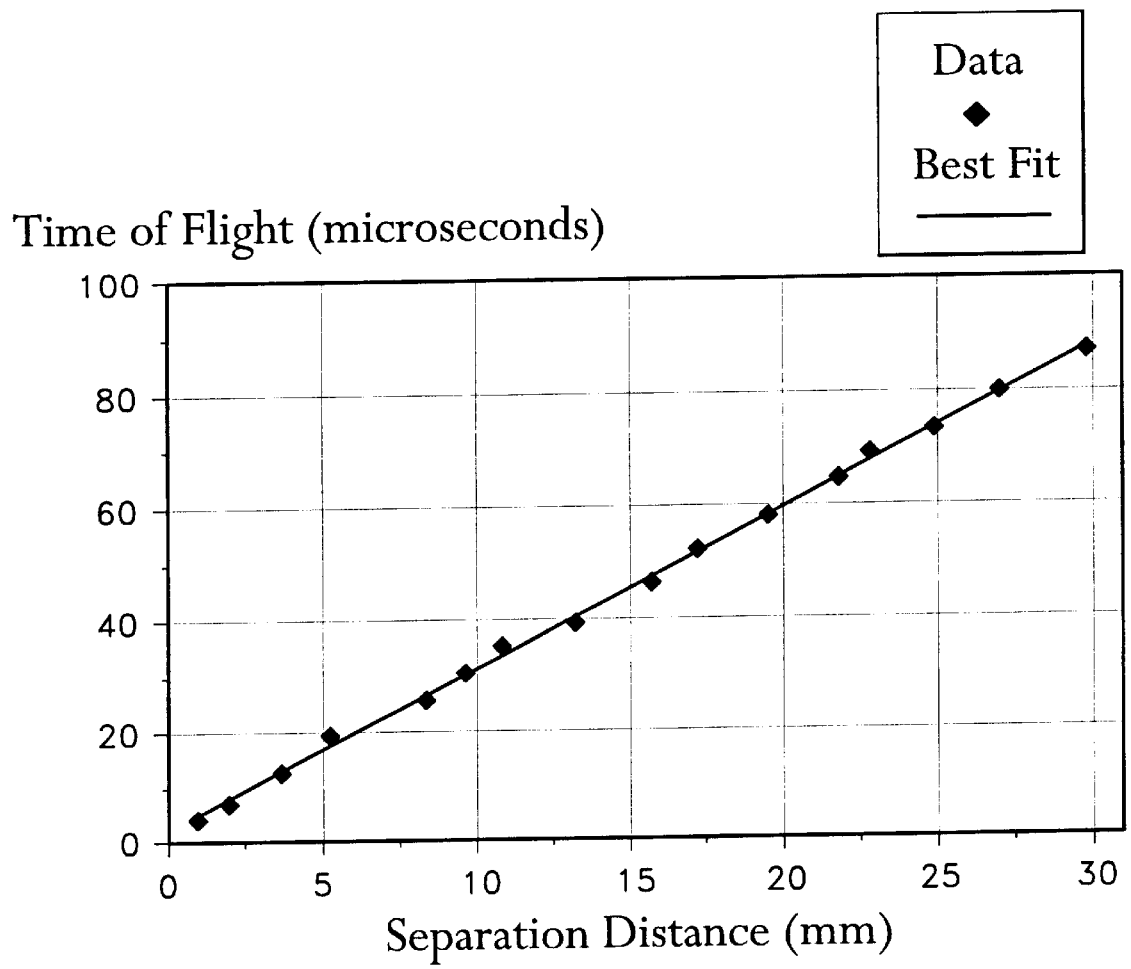

FIG. 55 Graph showing dependence of the sound wave time-of-flight on the distance between the sound source (a transducer mounted on a carbon/epoxy sample) and the laser beam. The graph reveals a slope of 349.9 m/s, or the speed of sound in air.

Figure 56:
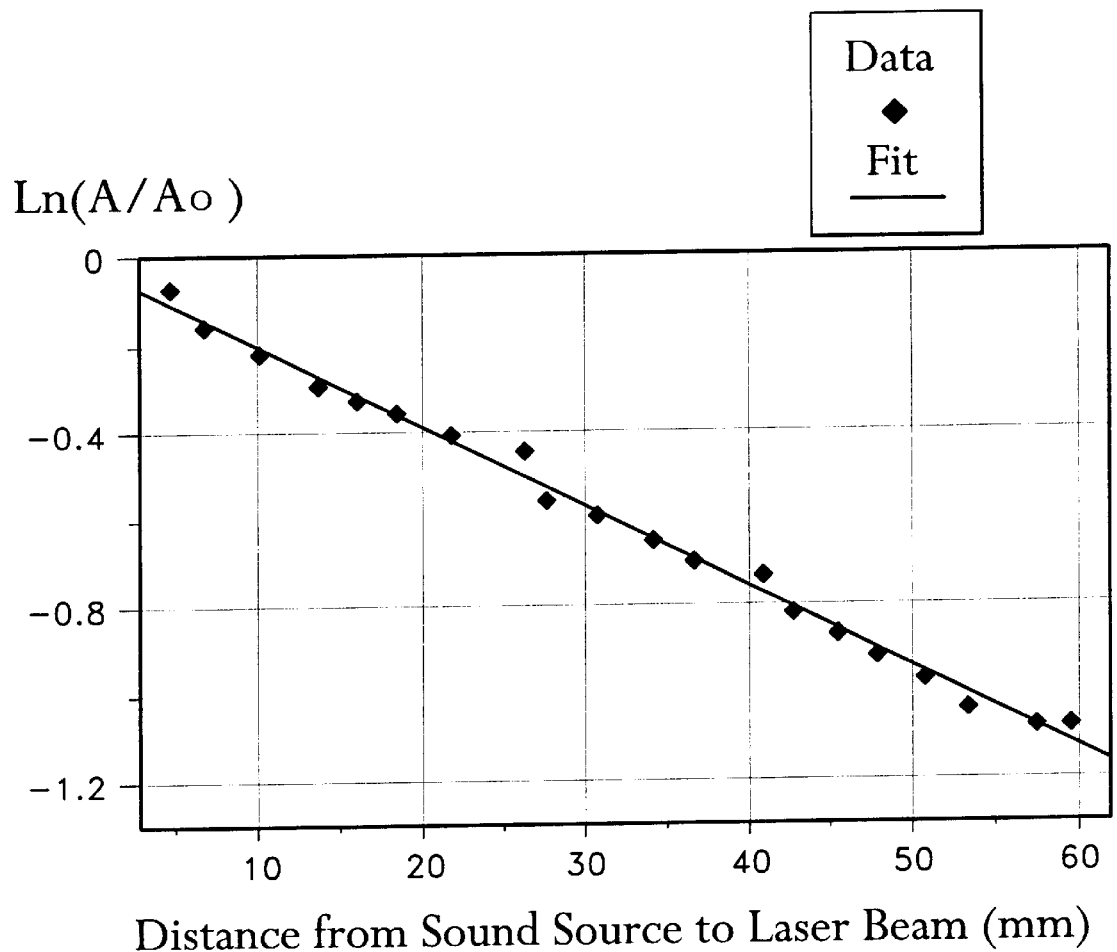

FIG. 56 Graph showing attenutation of an ultrasonic wave in air as detected by GCLAD. The acoustic waveform was generated by a 1 MHz piezoelectric transducer.

Figure 57:
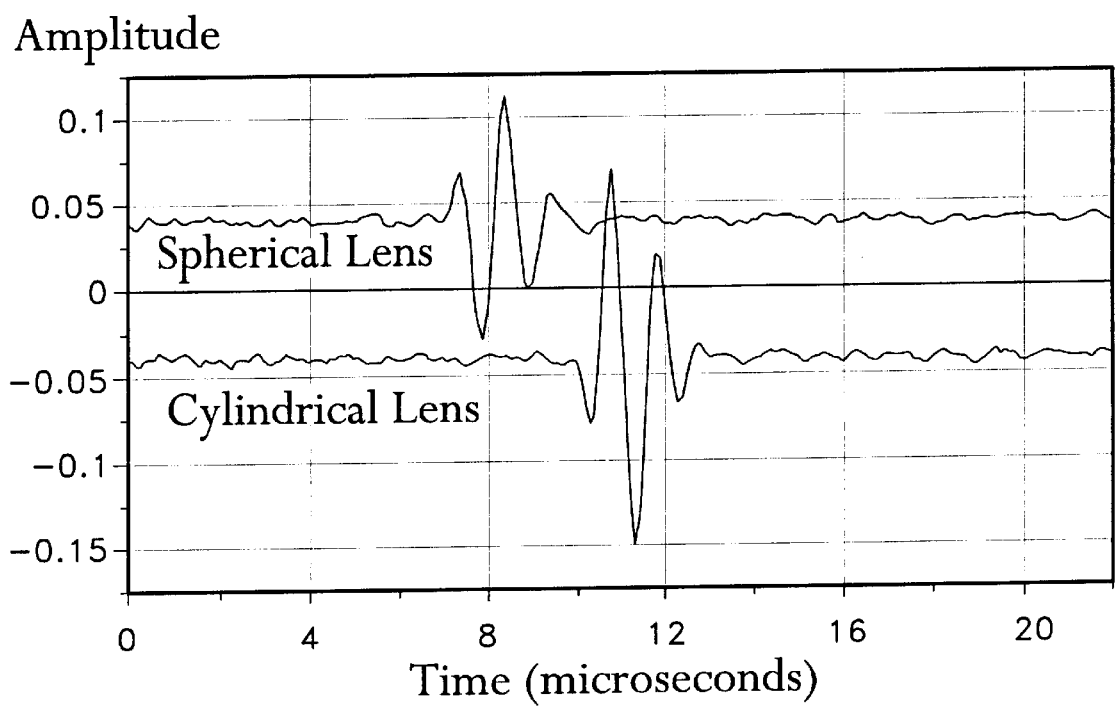

FIG. 57 Graph of ultrasonic waves detected by GCLAD using a spherical convex lens and a cylindrical lens to narrow the probe beam width in front of the acoustic source. The use of a cylindrical lens increases the interaction of the sound wave with the laser beam. In this case, the signal-to-noise ratio has almost doubled.

Figure 58:
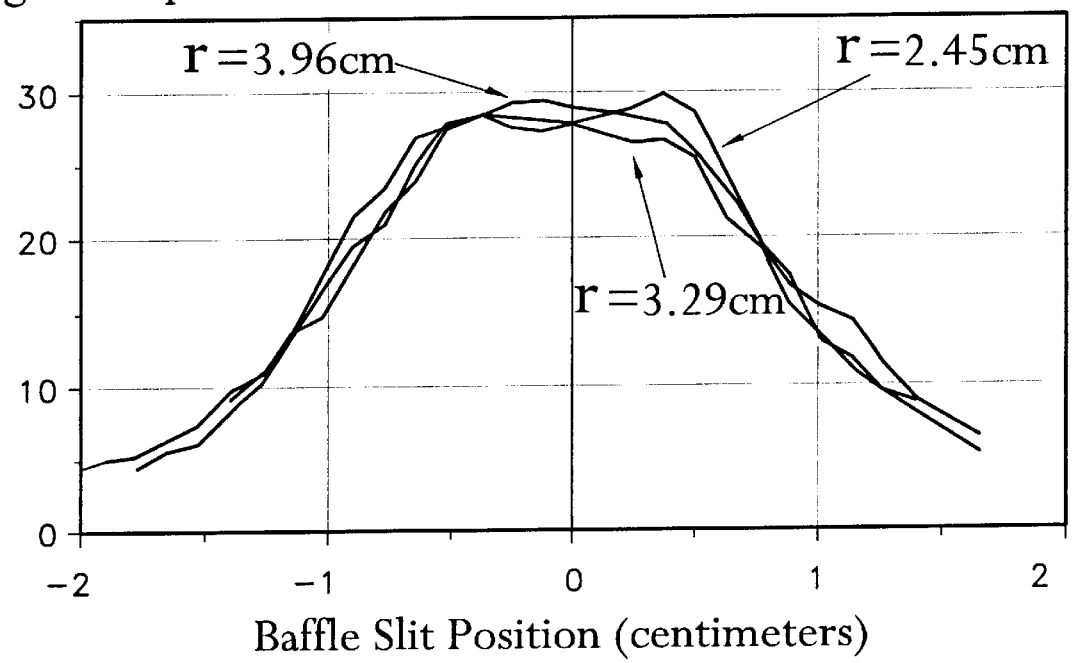

FIG. 58 Graph showing distribution of the sound field created by a transducer as detected by GCLAD. The field was measured by positioning a baffle with a narrow slit between the sound source and the laser beam. The distance from the baffle to the laser beam is shown.

Figure 59:
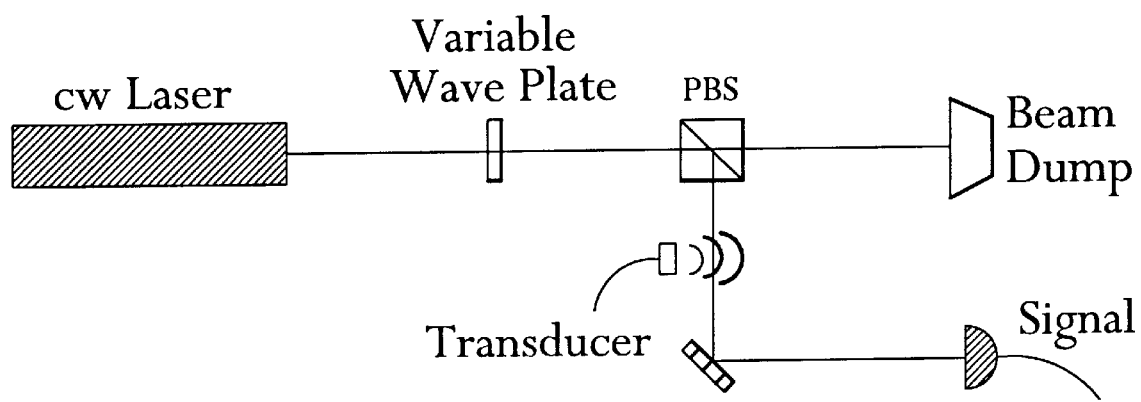

FIG. 59 Diagram of experimental setup to study the dependence of the GCLAD signal on laser intensity.

Figure 60:
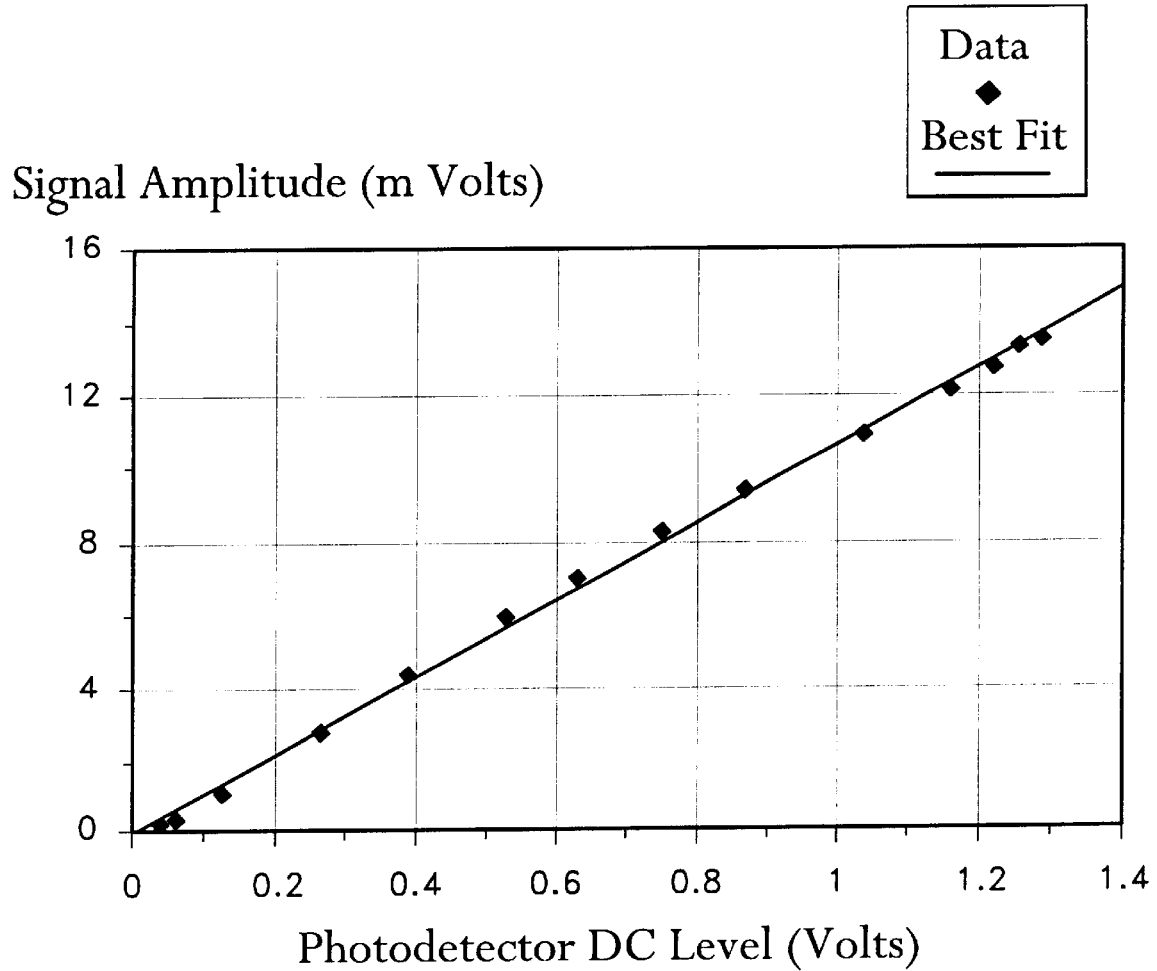

FIG. 60 Graph showing dependence of the GCLAD signal on laser intensity. The intensity was varied using polarizing beam splitters as the amplitude of the detected ultrasonic wave was recorded.

Figure 61:
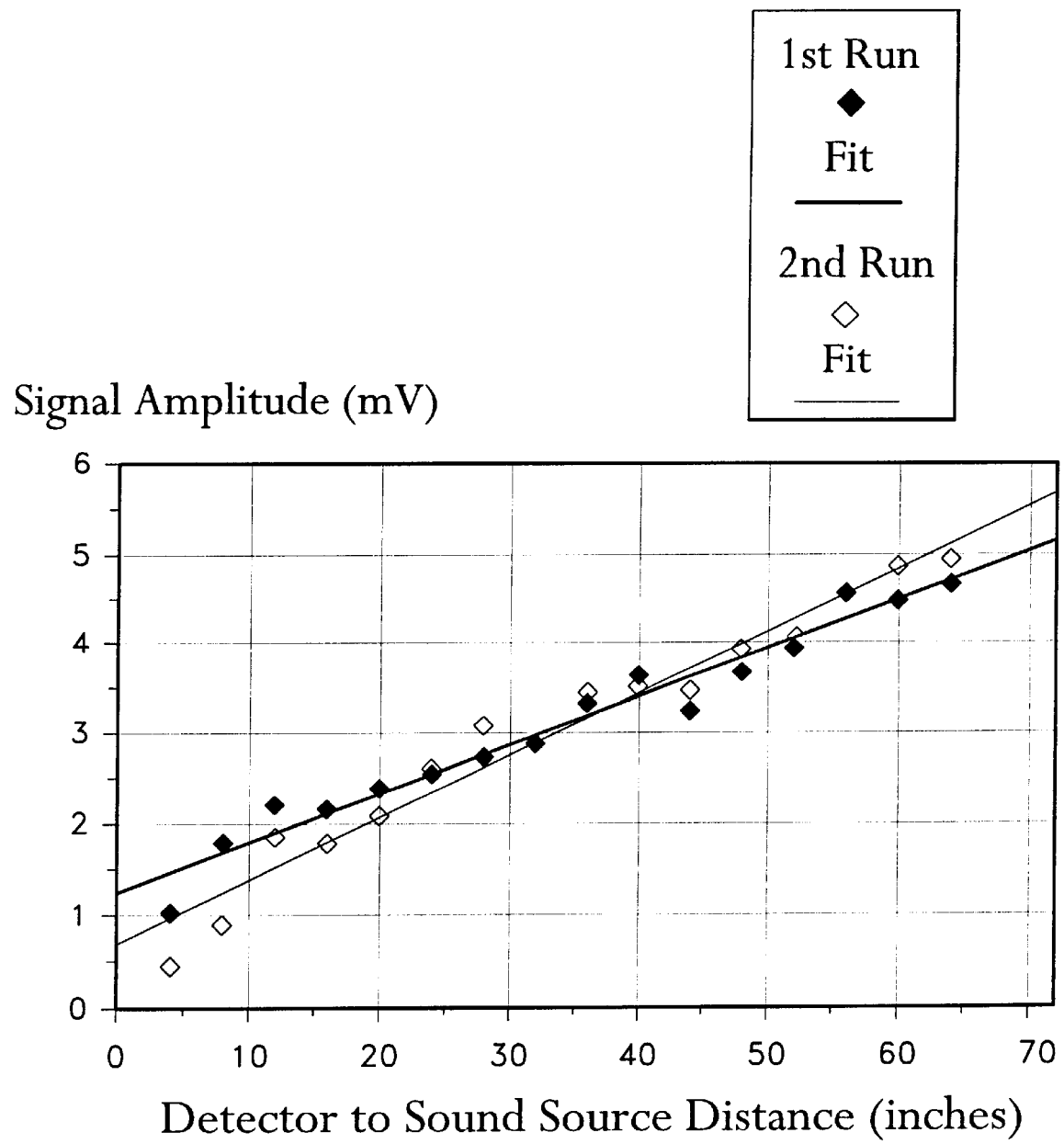

FIG. 61 Graph showing dependence of the GCLAD signal on the distance from the photodetector to the beam deflection point. The linearity provides evidence of beam deflection.

Figure 62:
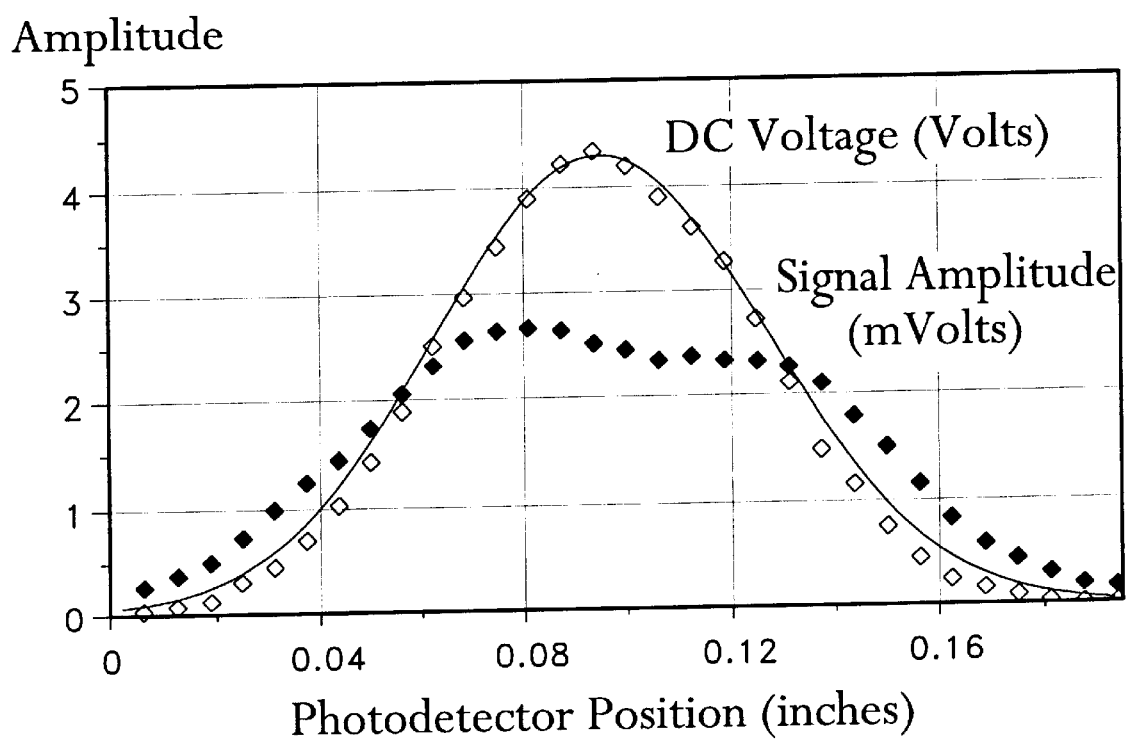

FIG. 62 Graph showing signal amplitude and dc voltage level of the single-element photodetector as the photodetector is moved transversely to the laser beam. The results demonstrate that the signal is dependent on the change of slope of the Gaussian profile of the laser beam.

Figure 63:
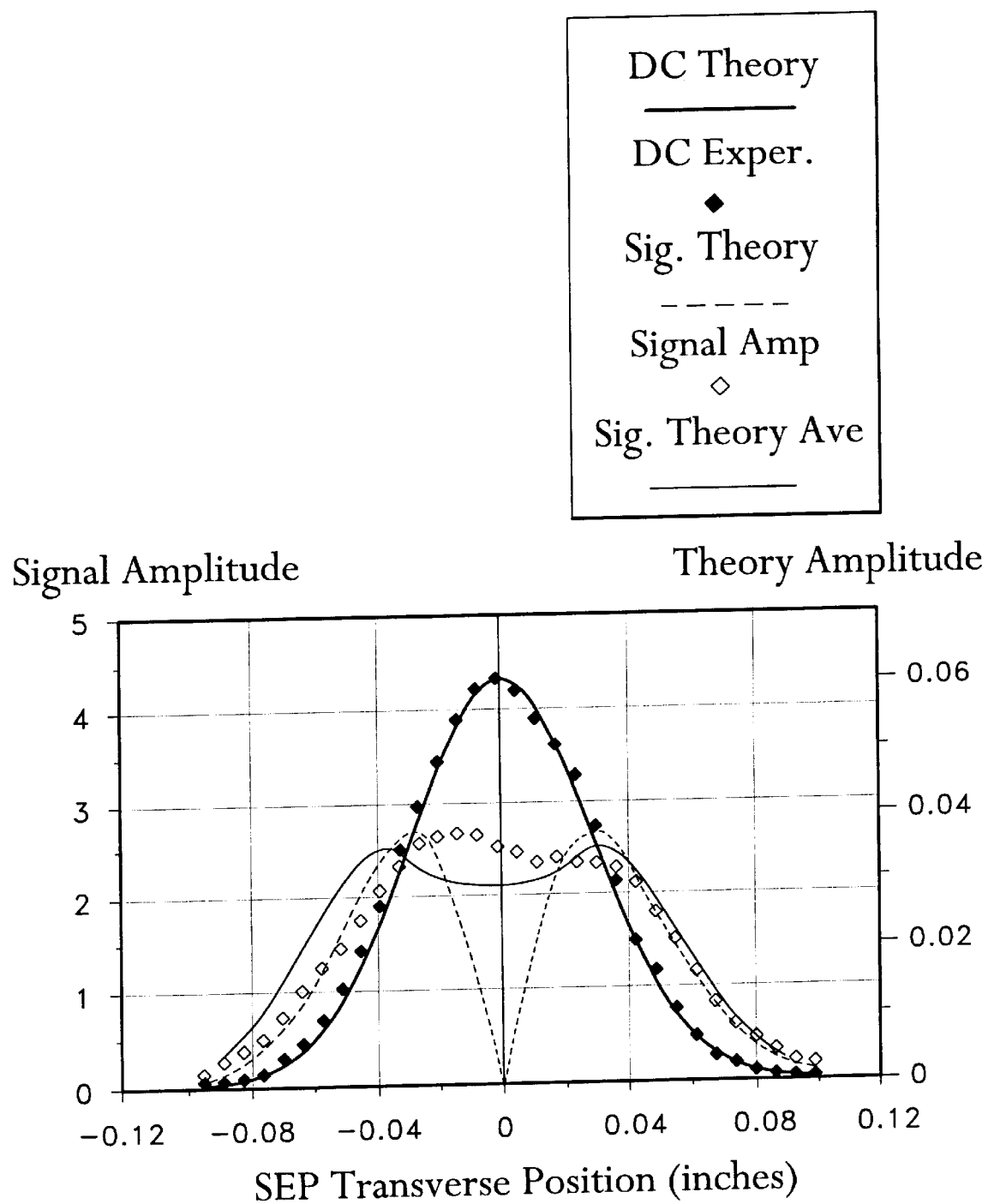

FIG. 63 Graph showing comparison of signal amplitude and dc voltage level of transversely-moved single-element photodetector with theory. The theoretical signal amplitude more closely resembles the empirical data when each point is replaced by an average of the twelve surrounding points.

Figure 64:
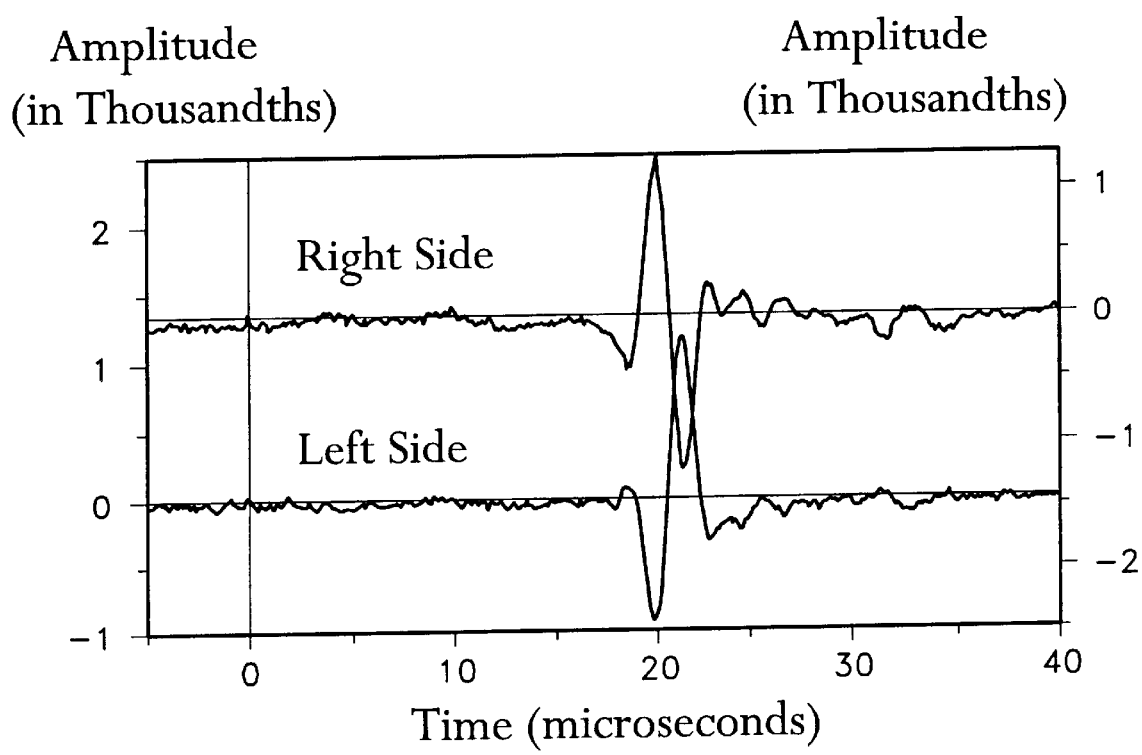

FIG. 64 Waveforms taken with the photodetector positioned on opposite slopes of the Gaussian-shaped laser spot. The polarity change adds evidence to the idea that the detected signal is dependent on the change of slope of the laser beam profile.

Figure 65:
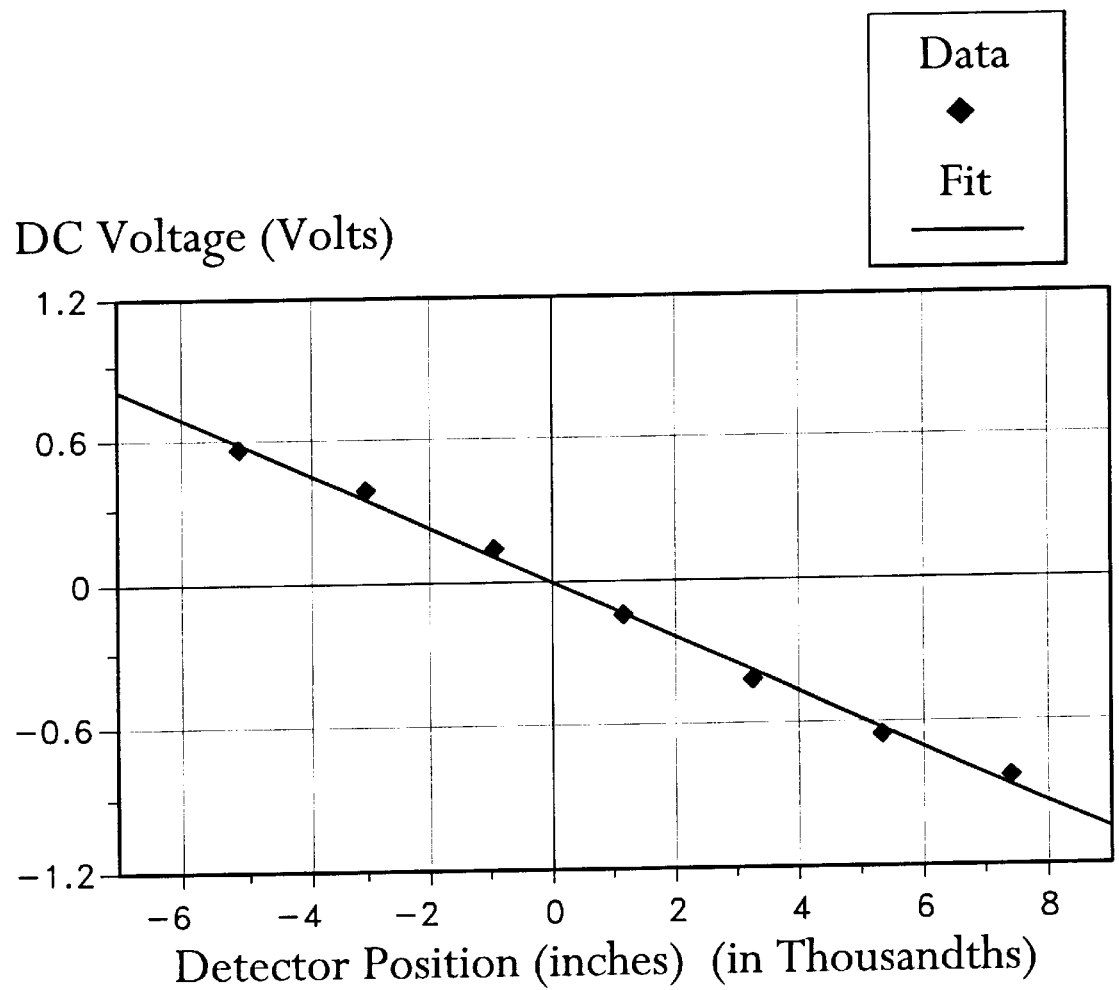

FIG. 65 Calibration curve for dual-element photodetector as a function of transverse position. The beam deflection angle can be found by dividing the signal amplitude by the slope and $z_0$.

Figure 66:
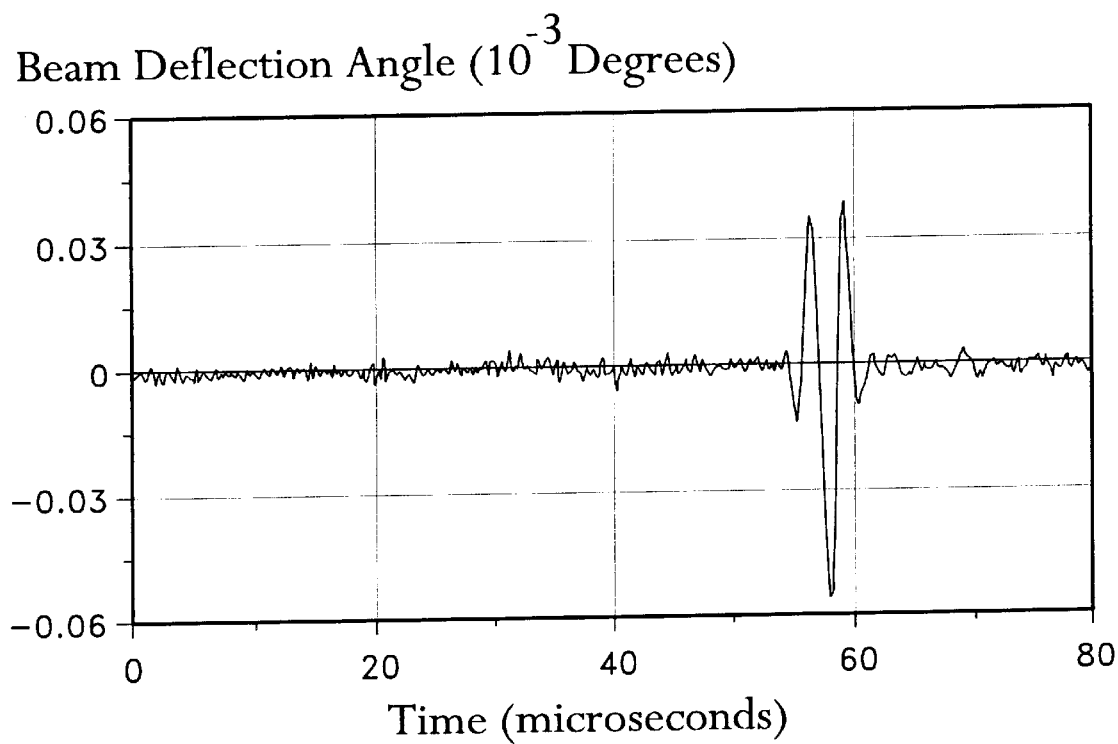

FIG. 66 An ultrasonic waveform, generated by transducer and detected via GCLAD by the dual-element photodetector, as a function of beam deflection angle.

Figure 67:
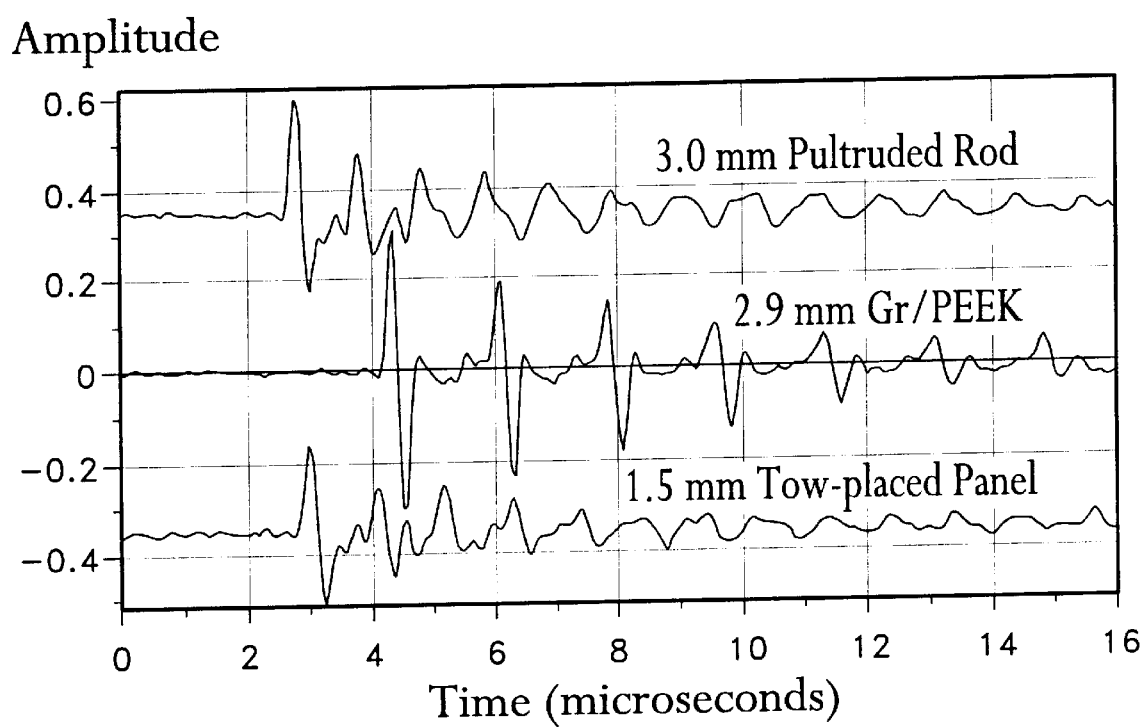

FIG. 67 Laser generated/GCLAD detected ultrasonic waveforms in various polymer/graphite composites. The laser pulse strikes the sample at t = 0. The time to the first wave is a combination of the time-of-flight in the solid, and the time-of-flight in air.

Figure 68:
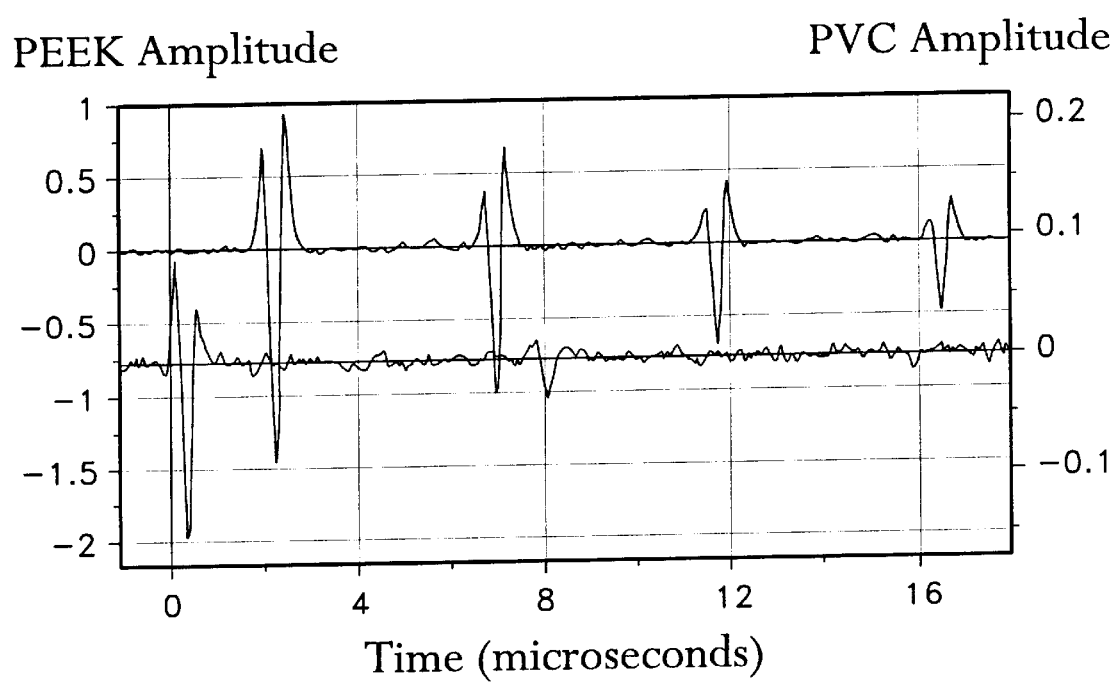

FIG. 68 Laser generated/GCLAD detected ultrasonic waveforms in PEEK and PVC polymers. The generating spot size was 0.8 cm$^2$.

Figure 69:
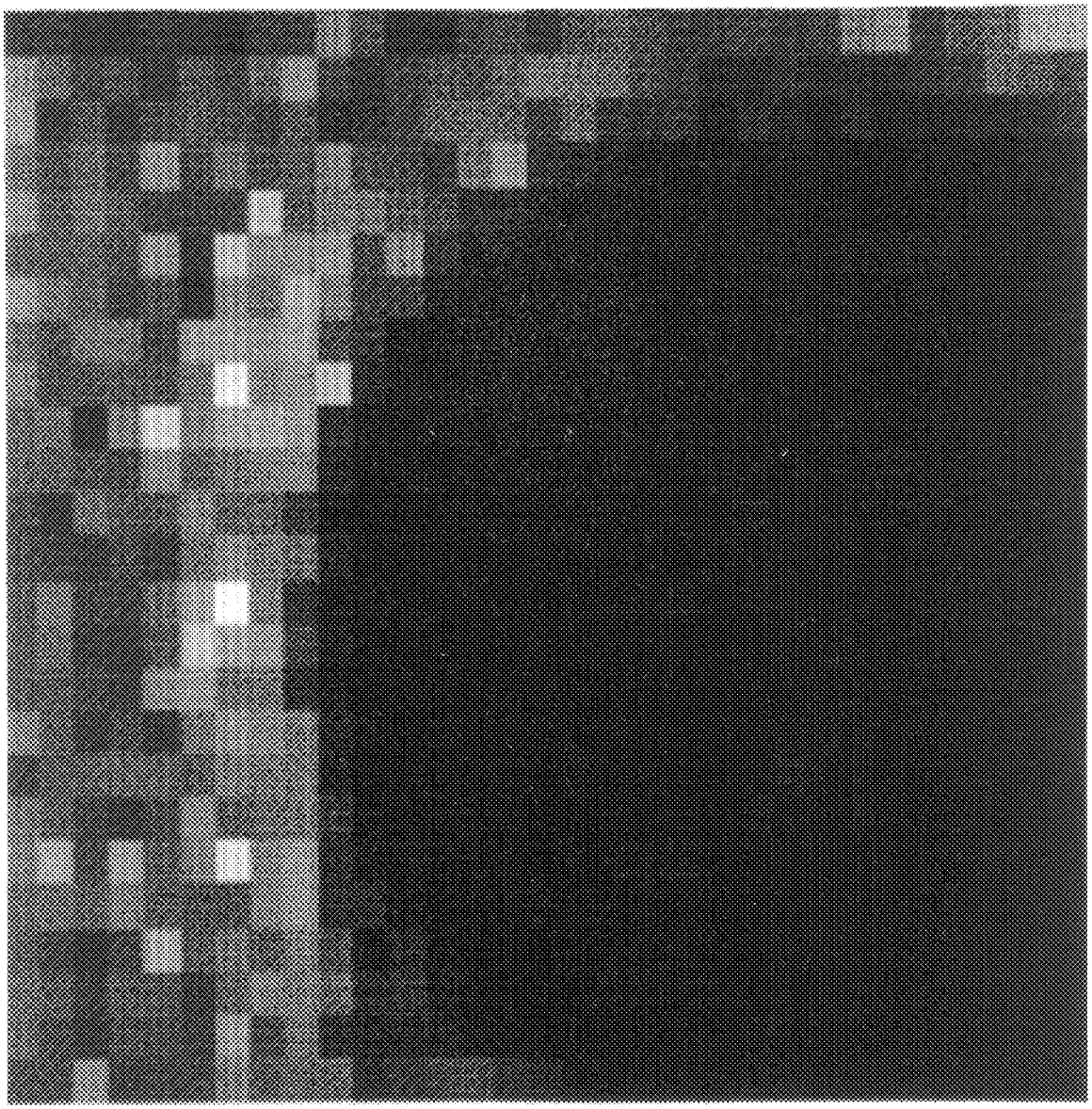

FIG. 69 A C-scan of an 8.9 mm graphite/epoxy composite with an embedded Teflon flaw using air-coupled laser detection. The flaw has the approximate surface area of a quarter.

Figure 70:
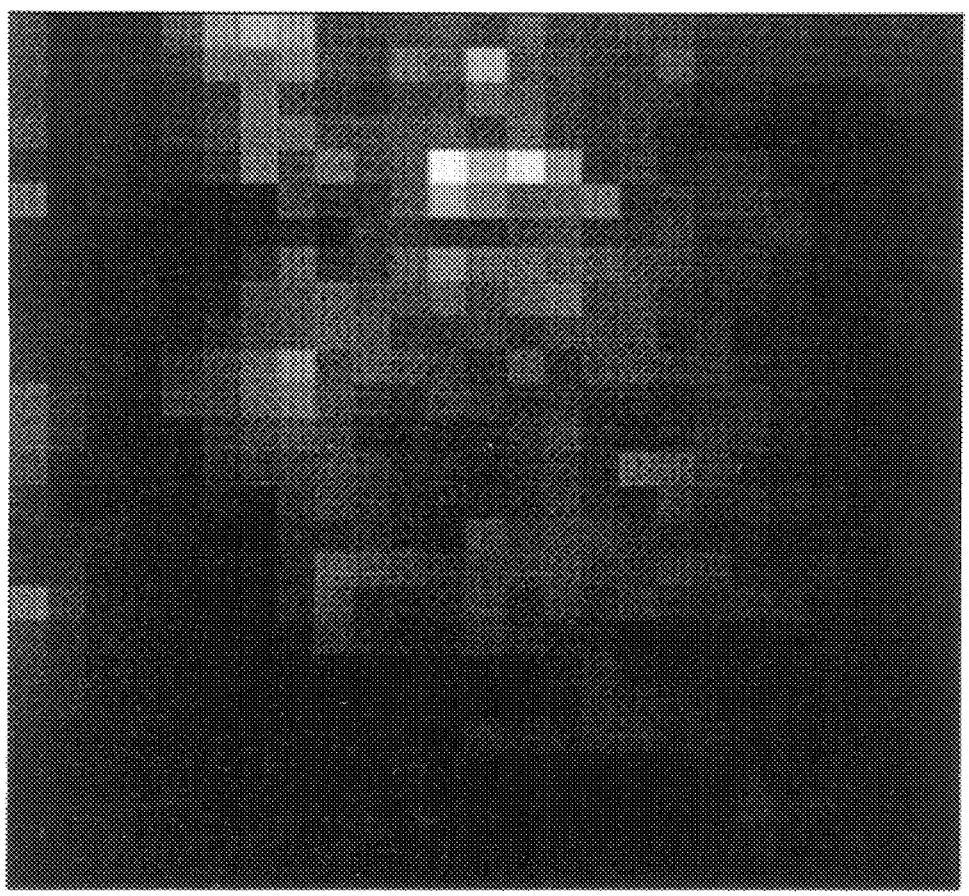

FIG. 70 A 25 × 25 mm C-scan of a tow-placed panel (AS-4/PEKK, [0/90]$_{2S}$) with prominenet flaws using air-coupled laser detection. Light areas show good ultrasonic reception.

-continued

BRIEF DESCRIPTION OF THE DRAWINGS

Figure 71:
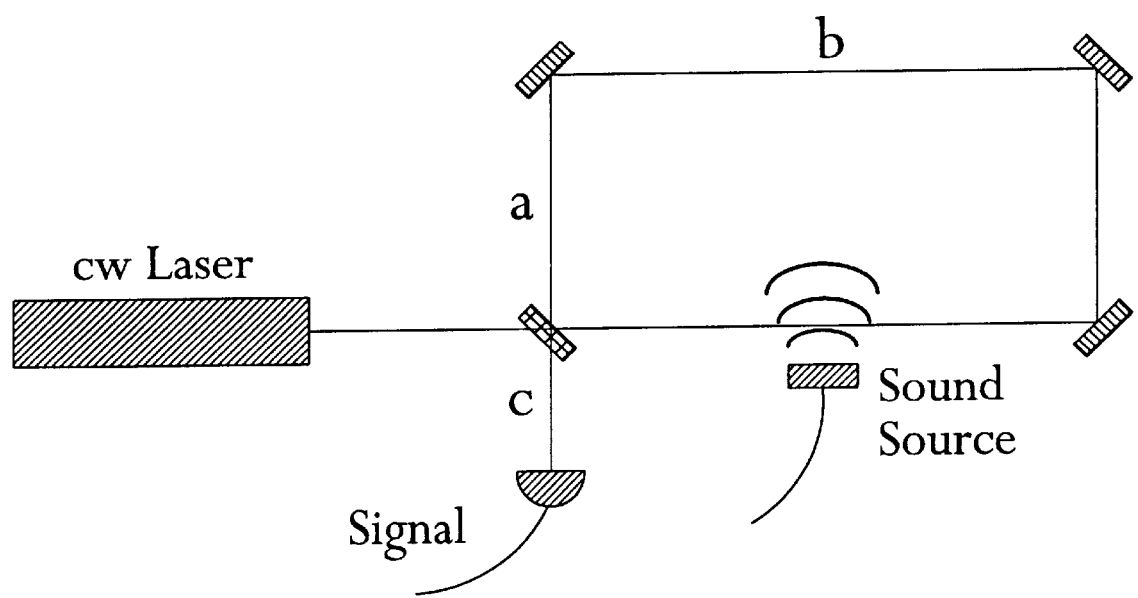
Figure 72:
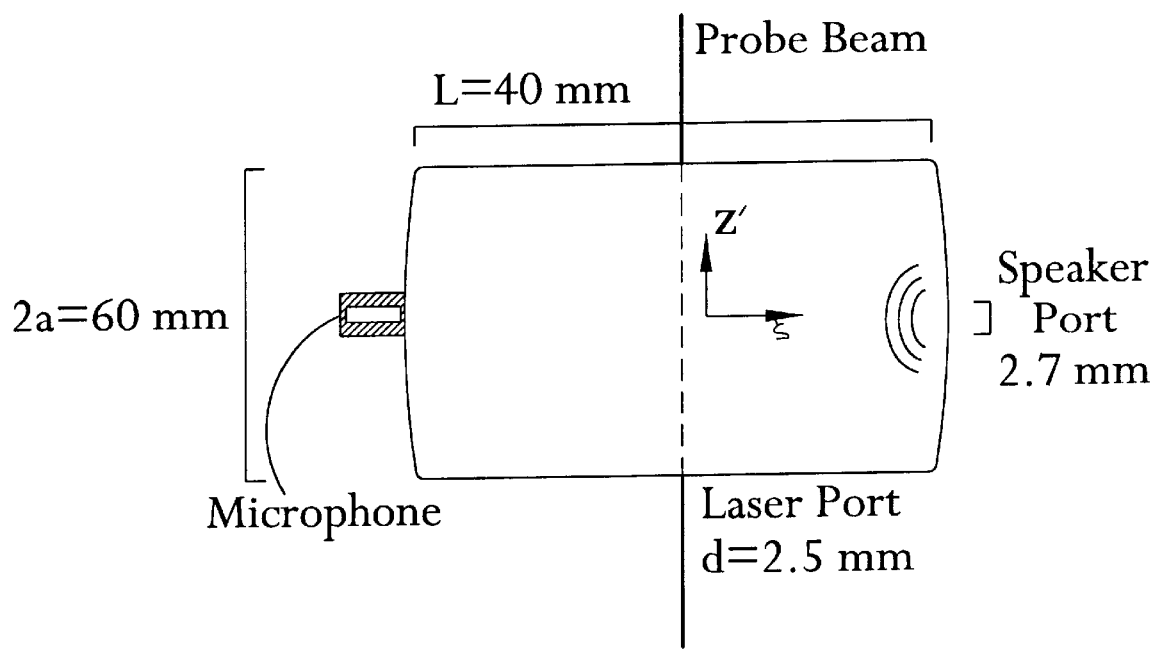
Figure 73:
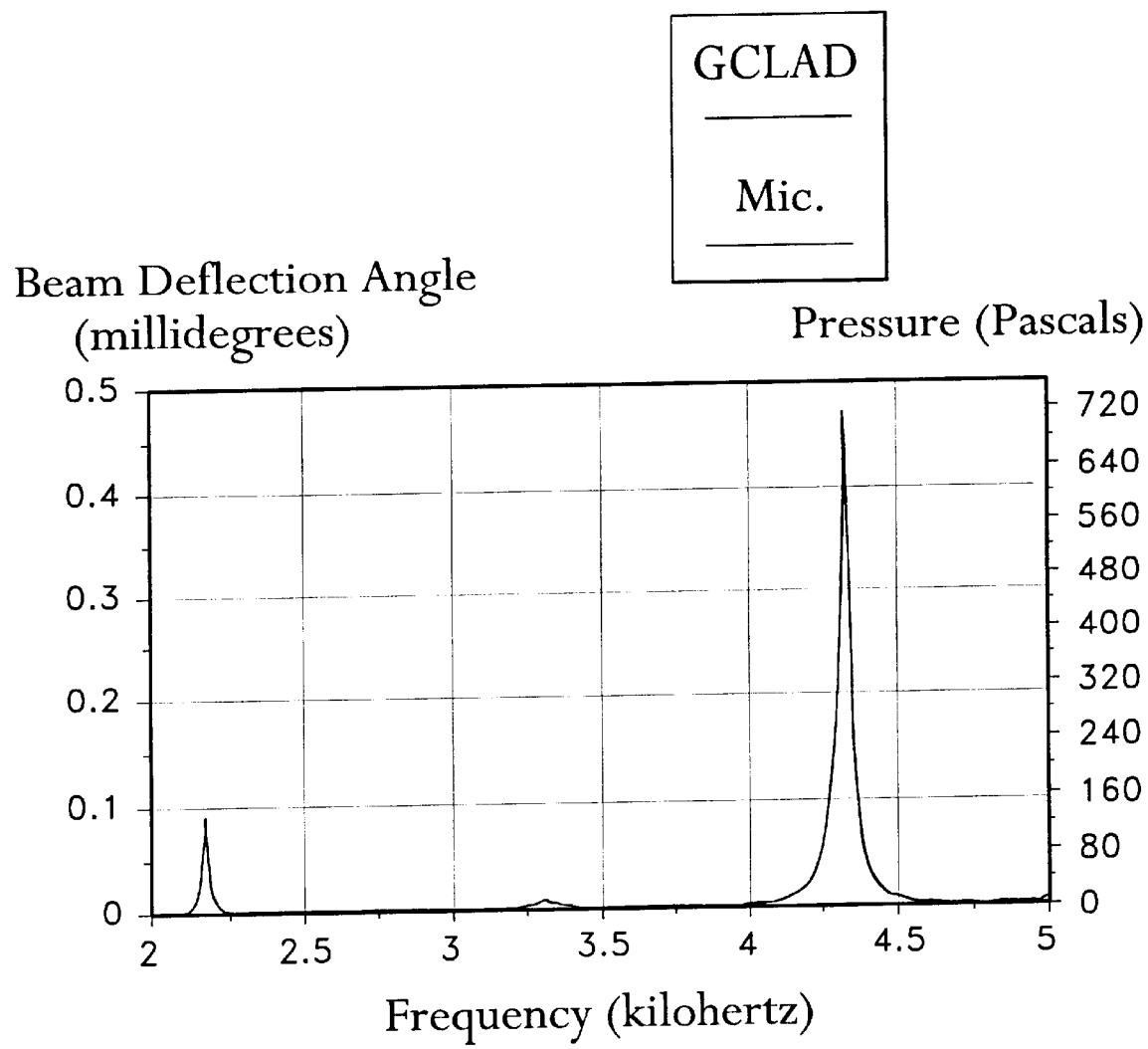
Figure 74:
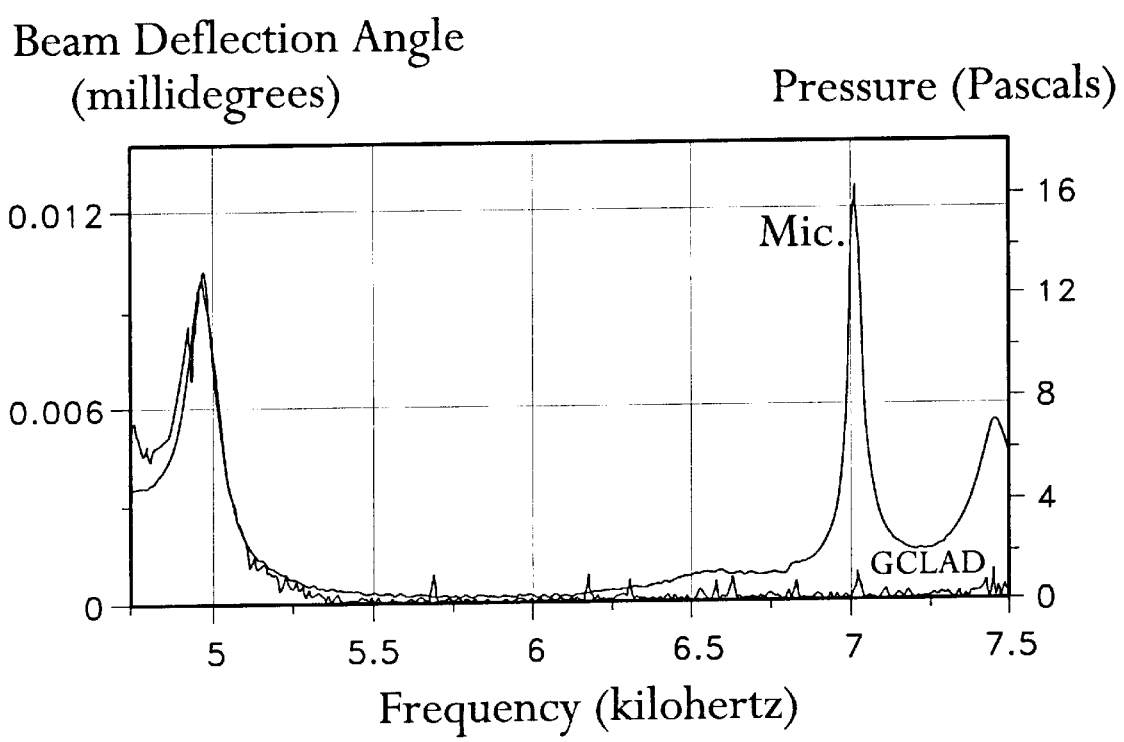
Figure 75:
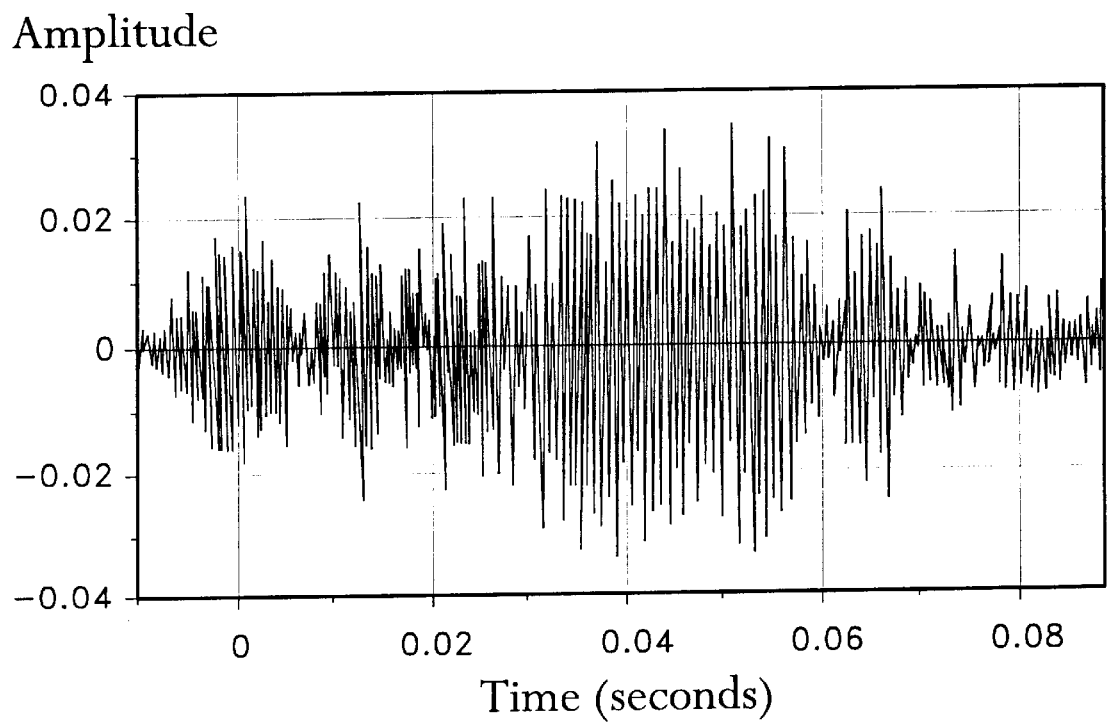
Figure 76:
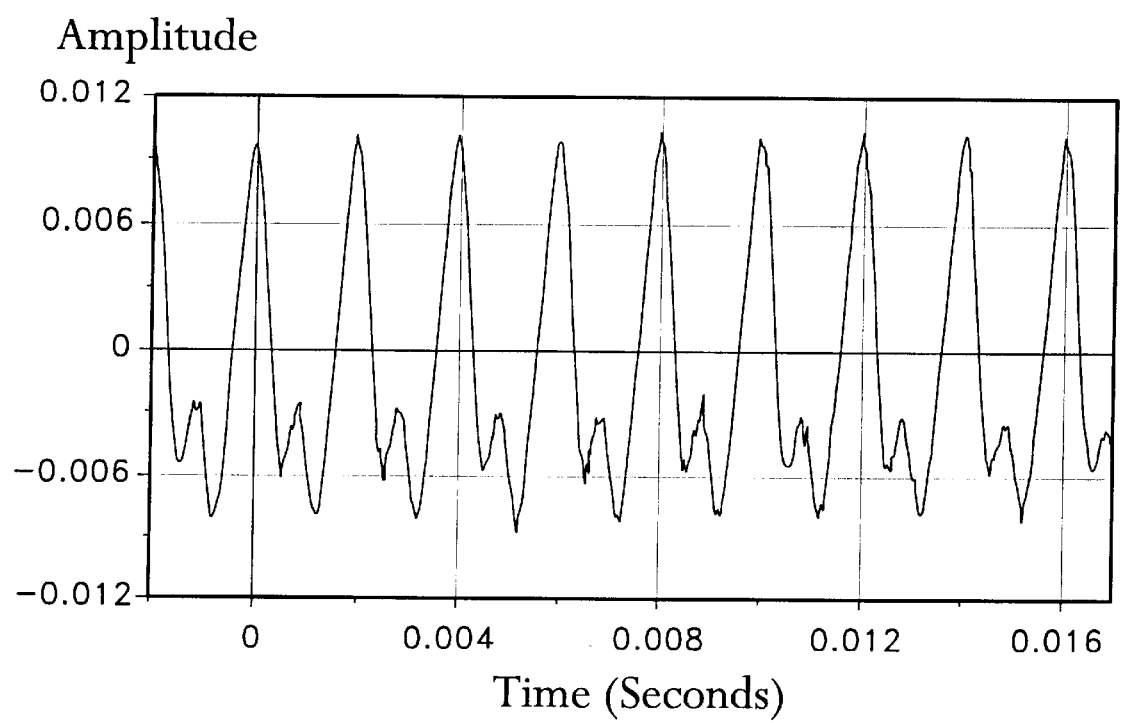

FIG. 71  Diagram of compact loop configuration of GCLAD. Three standard mirrors and one partially reflecting mirror allow multiple passes of the laser beam in front of the sound source.
FIG. 72  Diagram of experimental setup for measuring the frequency distribution in a cylindrical cavity using air-coupled detection. Interior dimensions are shown.
FIG. 73  Graph showing frequency response of a cylindrical cavity measured by a conventional microphone and GCLAD. The data has been calibrated to compare the beam deflection angle to changes in ambient pressure resulting from the sound waves. The two techniques are consistent in this frequency range.
FIG. 74  Graph showing frequency response of a cylindrical cavity measured by a conventional microphone and GCLAD. The frequency range displays diverse results near 7 kHz.
FIG. 75  Graph sowing the syllable "ba" recorded by the laser microphone. The wave pattern was recorded by GCLAD onto a digital oscilloscope.
FIG. 76  Graph showing a high B-natural played on a bassoon and recorded by the laser microphone.

Chapter 2

INTRODUCTION 2.1 Ultrasonic Inspection of Composite Structures

Recent years have seen the increased use of graphite/polymer composite materials as a lightweight alternative to metals. Graphite fibers can be laid in a specified arrangement in the polymer matrix such that strength properties are increased along desired directions. Before any composite structures are integrated into industrial applications, the risk of product failure needs to be minimized. Processes need to be developed which address one or more of the following problems: (i) characterization of the spatial variation of the material's composition, configuration, voids, inclusions or porosity, (ii) determination of the magnitude and extent of residual stresses, (iii) determination of the presence and location of fiber/matrix disbonds and/or failure, and (iv) detection of the presence and extent of matrix cracking [2].

To prevent component failure, on-line and post-production nondestructive inspection of composite parts is necessary from both quality and safety standpoints. Common methods of composite evaluation include visual, radiographic, thermographic, acoustic-emission, optical, ultrasonic and vibrational inspection [3]. Visual inspection calls for the close examination of surface qualities, such as color or texture, to make judgements about the interior of the sample. Radiographic inspection exploits the differential in absorption of radiation between flawed and unflawed material. X-rays and γ-rays are commonly used. In thermographic inspection, a component is actively or passively heated, while the temperature on the surface is monitored as a function of time using an infrared video camera. Flaws are detected as a result of their difference in thermal diffusivity. Acoustic emission is a technique in which the composite is lightly stressed. Microscopic failures produce acoustic noise which can be detected by sensitive transducers. Noise amplitude is used to compare the sample with a reference sample. Optical inspection, also called shearography, uses holography to detect minute dimensional changes as a component is stressed. Vibrational inspection uses local pulse excitation to exploit the sonic properties of the component. Natural frequency and damping characteristics can be evaluated and compared to a defect-free specimen.

Ultrasonic inspection exploits differences in acoustic impedances between good and flawed portions of the component. An acoustic pulse is introduced into the sample. The pulse travels at a well-defined velocity until it encounters a density change where it is partially or completely reflected. Once detected, the pulse is compared to ideal specifications to determine the possibility and extent of a flaw. This method is capable of detecting delaminations, disbonds, voids and foreign inclusions [3]. It can also determine changes in fiber fraction, fiber orientation, and thickness. The ultrasonic velocity, typically between 1 and 4 $\mu$s/mm for composites, allows for data sampling at high repetition rates.

Figure 1:
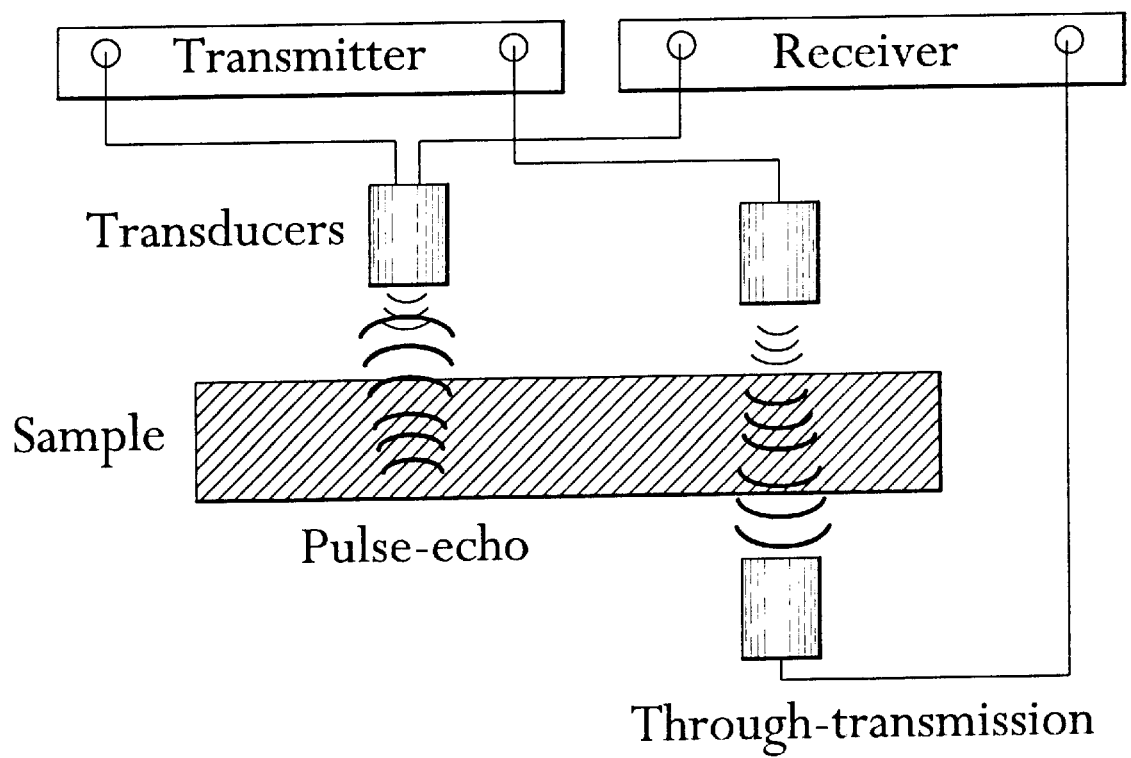
FIG. 1  Diagram of pulse-echo and through-transmission modes of conventional ultrasonic inspection.

Ultrasonic inspection can be realized in either of two configurations, shown in FIG. 1. The through-transmission method uses separate transducers, aligned on opposite sides of the component, for generating and receiving the pulse. Flaws are detected when the generated acoustic pulse does not penetrate as expected to the second transducer. The pulse-echo method uses the same transducer for generating and receiving the pulse. Flaws are detected when the pulse is not detected in a time period established by the velocity of the pulse in an unflawed material. Reflections from flaws will send the waveform back to the detection point earlier than expected. The time-of-flight of these pulses can be used to determine the depth of the flaw within the material. The pulse-echo method is mandatory when only one side of the test sample can be accessed.

Ultrasonic inspection provides several options for data acquisition. In an A-scan, the time between the reflection from the front surface and the reflection from the back surface is measured and compared to the expected ideal value. The waveform is viewed on a as the transducer, used in pulse-echo mode, is moved point-by-point, producing new A-scans. A flaw is detected when the time between echos reduces significantly. In a B-scan, the time between echos is displayed as a function of position along the line traveled by the transducer. In a C-scan, the transducer is moved line-by-line providing a planar image of the scanned region. In a through-transmission configuration, "shadows", produced by the absence of a detectable waveform, reveal the location of defects. In a pulse-echo configuration, information about the depth of the flaw can be acquired. With sophisticated signal-processing software, the data may be exhibited in a ply-by-ply fashion or a volumetric display.

With the exception of newly developed air-coupled transducers, conventional ultrasonic methods require a liquid or solid couplant to transmit the pulse from the transducer to the sample. In certain cases, the component is immersed in a water tank to achieve the inspection. Since the presence of the couplants could contaminant the production process, inspection usually takes place after production is completed. The sensitivity of transducers to temperature also prevents application in high-temperature situations. To overcome these difficulties, industry has sought non-contact solutions to accomplish their ultrasonic inspections.

2.2 Laser Ultrasonic Inspection of Composite Structures

The use of lasers to generate and receive the ultrasonic pulse from the test sample has been viewed as a viable alternative to contact and immersion techniques [21]. An energy pulse emitted from a high-powered laser creates a thermoelastic expansion when it strikes the surface of an opaque solid. The thermoelastic expansion initiates the ultrasonic pulse in the material, in a sense using the material as the transducer. As a result of the optical absorption properties of graphite-fiber composites, the efficiency of generation is greater than in metals. Also, the amplitude of acoustic pulses generated by laser are typically greater than those generated by contact transducers. The first studies into laser ultrasonics (LU) used pulse lasers for generation and contact transducer for detection.

Different schemes have been investigated to detect the acoustic pulse after transmission through the material. The most common method is the use of a laser interferometer system to detect either the surface displacement or the surface velocity accompanying the pulse. Light from a continuous wave laser is directed to the desired detection point. The phase or frequency of the scattered light is altered by interaction with the surface disturbance. The light is gathered by suitable optics into the interferometer which converts the phase or frequency change into an intensity change. The intensity change is picked up by a photodetector resulting in a signal proportional to the acoustic surface displacement or surface velocity.

Laser ultrasonics can be performed remotely with comparable sensitivity to more conventional ultrasonics [21]. Through use of motorized X-Y mirrors or a fiber optic delivery system, the point of measurement can be moved quickly and over complicated geometries. The geometry of the acoustic source can be altered easily by modifying the generation optics system. High resolution can be obtained without reducing detection sensitivity. There are also no fundamental restrictions on surface temperature.

The LU system used for this study employs a pulsed Nd:YAG laser to generate the acoustic pulse, and two detection schemes. The first uses a continuous wave (cw) Nd:YAG laser couples with a confocal Fabry-Perot interferometric (CFP) detection system, first presented by Monchalin et al. [4]. Compared to other types of interferometers, the CFP interferometer is less sensitive to low-frequency vibrations which may appear in an industrial environment and contaminant the signal acquisition. The CFP interferometer also does not require the optical smoothness of the sample demanded by other interferometers. This is a definite advantage when applied to polymer/graphite composite materials, which commonly are not as smooth as metals. The second method, newly discovered in the course of this research project, passes the cw detection laser parallel to the sample surface. The ultrasonic wave, when transmitted to the air, creates a change in the air's index of refraction. The bending of the laser beam through this affected area is then detected by a position-sensitive photodetector. The second method has a decided advantage over interferometric detection as a result of the total independence of the surface qualities of the component.

Chapter 3

BACKGROUND

The generation of elastic waves by remote transient heating was first studied by Danilovskaya in 1950 [5], Michaels in 1960 [6], and White in 1963 [7]. Scruby et al. [21] invoked a model describing the generation process as equivalent dipole forces embedded in the sample surface. McDonald [8] developed a three-dimensional formulation utilizing Hankel-Laplace transform inversion based on generalized thermoelasticity theory to model the acoustic wave. Spicer [9] developed the theory of laser generation in anisotropic materials using the theories of electromagnetism and thermoelasticity.

Most work in the laser ultrasonics has been performed on metals. However, there have been several studies of LU as a technique to inspect composites. Papers by Wetsel [10] and [11], and Scudder et al [12] show attempts to theoretically model the generation process in simplified composite systems. Paul et al. [13] used theoretical modeling to measure the elastic constants of carbon fiber-reinforced carbon. Corbel et al [14] displayed experimental laser-generated ultrasonic directivity patterns (plots amplitude of sound waves as a function of angle) of carbon/epoxy laminates as detected by contact transducer and optical heterodyne interferometer. Dubois et al. [15] measured optical absorption of graphite/epoxy laminates as a function of laser wavelength. If choices in laser wavelength are available, one can use this data to optimize the wavelength to obtain optimum absorption and reflection for the generation and detection systems, respectively. Unfortunately, the study was conducted using laser wavelengths much longer than those considered here.

The challenge of laser generation is to provide as much laser power as possible without vaporizing surface material, a process known as ablation. Different methods have been tried that spread the laser energy out over a larger area, such as using an array of sources or holographic schemes (see Section 4.1). These usually result in a focused sound wave, but diminish the amount of spatial resolution of the system.

The more complex challenge in applying laser ultrasonics to composites lies in detecting the wave once it has travelled through the material. Common detection methods use the sample as one mirror of an interferometer. System sensitivity depends on the reflectivity of the sample surface. The surface of unpainted polymer/graphite composites is generally absorbent of visible light, providing little backscatter for interferometry. This obstacle may be overcome by applying a surface coating to increase reflectivity, but in certain cases this may not be an available option. The optical smoothness also poses a problem. Compared to metals, composites have more surface roughness, hence scattering light more diffusely. As a result, speckle interferometry, which relies on the coherence of the collected light, is more difficult to achieve. As discussed before, this problem is partially alleviated by using a CFP interferometer. The difficulty of detection can also be lessened by using more powerful continuous-wave lasers. For CFP-based detection, system sensitivity is directly proportional to laser intensity.

There are only limited articles available describing the laser detection of ultrasonic waves in composites. Tittman et al. [16] present a C-scan on graphite/epoxy with an artificially placed flaw using a CFP-based detection system similar to the one used in this research. In 1988, Monchalin et al. [17] performed pulse-echo C-scans on graphite/epoxy plates showing flaw locations and depths. Recently, papers by Ringermacher et al. [18] and McKie et al. [19] have discussed the practical considerations of non-contact scanning of composite components.

Chapter 4

ULTRASONIC WAVE GENERATION BY PULSED LASER 4.1 Generation in the Termoelastic Regime When a laser pulse of moderate energy strikes an opaque material, part of the pulse is reflected and part is absorbed. The absorbed light energy is converted to thermal energy on the time scale of picoseconds [9], causing a local thermoelastic expansion of material near the impact point. The rapid expansion creates an ultrasonic pulse which travels through the material. The laser-generated expansion creates several wave types which can be classified as follows: a longitudinal or compression wave, a transverse or shear wave, and surface acoustic waves which can be either Rayleigh (for thicker plates) or Lamb or plate (for thinner plates) waves.

In a longitudinal wave, the oscillations occur in the direction of propagation [20]. It has the highest velocity of the wave types and can be transmitted in gas, liquid and solid mediums. In a transverse wave, oscillation occurs at right angles to the direction of propagation. Its velocity is approximately half of the longitudinal velocity and is only transmitted in solid mediums. Rayleigh waves have velocities similar to transverse waves but decrease substantially with increasing depth into the solid. Lamb waves are produced when the thickness of the solid is small enough such that the Rayleigh waves become distorted. Surface acoustic waves form as a result of interaction of longitudinal and transverse wave modes. The work presented here primarily made use of longitudinal waves.

The efficiency of conversion from laser light to an acoustic wave depends on many factors, including surface reflectivity for the specified laser wavelength [15], temporal shape and duration of the laser pulse, energy of the laser pulse, and the surface area the laser spot covers. Given that the choice of laser is usually governed by economical constraints, the flexibility in laser generation of acoustic waves mainly lies in the laser energy and how it is distributed on the surface of the target material. The upper limit of purely thermoelastic generation is reached when surface vaporization occurs. The laser intensity at this point is referred to as the ablation threshold. Either increasing the laser energy, or decreasing the surface area covered by the pulse, increases the intensity. The proportionality of laser intensity and acoustic amplitude has been demonstrated in both theory [7] and experiment [22], [23].

Many schemes have been proposed to increase the efficiency of laser ultrasonic generation by spreading out the laser energy over a larger area. The use of a larger laser spot size allows the material to absorb more of the laser energy without surpassing the ablation threshold. The influence of laser energy distribution on efficiency of laser-generated ultrasound has been studied by Gonthier et al [24]. Laser array sources have been implemented and described by Wagner et al. [25], Yang et al. [26], Noroy et al. [27], and Steckenrider [28]. Gutfeld et al. [29] discussed a holographic fringe generating spot. Splitting a beam temporally by rapidly Q-switching a pulsed laser has also been shown to be an effective means of spreading the pulse power out [30]. If a smaller spot size is required, the energy of the laser beam can be reduced by inserting beam attenuators (partially reflecting mirrors which divert a portion of the energy to beam dumps) or by reducing the amount of voltage supplied to the flash pump of the laser [22]. In the research presented here, the geometry of the generating laser surface area is a simple circular spot.

4.2 Generation in the Ablation Regime

When certain laser intensities are exceeded, the laser pulse vaporizes surface material. A dense high-temperature plasma, caused by the rapid heating and ionization of the material, is formed just above the sample. According to J. C. Miller [31], Electromagnetic energy is converted to electronic, thermal, chemical and mechanical energy at the solid interface. The ejected material may include neutral atoms and molecules, positive and negative ions, clusters, electrons, and photons. The generated plasma may have temperatures of thousands of degrees. Of necessity a multidisciplinary problem, the mechanism of laser ablation is still being studied and debated.

These processes have been shown to create an additional acoustic wave the ablatic wave, in the host material. Dyer et al. [32] used wide band polyvinylidenefluoride film piezoelectric transducers to detect combined thermoelastic/ablatic waveforms in 12 μm thick polymethymethacrylate films. Caron et al. [1], using laser ultrasonics, were the first to detect this phenomenon in composites.

The principles concerning the consequences of ablation in laser ultrasonics have been based on the ablation of aluminum. Hutchins et al. [33] displayed the agreement of empirical ablative directivity patterns with theoretical patterns based on a normal force model. This is the reasoning behind the prevailing theory that pressures associated with ablation are the primary generating mechanism of the ablatic wave. In fact, Palmer [34] has recently demonstrated that by directing the laser at a dummy target, the ablation shock wave can impart its momentum on the actual target to create an ultrasonic pulse. Currently there is no direct evidence suggesting this is the generation means of the ablatic wave in composites.

Three possibilities exist for the composition of the ablated particles from a composite. The particles could result from the polymer, the graphite fibers, or a combination of the two. There is a good deal of interest in ultraviolet laser ablation of polymers ([31], [32], and [35]) for the purpose of laser etching. A review article by Srinivasan [36] includes excellent photographs of this reaction. Laser ablation in graphite materials has been studied as a method of producing diamond-like films [37]. However, these studies take place in an atmosphere mainly composed of argon gas, and not air. No formal study of the ablation effects on composites has been found.

Chapter 5

CONFOCAL FABRY-PEROT BASED DETECTION

A noncontact detection system using a frequency-stabilized confocal Fabry-Perot (CFP) interferometer has been developed to receive the ultrasonic waveforms. Continuous-wave laser light is reflected off the surface. The light is Doppler-shifted by the movement of the surface resulting from the ultrasonic wave. By gathering the light in the interferometer, the frequency shift is converted into a proportional change in laser-light intensity leaving the CFP etalon [38]. A photodetector converts the intensity change, upon either transmission or reflection of the laser light through the etalon, into an electrical signal suitable for processing. Hence, the system detects a signal that is proportional to the sample surface velocity.

Figure 2:
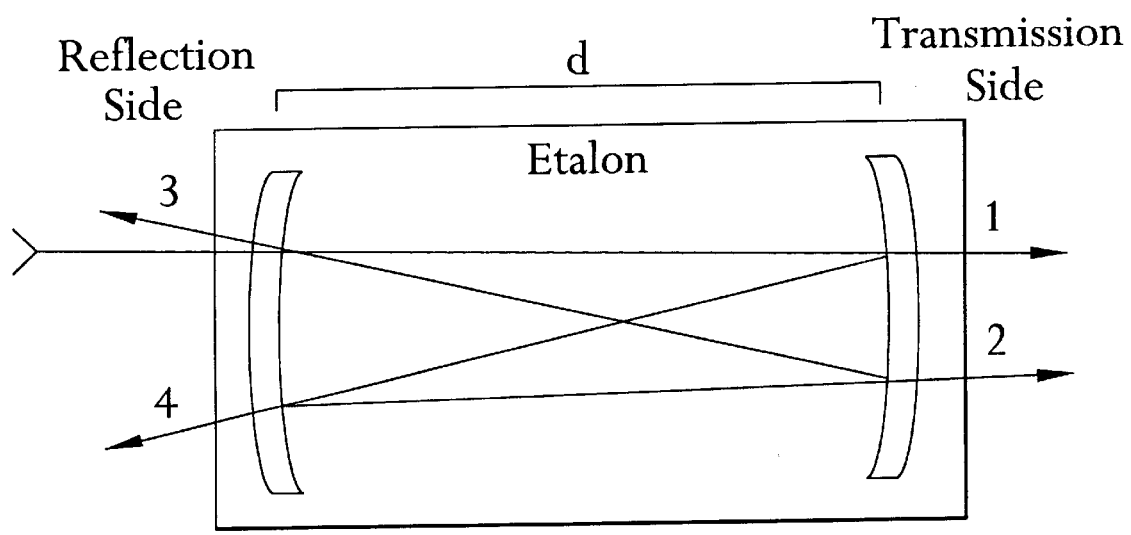
FIG. 2  Schematic of path of a light ray incident on a confocal Fabry Prot interferometer. The etalon consists of two partially reflecting spherical mirrors separated by a distance approximately equal to their focal lengths. In this configuration, one entrance ray produces four exit rays, numbered by convention [42] as shown.

The CFP interferometer consists of two similar opposing spherical mirrors separated by a distance approximately equal to their common focal distance. The mirrors are partially reflecting, allowing rays of light to enter and leave the chamber. In this configuration, shown in FIG. 2, a single off-axis ray retraces the original path after four reflections. Each multiple reflection interferes with the previous reflections, producing an interference pattern sensitive to the frequency of light. Both the transmitted light (rays 1 and 2) and reflected light (rays 3 and 4) can be used to derive the ultrasonic signal. The interferometer is equally sensitive to changes in separation and light frequency, as will be seen in Equation 5.17. Mounting one mirror on a piezoelectric translator enables the etalon to be locked in a position where it is especially sensitive to slight changes in frequency. In our system a servo circuit coupled to a reference photodetector provides the stabilization at frequencies up to tens of kilohertz, allowing passage of megahertz frequencies.

CFP-based detection is described by intensity transfer functions which govern the passage of each ray of light through the etalon [39]. The Doppler-shifted frequency enters as a modulation from the operating frequency at which the cavity is locked. The resulting intensity for that ray is found by extracting the real component of the transfer function.

This chapter details some theoretical aspects of CFP-based detection of ultrasound. Section 5.1 derives the main components of the laser field which are affected by the ultrasonic surface disturbance. In Sections 5.2.2 and 5.3.1, certain parameters, those involving the operation of the CFP-based system as a method for ultrasonic detection in transmission and reflection mode, respectively, are derived. The experimental operating frequencies $v_0$ are derived for each. Sections 5.2.3 and 5.3.2 give the complex transfer functions provide the frequency responses of the system. Section 5.4 shows experimental waveforms captured in each CFP operation mode, and Section 5.5 described some of the advantages CFP-based detection has over other types of interferometers.

5.1 Modulation of the Laser Electric Field by Ultrasound

Theoretical analysis of the CFP-based detection system begins with deducing the effect of an ultrasonic surface displacement on the reflected laser light. The ultrasonic enters the calculation as an disturbance in the laser electric field. The Poynting vector, defined as $$S = E \times H \tag{5.1}$$

where H is the accompanying magnetic field, connects the laser intensity to the electric field. The intensity is the time average of the Poynting vector, or $$I = \langle |S| \rangle_t = \frac{\varepsilon \langle |E|^2 \rangle_t}{2n} = \frac{\varepsilon v_i}{2n} \int_0^{1/v_i} |E|^2 dt \tag{5.2}$$

where $\varepsilon$ and n are the dielectric constant and index of refraction, respectively, of the medium [40].

The cw laser light is represented as a plane wave of the form $$E_i = E_0 e^{i(kz - \omega t + \Psi)} = E_o e^{i\Psi} e^{2\pi i \left(\frac{zv}{c} - vt\right)} \tag{5.3}$$

where $E_0$ is the electric field amplitude component of the reflected light, and $\psi$ is a phase constant. The field reflected from a moving surface can be calculated by relativistically changing the frame of reference to that of the moving surface. The new electric field is $$E_i' = E_0 e^{i\Psi} e^{2\pi i \left(\frac{z'v'}{c} - v't'\right)} \tag{5.4}$$

where $$z' = \gamma(z + ut)$$

$$v' = \gamma v(1 + u/c)$$

$$t' = \gamma(t - uz/c^2) \tag{5.5}$$

are the Lorentz transformations for a moving surface of velocity u and $$\gamma \equiv \frac{1}{\sqrt{1 - \frac{u^2}{c^2}}}. \tag{5.6}$$

Since u<<c, Equation 5.5 can be approximated to first order. For example $$v' \approx v\left(1 + \frac{u}{c}\right)\left(1 - \frac{u^2}{2c^2}\right) \tag{5.7}$$

$$\approx v\left(1 + \frac{u}{c}\right) \equiv v_i + \delta v$$

where $\delta v$ is the Doppler-shift of the laser frequency. For reflection from a moving surface, this is approximately [41]

$$\delta v = \frac{2uv_i}{c}. \tag{5.8}$$

Displacement and time can also be represented as $$z' = z_i + \delta z$$

$$t' = t_i + \delta t. \tag{5.9}$$

Substitution into Equation 5.4 yields $$E_i' = E_0 e^{i\Psi} \exp\left[2\pi i (v + \delta v)\left(\frac{z_i + deltaz}{c} - (t + \delta t)\right)\right]. \tag{5.10}$$

After multiplying the factors and eliminating the higher order terms, this becomes $$E_i' = E_0 e^{i\Psi} e^{2\pi i (v_i z_i/c - vt)} \exp\left[2\pi i\left(\frac{v_i \delta z}{c} + \frac{z_i \delta v}{c} - (v\delta t + t\delta v)\right)\right]. \tag{5.11}$$

Equation 5.11 shows discrepancies when compared to analysis presented by Dewey et al. [42]. In that report, only the surface displacement is affected by the moving surface. There is no consideration for the Doppler-shifted frequency or wavelength in the subsequent calculation. Following their derivation, surface displacement is defined as $$z(t) = z_i + 2\delta(t), \tag{5.12}$$

where $z_i$ is as defined above, and $\delta(t)$ is the ultrasonic surface displacement having the form $$\delta(t) = U \cos(2\pi v_u t + \phi). \tag{5.13}$$

The variables U, $v_u$, and ø are the amplitude, frequency, and phase constant of the surface displacement. Substitution into Equation 5.3 yields $$E_i = \dot{E}_o e^{i\varphi} \exp\left[2\pi i v_i t - \frac{4\pi i v_i}{c}\delta(t) - \frac{2\pi i v_i}{c} z_0\right]. \tag{5.14}$$

From Equation 5.14, and expression is derived for the laser intensity that is either transmitted or reflected from the CFP interferometer. As shown in later in this chapter, the frequency response of the detection system can be evaluated.

Equations 5.11 and 5.14 are equal if the following condition is applied $$2\delta(t) = \delta z - c\delta t + \frac{\delta v}{v_i}(z_i - ct). \quad (5.15)$$

The frequency dependence has been verified empirically by Monchalin et al. [43]. This may suggest that the second and third terms of Equation 5.15 have a minimal effect on the calculation of the CFP frequency response. With this in mind, the following calculations are based on the analysis presented by Dewey et al. [42].

5.2 CFP-based Detection with the System in Transmission Mode

5.2.1 Experimental Set-up using CFP in Transmission Mode

Figure 3:
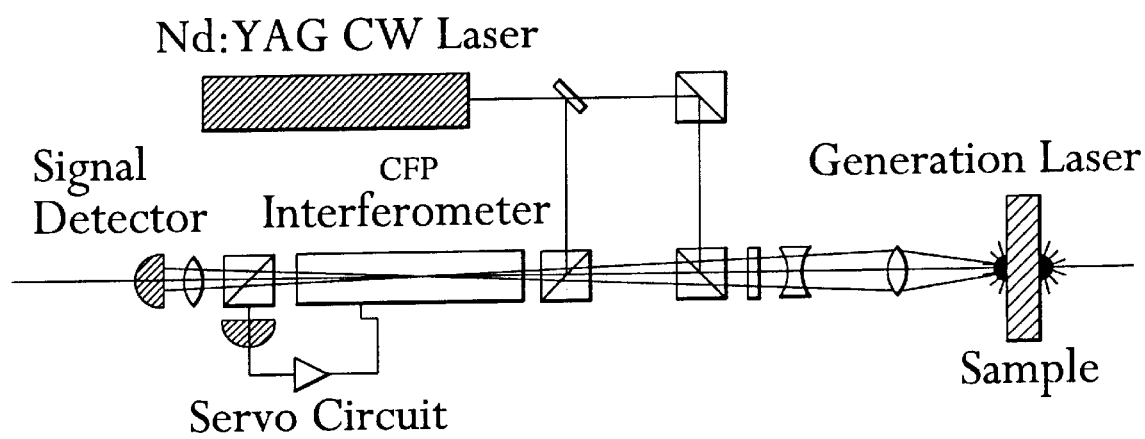
FIG. 3  Diagram of a typical set-up using the CFP in transmission configuration for the detection of ultrasound. A separate reference beam is diverted from the laser and directed via polarizing beam splitters to a second photodetector. The resulting signal is used by the servo circuit to lock the CFP etalon.

A diagram of a typical transmission mode set-up is shown in FIG. 3. A cw Coherent DPSS-532 Nd:YAG laser [44] emits 200 mWatts of 532 nm light The vertically polarized light is directed to the sample using polarizing beam splitters (PBS). Surface reflected light is collected into the Burleigh CFP interferometer [45] using a telescopic lens system. Two passes through the quarter-wave wave plate allows transmission through the PBS. The exiting light is focused onto a fast photodetector, providing the signal for the Tektronics [46] TDS 500 digital oscilloscope. A small portion of the laser light is diverted directly through the CFP etalon. Another PBS diverts this light to a second photodetector, providing a signal for the servo circuit. The servo circuit, based on a design by White and Emmony [47], is connected to a piezo-electric translator mounted to one of the CFP mirrors. This provides active stabilization in the advent of laser frequency drift. The photodetectors have been customized for their specific tasks, based on recommendations from EG&G Optoelectronics [48].

The advantages to working in the transmission mode are the ease of design and set-up. The use of a reference beam to lock the etalon provides an easy locking device without losing much laser power. The disadvantage, as will be shown, is the narrow frequency bandwidth.

5.2.2 Intensity Distribution of Ray 1

To detect the small shift in frequency, the CFP etalon spacing is "locked" at a position which will provide the greatest change in intensity to a change in frequency. From Hernandez [38], the transmission coefficient for ray of type 1 (see FIG. 2) through a CFP is $$t_1(\phi) = \frac{1 - R}{1 - R^2 e^{i\phi}} \quad (5.16)$$

where ø is the phase lag between successive reflections of light $$\phi = \frac{8\pi dv}{c}, \quad (5.17)$$

d is the mirror separation distance, c is the speed of light and R is the reflectivity of the mirrors in the CFP. This can also be expressed as $$t_1(v) = \frac{1 - R}{1 - R^2 e^{isv}} \quad (5.18)$$

where s is defined as $$s \equiv \frac{8\pi d}{c}. \quad (5.19)$$

Figure 4:
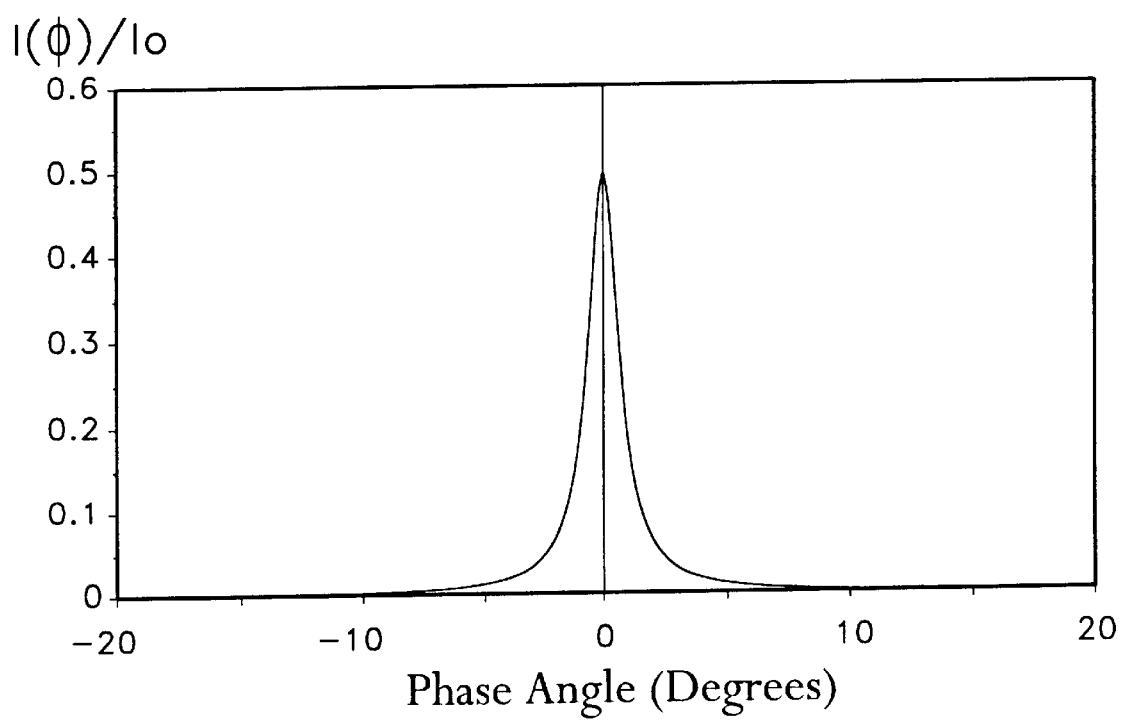
FIG. 4  Graph of intensity distribution of ray 1 as a function of phase angle φ. A change in laser frequency is similar to a change in mirror separation.

The intensity of transmitted light is $$I_1(v) = \frac{(1 - R)^2}{1 - 2R^2 \cos sv + R^4} \quad (5.20)$$

shown in FIG. 4. From Equation 5.17, Equation 5.20 is sensitive to either a change of v or d. By controlling the separation distance, one can lock the system to a point on the slope of the intensity distribution which will provide the greatest sensitivity to a change in frequency. This is accomplished by mounting one interferometer mirror onto a piezoelectric translator which is controlled by a servo circuit. The system's effectiveness for detecting ultrasonic waves improves with increasing slope.

To find the most sensitive point for use as the operating frequency, Equation 5.20 is differentiated twice with respect to v and set equal to zero.

$$\frac{\delta I}{\delta v} = \frac{-2R^2 s(1 - R)^2 \sin sv}{(1 - 2R^2 \cos sv + R^4)^2} \quad (5.21)$$

$$\frac{\delta^2 I}{\delta v_o^2} = -2R^2 s^2 (1 - R)^2 \left[ \frac{-4R^2 \sin^2 sv_o}{(1 - 2R^2 \cos sv_o + R^4)^3} + \frac{\cos sv_o}{(1 - 2R^2 \cos sv_o + R^4)^2} \right] = 0$$

Solving for $\cos sv_o$, $$2R^2 \cos^2 sv_o + (1 + R^4)\cos sv_o - 4R^2 = 0 \quad (5.22)$$

$$\cos sv_o = \frac{-(1 + R^4) + \sqrt{(1 + R^4)^2 + 4(4R^2)(2(R^2))}}{4R^2}$$

$$= \frac{-(1 + R^4) + \sqrt{1 + 34R^4 + R^8}}{4R^2} \approx 0.999967$$

for R=0.993. This yields $$sv_o \approx 8.12 \times 10^{-3} + 2\pi n). \quad (5.23)$$

where n is an integer. Thus $$v_o = \frac{c}{8\pi d}(8.12 \times 10^{-3} + 2\pi n). \quad (5.24)$$

A plot of Equation 5.20 as a function of frequency shows that this point is unreasonably close to the top of the peak. From practical experience, the CFP servo circuit would have trouble locking to such a point.

A better approximation to operating conditions is to take the half-point on the intensity slope. This is found by taking $$I(\phi_{hp}) = \frac{1}{2}(I_{min} + I_{max}) \quad (5.25)$$

-continued $$\frac{(1-R)^2}{1-2R^2\cos\phi_{hp}+R^4} = \frac{(1-R)^2}{2(1+R^2)^2} + \frac{(1-R)^2}{2(1-R^2)^2}$$

$$= \frac{1+R^4}{(1+R)^2(1+R^2)^2}$$

$$1 - 2R^2\cos\phi_{hp} + R^4 = \frac{(1+R)^2(1+R^2)^2(1-R)^2}{1+R^4}$$

$$\cos\phi_{hp} = \frac{2R^2}{1+R^4}$$

$$\phi_{hp} = sv_o = 0.0141 + 2\pi n$$

for R=0.993. Then from Equation 5.19, the operating frequency is $$v_o = \frac{c}{8\pi d}(1.41 \times 10^{-2} + 2\pi n). \tag{5.26}$$

Since $v_0$ enters the calculation only as an argument of sine or cosine, the $2\pi n$ can be neglected. For a given separation distance d=0.5 m, the resulting operating frequency $v_0$=336 kHz.

5.2.3 Derivation of CFP Transfer Function for Ray 1

Monchalin and Heon [43] have experimentally verified that a suitable transfer function describing the transmission of ray 1 is given by $$\overline{S}_1 = i[t_1(sv_0)t_1(-sv_0-sv) - t_1(-sv_0)t_1(sv_0-sv)] \tag{5.27}$$

where v is the ultrasonic frequency and $t_1(v)$ is defined by Equation 5.18. A full derivation is shown in Dewhurst and Shan [42]. This can be separated into its real and imaginary components $$t_1(sv) = t_{1r}(sv) + it_{1i}(sv) \tag{5.28}$$

where $$t_{1r}(sv) \equiv \frac{(1-R)(1-R^2\cos sv)}{1-2R^2\cos sv + R^4} \tag{5.29}$$

and $$t_{1i}(sv) \equiv \frac{(1-R)(R^2\sin sv)}{1-2R^2\cos sv + R^4}$$

Upon multiplication, the transfer function becomes $$\overline{S}_1 = [t_{1r}(sv_o)t_{1i}(sv_o - sv) - t_{1i}(sv_o)t_{1r}(sv_o - sv) - \tag{5.30}$$

$$t_{1i}(sv_o)t_{1r}(sv_o + sv) + t_{1r}(sv_o)t_{1i}(sv_o + sv)] +$$

$$i[t_{1r}(sv_o)t_{1r}(sv_o + sv) + t_i(sv_o)t_i(sv_o + sv) -$$

$$t_{1r}(sv_o)t_{1r}(sv_o - sv) + t_{1i}(sv_o)t_{1i}(sv_o - sv)].$$

A quick check shows $\overline{S}_1$=0 when v=0. The amplitude of the transfer function for an incoming light beam is $$S_1(v) = (\overline{S}_1\overline{S}_1^*)^{1/2}. \tag{5.31}$$

Figure 5:
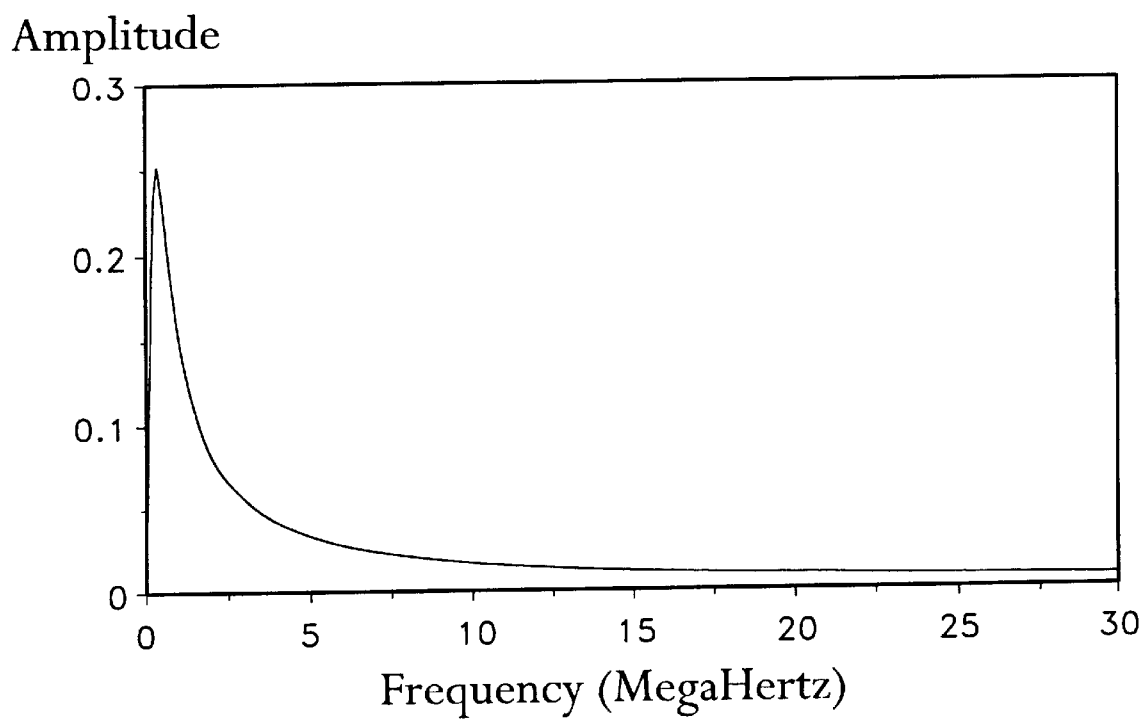
FIG. 5  Graph of the frequency dependence of a CFP-based system in transmission mode. As a result of the narrow frequency bandwidth, the system operates like an optical passband filter.

A plot of $S_1(v)$, shown in FIG. 5, reveals that the frequency dependence of the CFP behaves as an optical passband filter. The total intensity output is $$I_1 = I_o\left[|t_1(sv_o)|^2 + \frac{4\pi U}{\lambda}S_1(sv)\cos(2\pi svt + \Phi - \theta_1(sv))\right] \tag{5.32}$$

where $I_0$ is the incoming laser intensity, U is the maximum surface displacement, $\lambda$ is the laser wavelength, $\Phi$ is a constant phase factor, and $\theta$ is the phase response to the ultrasonic displacement for ray 1 [42].

If the maximum of Equation 5.31 can be identified, it may be possible to construct the CFP to maximize a specific frequency, or to optically scan the frequency distribution of a sound wave by large-scale adjustments in the etalon spacing. The simplest way to achieve this is to plot out the first derivative of Equation 5.31. The frequency which results in the greatest amplitude is 388 kHz for $sv_0$=8.12× $10^{-3}$ and 480 kHz for $sv_0$=1.41×$10^{-2}$. The pattern repeats every 75 MHz.

5.2.4 Intensity Distribution of Ray 2

The second transmission ray goes through two more reflections in the CFP etalon. Thus, $t_2(sv)=Rt_1(sv)$. This yields the transfer function [42]

$$\overline{S}_2 = iR^2[t_1(sv_0)t_1(-sv_0-sv) - t_1(-sv_0)t_1(sv_0-sv)] \tag{5.33}$$

Since the intensities add at the output of the CFP, the final transfer function amplitude is $S_{1+2}=(1+R^2)S_1$. By capturing both rays, the signal-to-noise ratio can approximately be doubled. This is easily accomplished using a convex lens at the output of the CFP.

5.3 CFP-based System used in Reflection Mode

5.3.1 Intensity Distribution of Ray 3

Figure 6:
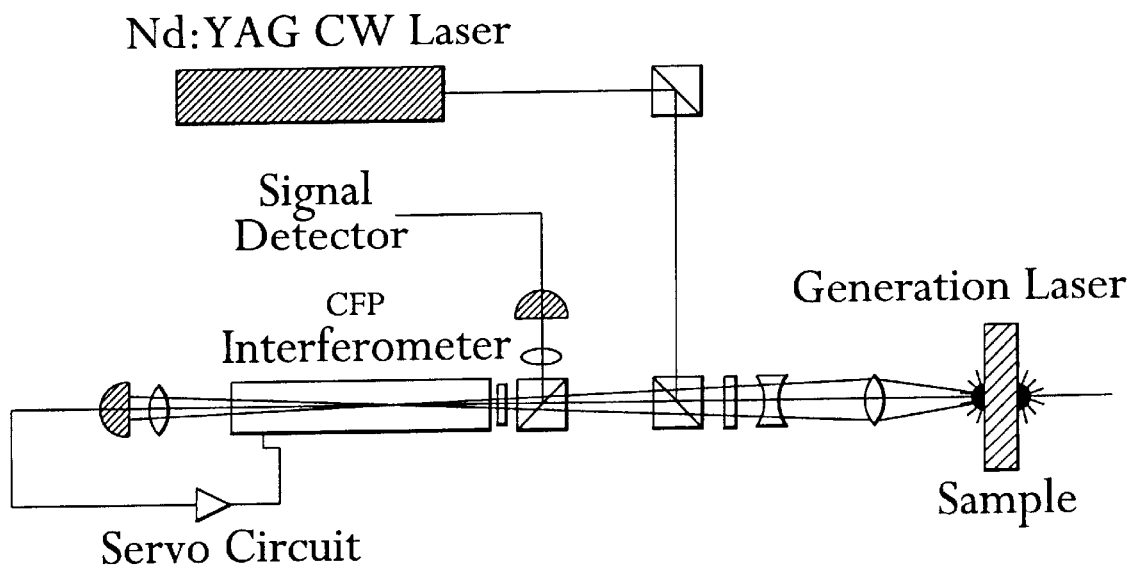
FIG. 6  Diagram of the CFP-based detection system arranged in a reflection configuration. Polarizing beam splitters allow the light reflected from the etalon to provide the ultrasonic signal. Light transmitted through the etalon provides the signal for the servo circuit.

The type 3 ray is defined as one ray of light reflected back from the CFP. The ray can be detected by placing a wave plate immediately in front of the etalon, as shown in FIG. 6. The horizontally polarized light entering the etalon is converted to vertically polarized after two passes through the wave plate. The reflected light is then redirected by the PBS to the signal detector. Transmitted light is used to lock the CFP etalon to a frequency-sensitive position.

The transfer function for this ray [42] is given as $$\overline{S}_3 = i[t_3(sv_0)t_3(-sv_o - sv) - t_3(-sv_o)t_3(sv_0 - sv)] \tag{5.34}$$

where $$t_3(sv) = \frac{\sqrt{R}(1 - Re^{isv})}{1 - R^2 e^{isv}} \tag{5.35}$$

resulting in an intensity of $$I(\phi) = t_3(\phi)t_3^*(\phi) = R\frac{1 - 2R\cos\phi + R^2}{1 - 2R^2\cos\phi + R^4}. \tag{5.36}$$

Figure 7:
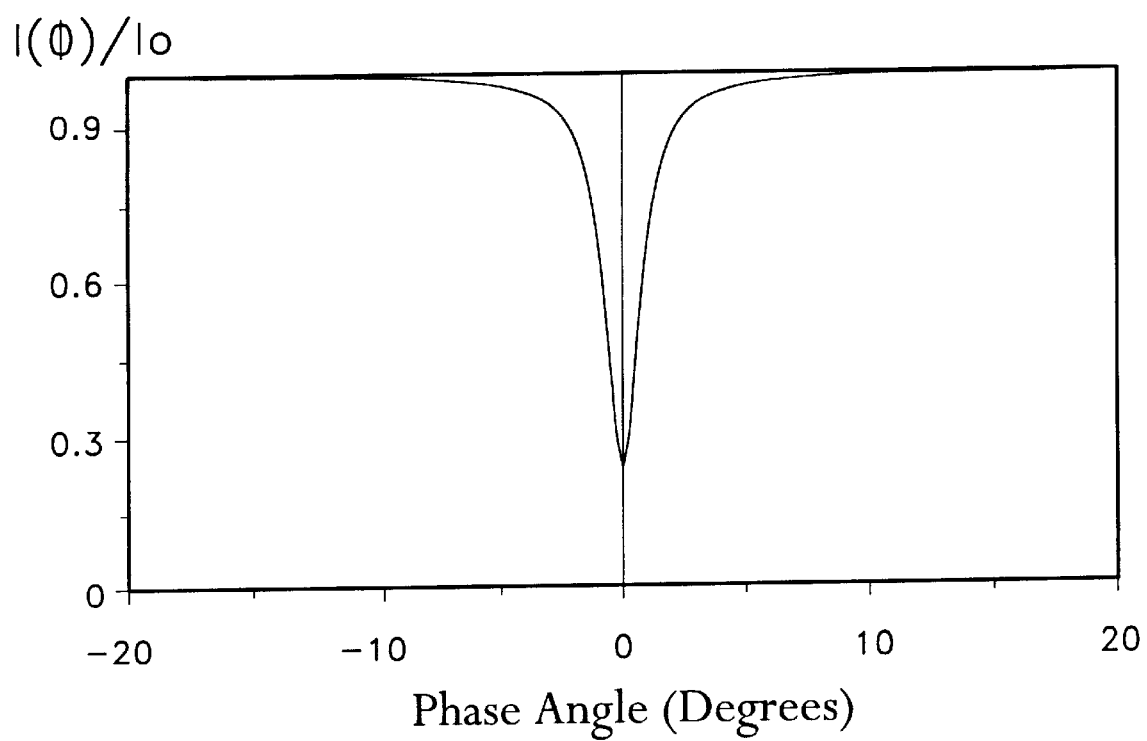
FIG. 7  Graph of intensity distribution of CFP ray 3 as a function of the phase angle φ. A change in laser frequency is similar to a change in mirror separation.

The intensity distribution has the opposite polarity compared to the other three rays, as shown in FIG. 7. The total intensity output is $$I_3 = I_o\left[|t_3(sv_o)|^2 + \frac{4\pi U}{\lambda}S_3(sv)\cos(2\pi svt + \Phi - \theta_1(sv))\right] \tag{5.37}$$

As before, the operating frequency is found by locking the intensity at its halfway point.

$$I(\phi_{hp}) = \frac{R}{2}\left(\frac{1+R^2}{1+R^4} + \frac{1}{(1+R)^2}\right) \approx \frac{5}{6} \quad (5.38)$$

$$= R\frac{1 - 2R\cos\phi + R^2}{1 - 2R^2\cos\phi + R^4}.$$

Solving for cos ø yields $$\cos\phi = \frac{1 + R^2 - \frac{5}{6}(1+R^4)}{2R\left(1 - \frac{5}{6}R\right)} \quad (5.39)$$

resulting in an operating frequency $v_0$ of 614 kHz.

5.3.2 Transfer Function of Ray 3

Substitution of Equation 5.35 into 5.34 yields $$\bar{S}_3 = \quad (5.40)$$

$$iR\left[\frac{1 - Re^{isv_o}}{1 - R^2e^{isv_o}}\frac{1 - Re^{-is(v_o+x)}}{1 - R^2e^{-is(v_o+x)}} - \frac{1 - Re^{-isv_o}}{1 - R^2e^{-isv_o}}\frac{1 - Re^{is(v_o-x)}}{1 - R^2e^{is(v_o-x)}}\right].$$

As before, this can be separated into its real and imaginary components $$t_{3r}(\phi) \equiv \frac{1 + R^3 - R(1+R)\cos\phi}{1 + R^4 - 2R^2\cos\phi} \quad (5.41)$$

$$t_{3i}(\phi) \equiv \frac{R(R-1)\sin\phi}{1 + R^4 - 2R^2\cos\phi}.$$

Then $$\bar{S}_3 = iR[(t_{3r}(sv_o) + it_{3i}(sv_o))(t_{3r}(sv_o + sx) - it_{3i}(sv_o + sx)) - \quad (5.42)$$

$$(t_{3r}(sv_o) - it_{3i}(sv_o))(t_{3r}(sv_o - sx) + it_{3i}(sv_o - sx))] =$$

$$iR[t_{3r}(sv_o)t_{3r}(sv_o + sx) + t_{3i}(sv_o)t_{3i}(sv_o + sx) -$$

$$t_{3r}(sv_o)t_{3r}(sv_o - sx) + t_{3i}(sv_o)t_{3i}(sv_o - sx) +$$

$$i(t_{3i}(sv_o)t_{3r}(sv_o + sx) - t_{3r}(sv_o)t_{3i}(sv_o + sx)) +$$

$$i(t_{3i}(sv_o)t_{3r}(sv_o - sx) - t_{3r}(sv_o)t_{3i}(sv_o - sx))]$$

Figure 8:
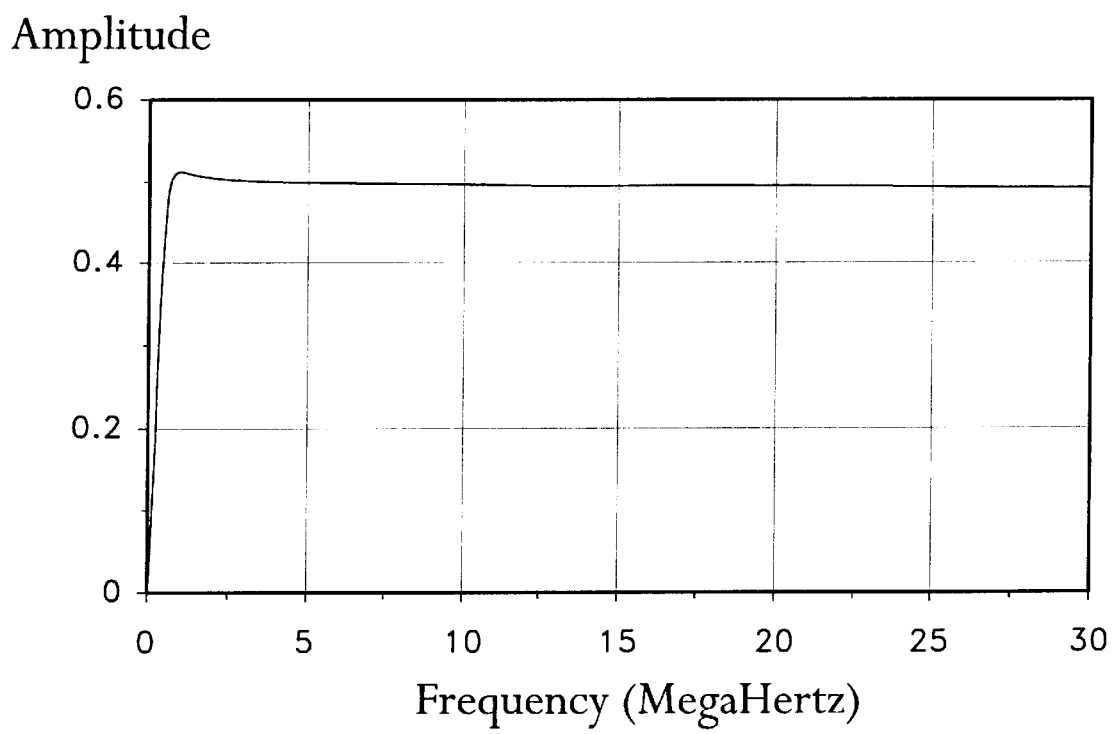
FIG. 8  Graph of frequency dependence for the CFP-based detection system in reflection mode. The system operates like an optical high-pass filter.

As before, the amplitude of the transfer function is $$S_2(v) = \bar{S}_3\bar{S}_3^* \quad (5.43)$$

which is plotted in FIG. 8.

The advantage of working in reflection mode is the greatly improved frequency distribution. Narrow frequency detection can be achieved, if desired, through electronic means with no loss in signal-to-noise performance. Stabilizing the system using surface reflected light and delicate signal detector alignments are the primary disadvantages.

5.3.3 Intensity Distribution of Ray 4

The transfer function for a ray 4 is given by [42]

$$\bar{S}_4 = i[t_4(sv_o)t_4(-sv_o - sv) - t_4(-sv_o)t_4(sv_o - sv)] \quad (5.44)$$

where $$t_4(sv) = \frac{\sqrt{R}(1-R)}{1 - R^2e^{isv}} \quad (5.45)$$

resulting in the same distribution as ray 1 except for the √R factor. Therefore, $S_4=RS_1$. To take advantage of the higher frequencies of the reflection mode, ray 3 must be carefully discerned through alignment of the signal photodetector. Capturing both rays might result in some cancellation effects limiting the size of the signal. Since ray 4 has a similar intensity distribution to ray 1 (see FIG. 4), ray 3 can be discerned by its opposite polarity. A total reflection ultrasonic transfer function can be constructed from $$\bar{S}_{refl} = \bar{S}_3 + \bar{S}_4 \quad (5.46)$$

which provides some flattening of the overshoot of the $\bar{S}_3$ transfer function. However, how one can tell there is an even ratio between the two in actual experiments is uncertain.

5.4 Comparison of the Transmission and Reflection Modes

Figure 9:
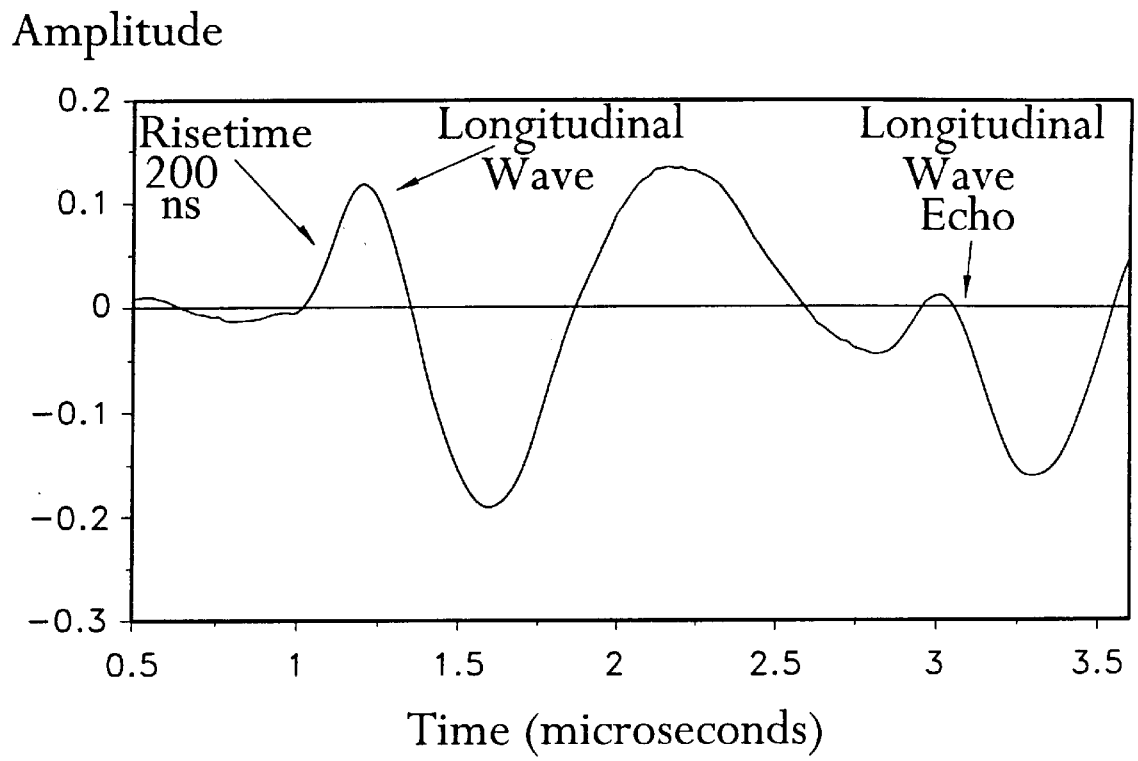
FIG. 9  Graph of an ultrasonic waveform captured in a 2.9 mm thick Graphite/PEEK composite with the CFP-based system in transmission mode. The reduced frequency response provides less resolution of the specific wave types.
Figure 10:
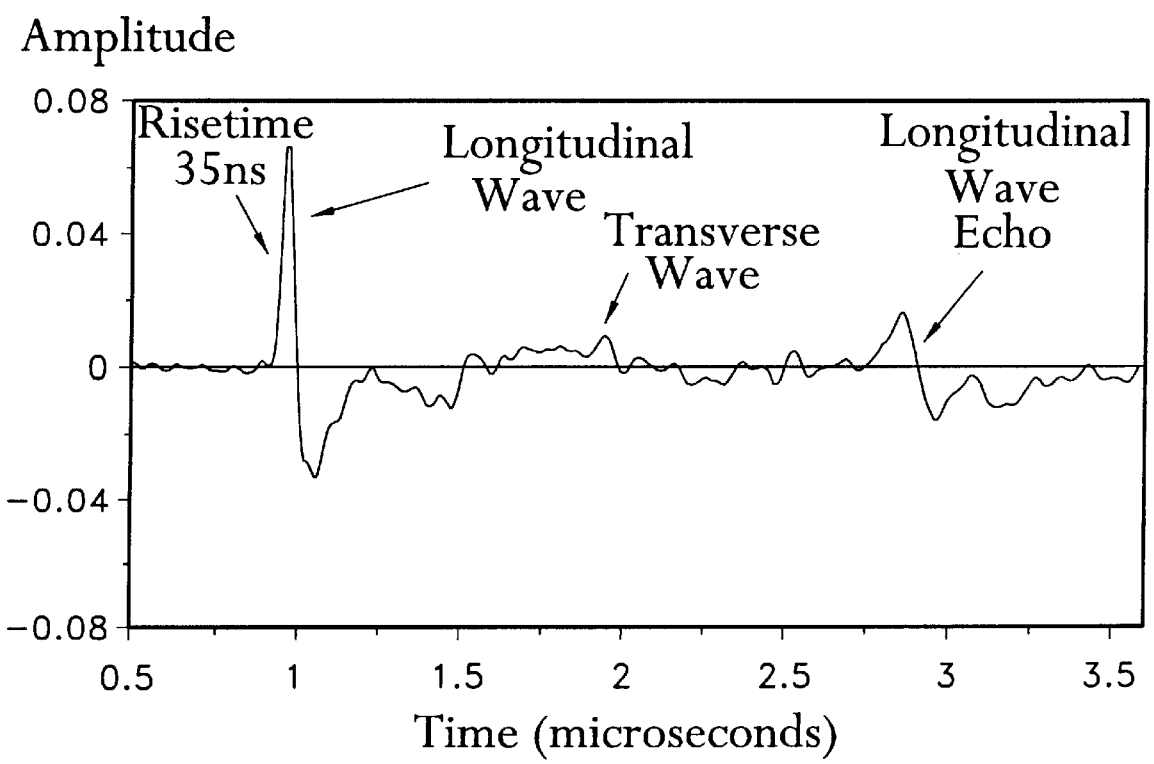
FIG. 10  Graph of an ultrasonic waveform captured in a 2.9 mm thick Graphite/PEEK composite with the CFP-based system in reflection mode. The improved frequency response allows better resolution of the transverse wave and first echo of the longitudinal wave.

FIGS. 9 and 10 display laser-generated waveforms detected in a 2.9 mm thick graphite/PEEK composite plate with the system in transmission and reflection modes, respectively. From FIG. 9, the first longitudinal wave peak can be seen to occur near 900 ns after the firing of the laser pulse. The transverse wave and first longitudinal echo, which can easily be seen in reflection mode, cannot be resolved in transmission mode. The 100 ns acoustic pulse was generated by a 5 ns laser pulse. For an acoustic pulse to be fully resolved in transmission mode, the acoustic pulse must be no shorter than 1 μs. For a transverse wave to be resolved, a typical graphite-fiber composite would have to be greater than about 5 mm thick. Therefore, the transmission mode will suffice if only the first longitudinal wave needs to studied. However, in situations where the shape of the waveform is important, where attenuation is measured, or frequency content is important, the reflection mode is preferable.

Of interest in FIG. 10 is the area between the first longitudinal wave and the transverse wave. As evidence by the area before the longitudinal, this "noise" is well above the system noise levels and is reproducible from shot to shot. It is possible that this results from the acoustic wave scattering off of individual fibers.

5.5 Advantages of CFP-based Detection over other Interferometric Methods

According to Scruby [21], there is little difference in the sensitivity of different types of interferometers when studying materials with optically smooth surfaces. For the study of rough surfaces, typically seen on composite and painted materials, only the CFP and long-path interferometers (LPI) are considered adequate. Reference beam interferometers are considered good for frequencies below 1 MHz but only when a small detection laser spot size can be obtained. Long path interferometers could be used for narrow frequency bands above 100 MHz. However, for frequencies from 1–100 MHz and LPI would be to bulky. In this range the CFP is much more compact and can provide a broader frequency response, especially when used in reflection mode.

Chapter 6

THERMOELASTIC AND ABLATIC WAVES IN GRAPHITE/POLYMER COMPOSITES

This chapter investigates the characteristics and consequences of laser generated waveforms in composites. Section 6.1 explains how the ablation threshold was measured by detecting the light produced from the ablation reaction for the Graphite/PEEK composite. Sections 6.2 and 6.3 display the changes of the waveforms as the ablation threshold is crossed, and how the thermoelastic (TE) and ablatic (AB) coefficients, which represent their relative amplitudes, are evaluated. Section 6.4 displays the directivity pattern of TE longitudinal waves and discusses the problems associated with finding the AB directivity counterparts. Comparisons with various materials are made in Section 6.5.

6.1 Measurement of the Ablation Threshold

Before a quantitative study of the waveform generation mechanisms is discussed, the method used to identify the ablation threshold intensity $I_{ab}$, will be described. $I_{ab}$ is defined as the lowest intensity level at which laser ablation is detected. The method uses a photodetector to capture the light produced during laser ablation. The amplitudes of the resulting signals will be used to compare $I_{ab}$ measured in this fashion to the point at which an ablatic wave is first detected.

Figure 11:
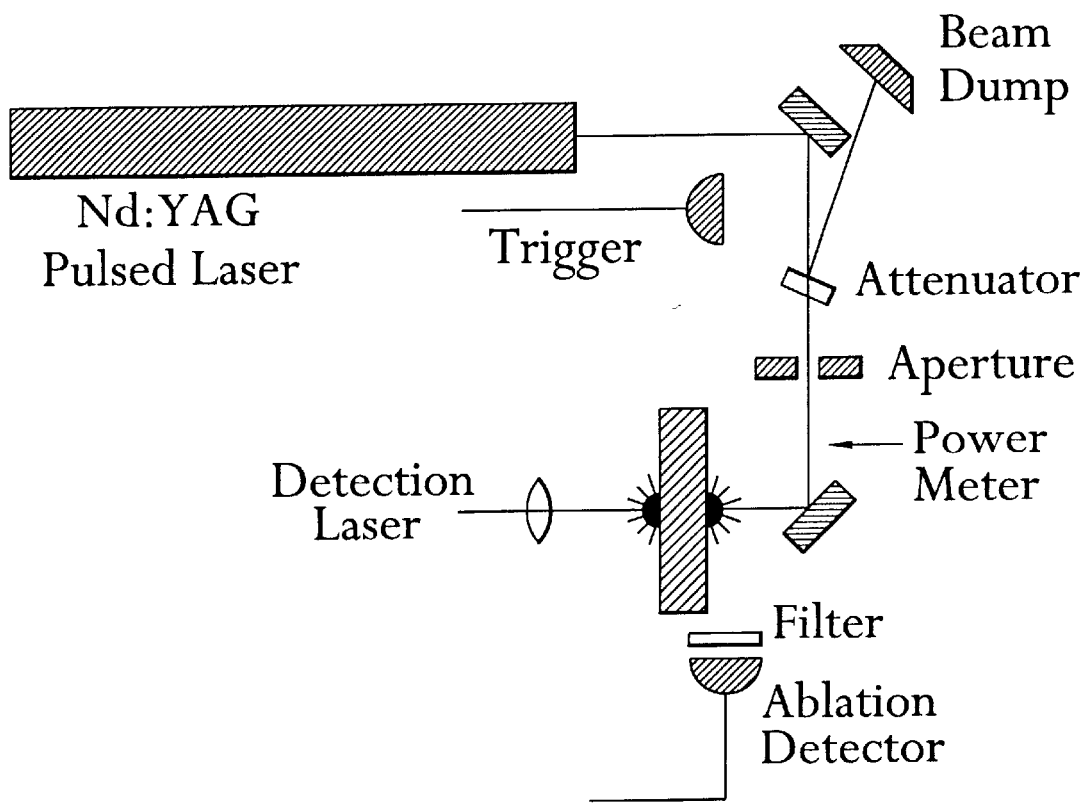
FIG. 11  Diagram of experimental setup for the study of ablatic waves. A customized photodetector captures light produced by the ablation plume. The aperature and attenuator control the intensity range in which the experiments take place.

As shown in FIG. 11, a photodetector was placed perpendicular to the surface of the sample. A Continuum Surelight II Nd:YAG laser [49], producing an infrared pulse with approximately 5 ns width, is directed towards the sample. The sample used here is 2.9 mm quasi-isotropic graphite/PEEK composite. The detector was fitted with a filter to block most of the initial infrared laser light and pass most of the visible light. The purpose is to capture only the light produced by the ablation plume. With this configuration, the signal amplitude from the ablation detector can be measured concurrently with the detection of the laser-generated waveforms.

Figure 12:
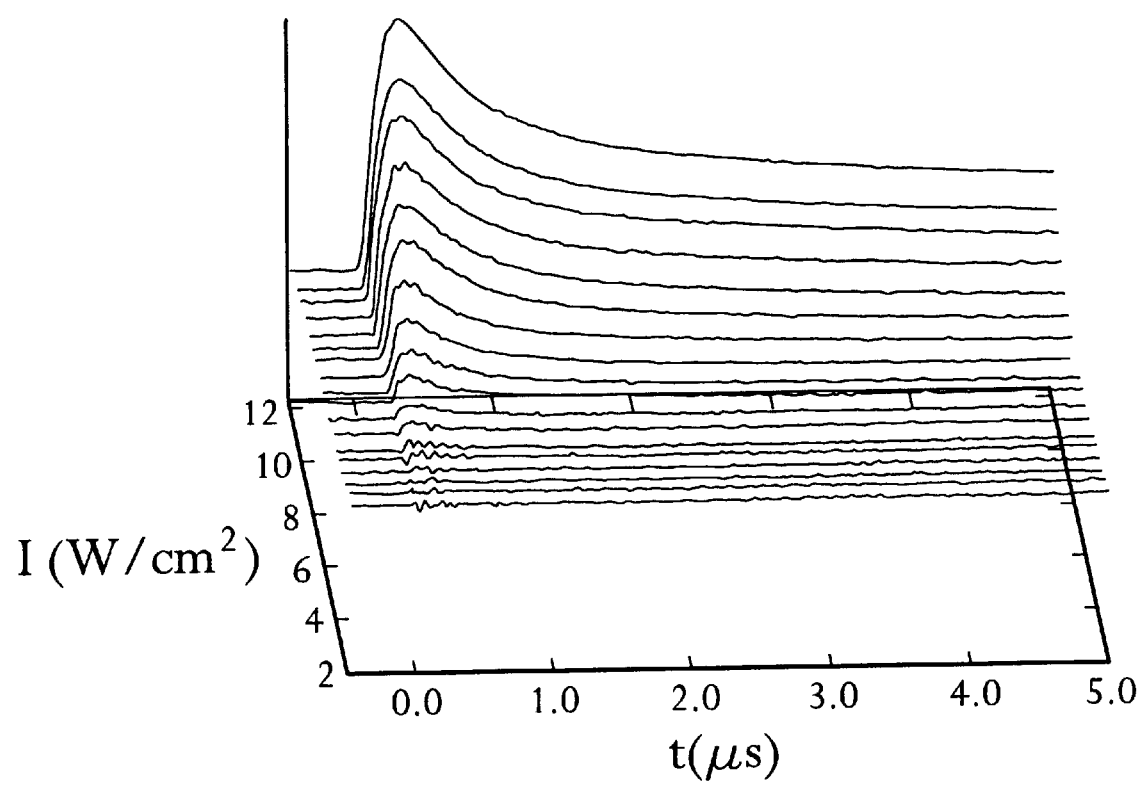
FIG. 12  Graph of photodetector ablation plume signal vs. time, intensity. No detectable signal other than electronic noise, is found below the onset of ablation.
Figure 13:
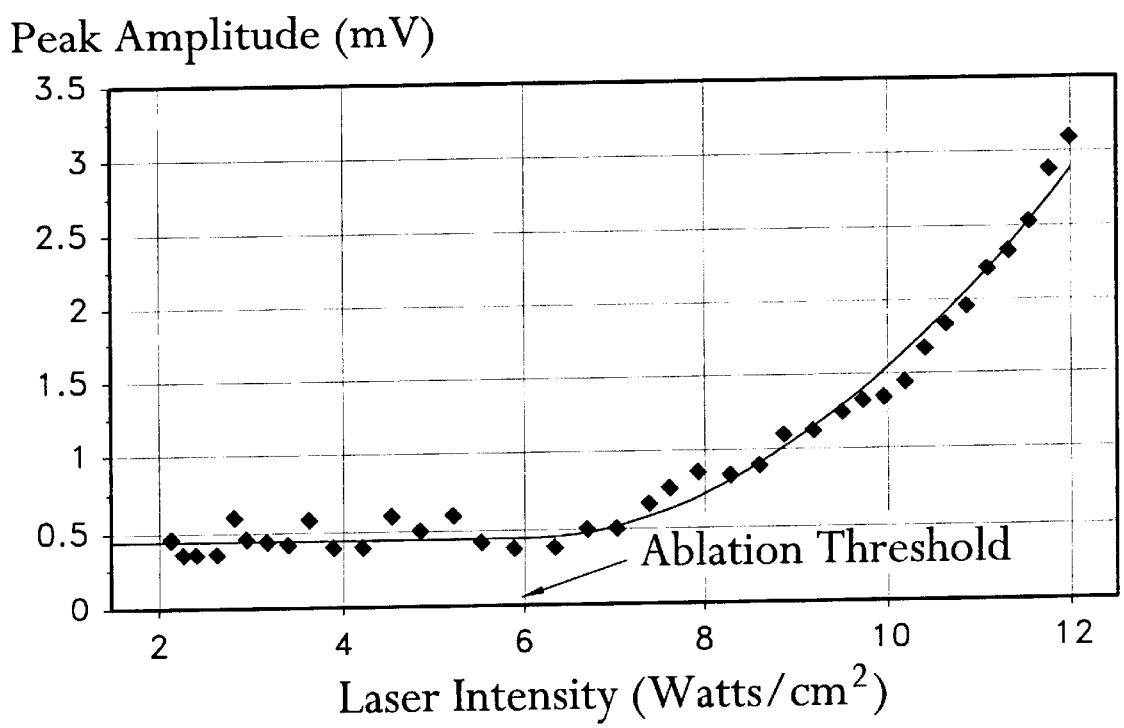
FIG. 13  Graph of maximum plume signal P(I) vs. laser intensity. A parabolic fit was applied to the data to derive a laser ablation threshold intensity of 5.9 W/cm$^2$.

FIG. 12 shows a series of photodetected plume signals plotted as a function of time and source intensity. For intensities below 6 W/cm² the photodetector picked up only a weak trace of the generating beam.[1] Strong signals evolve at higher intensities. The signals have rise times on the order of 120 ns and decay times longer 1 µs. FIG. 13 shows the maximum amplitudes plotted as a function of laser intensity. The results strongly suggest a parabolic dependence of the type $$P(I) = \begin{cases} a & \text{for } I < I_{ab} \\ a + b(I - I_{ab})^2 & \text{for } I \geq I_{ab} \end{cases} \quad (6.1)$$

which was fitted to the data. The best fit occurred with the parameters $I_{ab}$=(5.9±0.2) W/cm², a=−0.610±0.005), and b=(0.46±0.02), providing strong evidence for a well-defined threshold. The use of a quadratic was originally purely empirical, but further study, to be shown in Section 7.1.1, justifies the choice.

[1] The generating laser intensities cited are arrived at by measuring the power with a power meter and dividing by the surface area as measured upon incidence on burn paper. Typical surface area is about 0.8 cm². The experimental values are based on an average of 20 pulses per second with the actual pulses having a time width of about 5 ns. Using these numbers, an experimental intensity of 1.0 W/cm² translates to an intensity of 10 MW/cm² per pulse.

6.2 Generation of Ultrasonic Waves across the Ablation Threshold

In reference [1], the transition from thermoelastic to ablative generation was studied as a function of laser intensity. The experiment was performed in transmission mode, which limited the resolution of the waveforms as described in Section 5.2.2. To test the hypothesis that the detected signals are a superposition of waveforms, a regression fit was performed on each individual waveform at each intensity to separate out the thermoelastic (TE) and ablatic (AB) waves. It was projected that the AB wave occurs later in time than the thermoelastic (TE) wave, which enabled the separation process. However, with the switch to reflection mode and improvements in the photodetector/amplifier system, the effects of the AB wave on the combined waveform can be seen without post-process evaluation.

The basic experiment is similar to that described in reference [1]. The generation setup is shown in FIG. 11. Ultrasonic waves are generated in a 2.9 mm quasi-isotropic graphite/PEEK composite by a 5 ns pulse of infrared light produced by a Nd:YAG laser. The intensity of the pulsed laser was varied by changing the amount of voltage supplied to the laser flash pump. Since changing the flash pump voltage also causes the laser spot size to change, an aperture was inserted to keep the area uniform throughout the experiment. To keep the laser intensity in a useful range, an attenuator was included. The attenuator reflects a portion of the laser energy to a beam dump. The amplitude of the ablation plume signal are also taken at each intensity level. Prior to each experiment, a power meter is inserted, as shown, to calibrate the laser intensity with the digitally displayed flash pump voltage.

Starting from moderate thermoelastic intensities, waveforms were captured and averaged over twenty laser shots to reduce noise in the final data. As the intensity was increased, the amount of averaging was reduced to decrease the amount of surface damage done to the composite. Only three waveforms were averaged at the highest intensity level.

Figure 14:
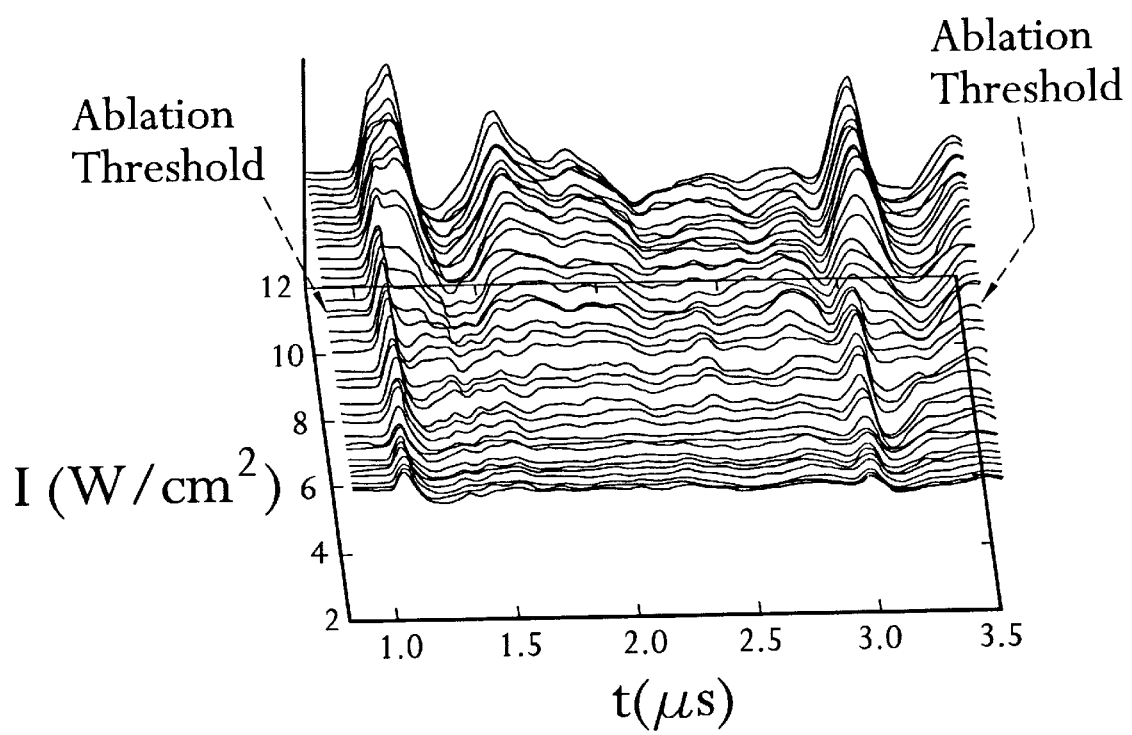
FIG. 14  Graph of laser generated ultrasonic waveforms in 2.9 mm graphite/PEEK sample with average intensity I, and detected with the CFP-based system in a through-transmission configuration. The arrow marks the intensity at which ablation was first optically observed. A delayed longitudinal pulse and a transverse pulse emerge with increasing intensity.

FIG. 14 shown the waveforms plotted as a function of laser intensity. As described in Chapter 5, the plots represent the surface velocities created by the ultrasonic waves. Looking at the lowest wave, generated in the low thermoelastic regime, the first peak corresponds to the arrival of the longitudinal wave. Near the detection epicenter, the transverse wave is not discernible. At 3 µs the echo of the longitudinal wave arrives. The shape of the wave does not change as intensity is increased in the thermoelastic regime (see FIG. 15). However, starting near 6 W/cm², a second peak evolves from the back of the TE wave, attributed to the ablatic wave. At higher intensities, the peaks of the two waves are clearly visible. At the highest tested the AB wave tends to obscure the TE wave. There is also a detectable transverse wave occurring, providing evidence of a separate generation mechanism.

Also note in FIG. 14 that the resolution of the TE and AB peaks in the echo of the combined waveform is not as pronounced. As the waveform travels through more material, the higher frequencies are attenuated more than lower frequencies. This attenuation can also be seen in the purely thermoelastic waveforms, below $I_{ab}$. As a result, the AB wave is much more difficult to discern in thicker samples, or as will be shown later, at significant detection points away from the generation epicenter.

6.3 Thermoelastic and Ablatic Amplitude Dependence on Intensity

Figure 16:
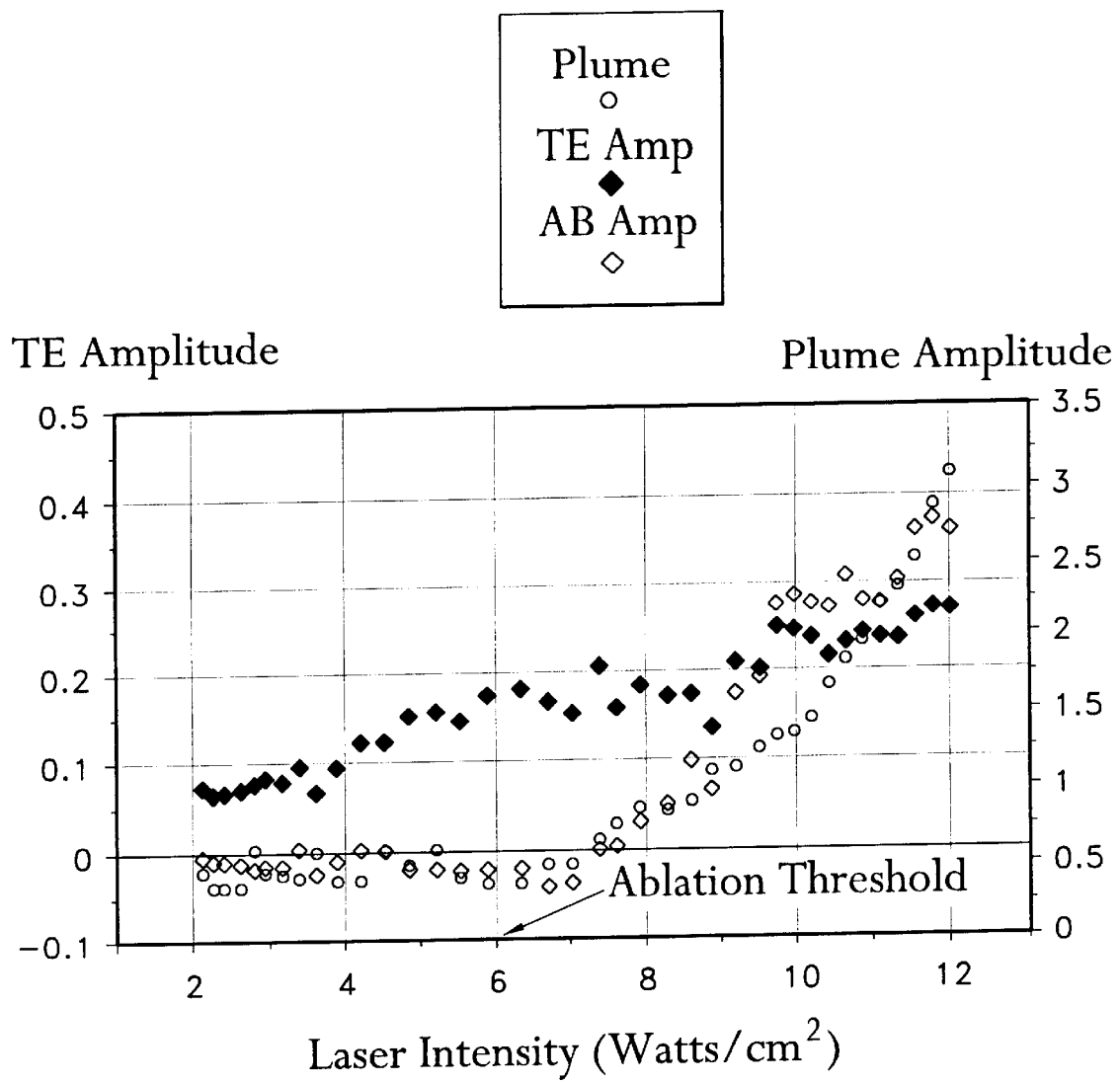
FIG. 16  Graph of amplitudes of the thermoelastic (TE) and ablatic (AB) waves plotted as a function of laser intensity. Amplitudes were measured off the combined waveforms at points which correspond to the maximum of each waveform.

The waveforms of FIG. 14 were analyzed by plotting the magnitude of the first TE and AB maxima as functions of the source intensity. Note that the TE maxima are clearly resolved at low intensities but are obscured by the AB signal at high intensity, and the AB maxima are not resolved at low intensity where there is a strong overlap with the TE signal. Both maxima, when observable, occur at well-defined times, so unresolved amplitudes were obtained by simply (and arbitrarily) taking the magnitude of the signal at the corresponding time. These amplitudes are shown in FIG. 16.

The TE amplitudes are proportional to laser intensity below 6 W/cm². Linear least-squares fits to the low intensity data have intercepts which differ from zero by less than 5% of the average amplitude. The TE plot loses the linearity after the onset of ablation. The AB amplitudes hover within the noise range below the threshold and have a sharp increase following.

Figure 17:
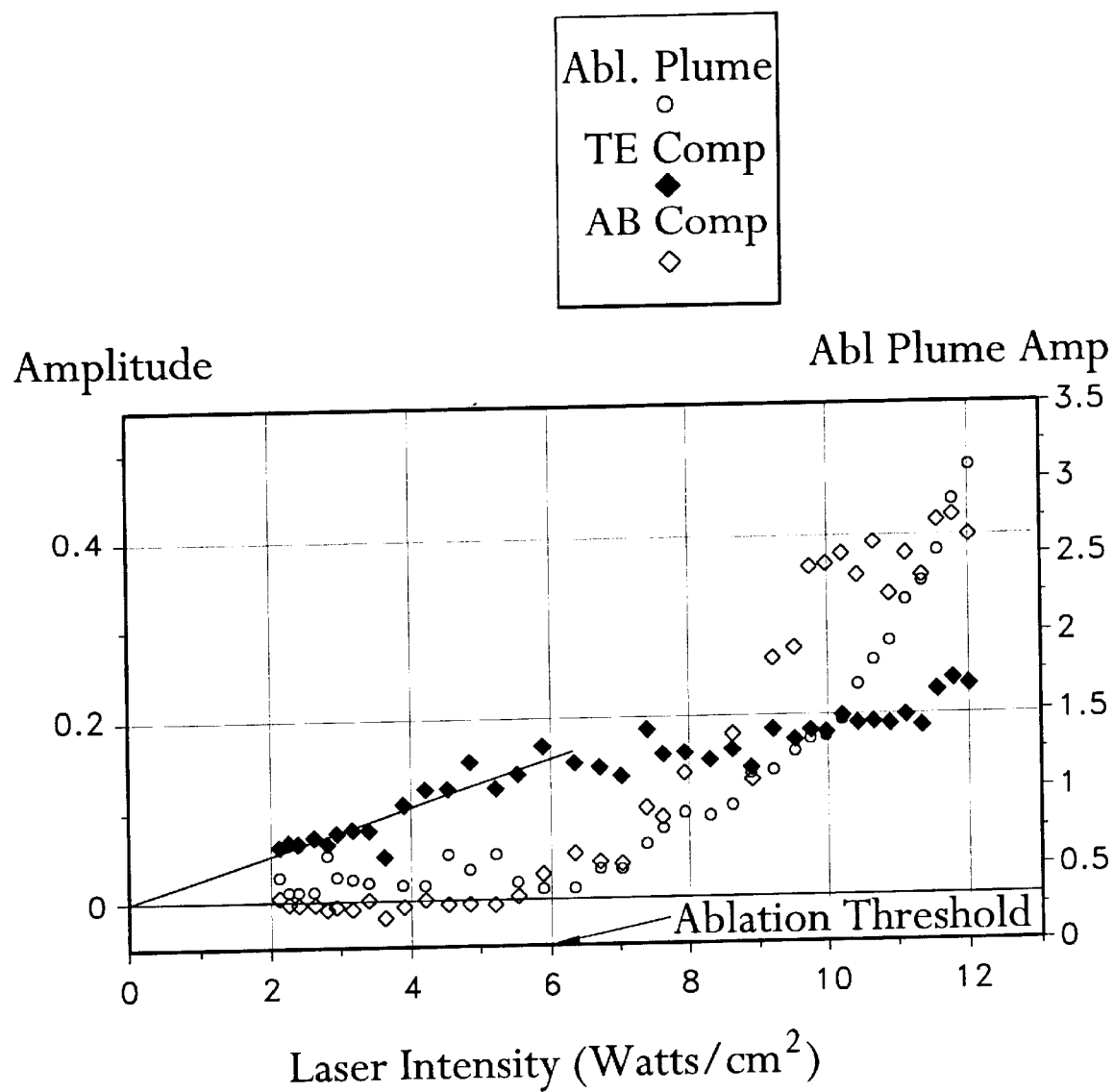
FIG. 17  Graph of separation coefficients C and D of the TE and AB waves, as determined by applying a least-squares fit to the data. The plot shows a threshold occurring near 6 W/cm$^2$.

The waveforms were analyzed by a second method by assuming the waveforms at each intensity level were a superposition of a TE signal Cf(t) and an AB signal Dg(t) where the amplitudes C and D depend on intensity. The basis waveforms f(t) and g(t) are arbitrarily assigned unit amplitude at their first maxima near T=1 $\mu$s. A scaled average of five low intensity waveforms similar to those in FIG. 15 was used for f(t). The following method was used for g(t). A few above-threshold waveforms with clear TE peaks were averaged to get a signal y(t). Then an appropriate multiple of f(t) was subtracted from y(t) to get a waveform with zero amplitude at the first TE peak. The result was then scaled to obtain an AB basis function g(t). The function Cf(t)+Dg(t) was then fit to each of the experimental waveforms to obtain the set of coefficients C(I) and D(I) plotted in FIG. 17.

Figure 15:
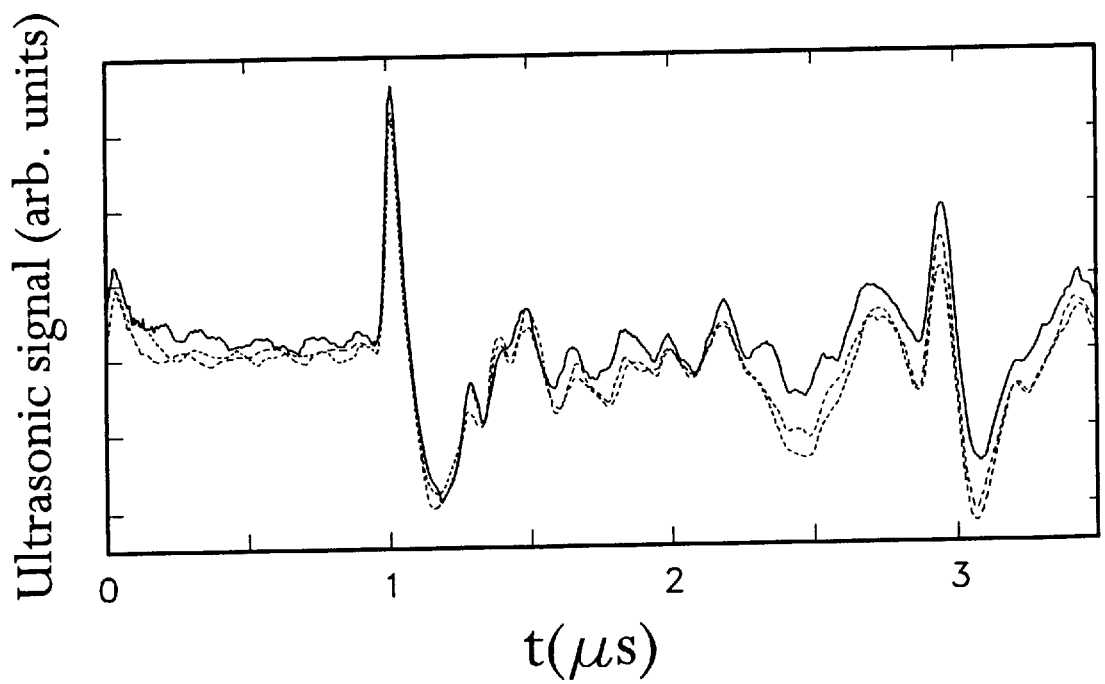
FIG. 15  Graph of three ultrasonic waveforms generated in the thermoelastic regime at t = 0 by low intensity laser pulse incident on 2.9 mm thick quasi-isotropic graphite/PEEK sample.

The results are generally similar to those in FIG. 15, except that this method shows more clearly that the amplitude D of the AB wave has a well-defined threshold $I_{ab}$. For intensities below $I_{ab}$, the AB coefficients are zero within experimental uncertainty and increase rapidly above $I_{ab}$. As before, C is proportional to laser intensity below $I_{ab}$, and fall below the linear extrapolation at higher intensities. This is most likely indicative of interference between the two generation mechanisms.

Figure 18:
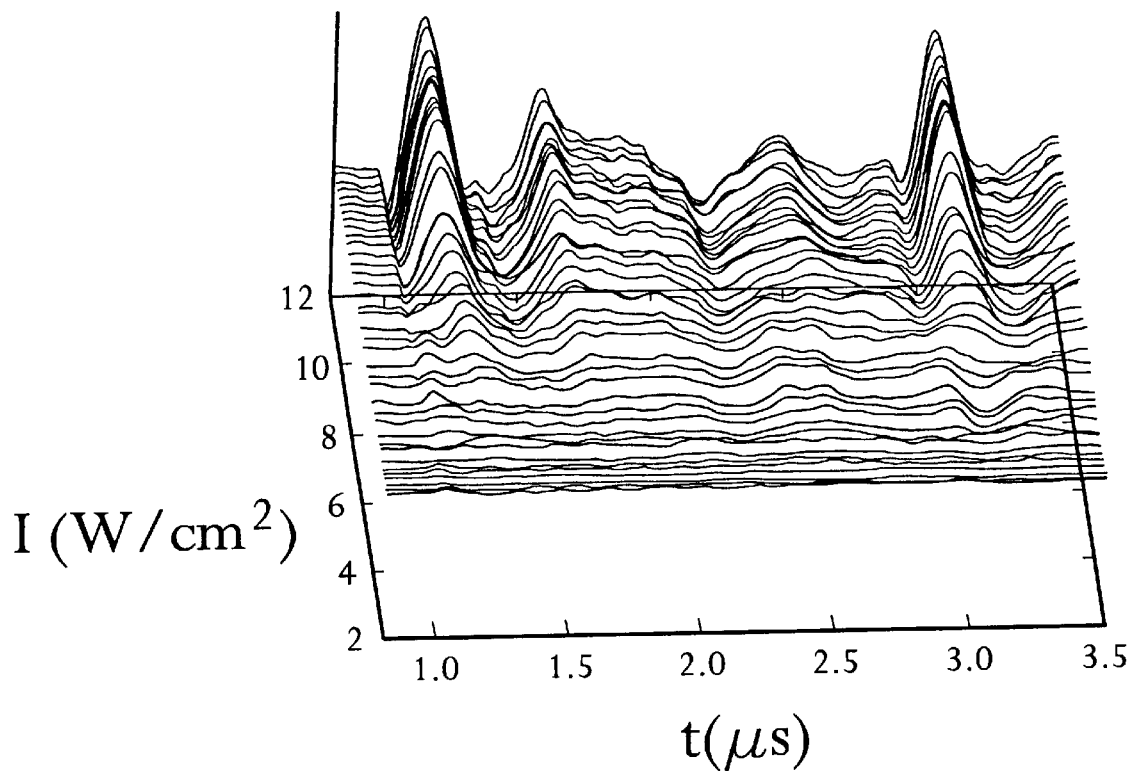
FIG. 18  Graph of separated ablatic waveforms plotted as a function of generating laser intensity. The waveforms were obtained by subtracting a scaled TE waveform from the full experimental expression.

The AB components of the waveforms are displayed separately in FIG. 18. These waveforms, obtained by subtracting $\alpha$If(t) from the full experimental waveforms, show the evolution of the ablatic with increasing intensity. The longitudinal signal and its first echo are clearly resolved, and a transverse peak is also visible. The width of the longitudinal wave is much larger ($\approx$100 ns) than the width of the TE peak shown in FIG. 15 ($\approx$35 ns). As evident in FIG. 12, the process of ablation lasts over a much longer time than the generating laser pulse. It is plausible that the ablative generation process, in comparison with the thermoelastic process, occurs on a longer time scale, and that the AB waveform reaches maximum amplitude at a later time as a consequence.

6.4 Directively Patterns of Thermoelastic and Ablatic Waveforms

The method for establishing the generating mechanism of ablatic waves was put forth by Hutchins et al. [33]. Empirical directively patterns (measuring the sound amplitude as a function of propagation angle) in aluminum were convincingly compared to theoretical patterns, based on the idea that the ablation creates a normal pressure applied to the surface. This has led to the prevailing assertion that the pressures associated with ablation create the AB waves. The shape of the directivity pattern depends on source intensity, optical penetration depth [15], and generating spot size. In this case the diameter is 0.5 cm. In attempt to examine this possibility in this composite, an experiment measuring the directivity patterns of ultrasound was carried out.

Figure 19:
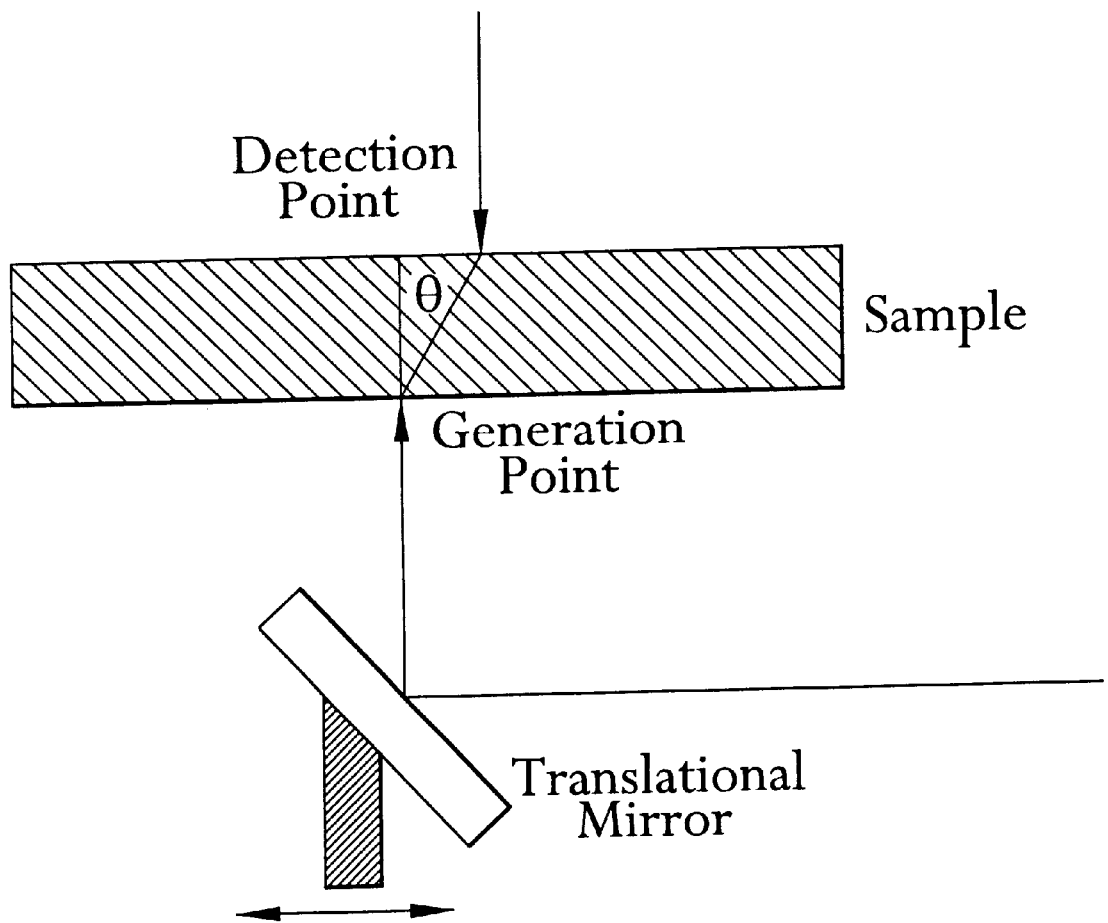
FIG. 19  Diagram of the experimental arrangement for measuring the directivity patterns. The angle θ is the directivity angle.
Figure 20:
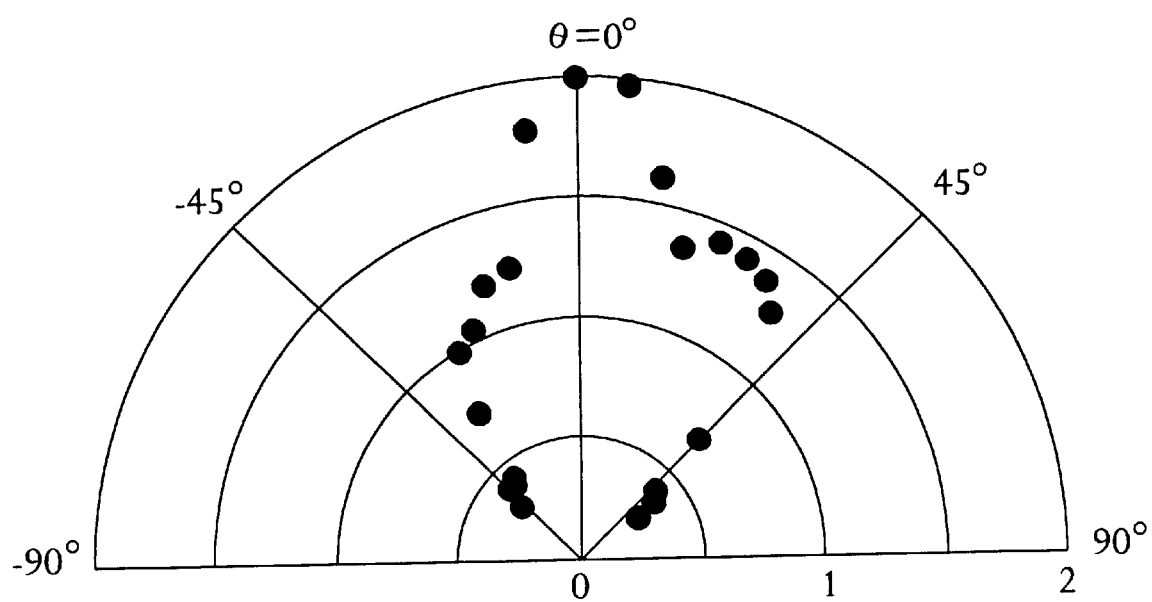
FIG. 20  Directivity pattern of thermoplastic longitudinal waves in 2.9 mm thick Gr/PEEK composite.

An experimental arrangement, shown in FIG. 19, was initiated. While the detection point was held fixed, the generating spot was translated from one side of epicenter to the other. The peak-to-peak amplitudes of waveforms at each point were recorded as a function of generation position. The directivity pattern in the thermoelastic regime is shown in FIG. 20.

With the detection system in the reflection mode, this was a broader range of frequencies (0.5–20 MHz) detected than those studies using transducer detection. The geometry is rectangular. Thus, waves traveling at greater angles travel through more material. Suffering increased attenuation, the directivity pattern becomes more focused.

Measuring the amplitudes of AB waves led to several difficulties. A separation technique, where wave captured in the TE regime are scaled and subtracted from waves at the same detection points in the ablation regime, in my judgment, is inappropriate for the measuring the directivity pattern. The influence of laser shielding by the ablation plume has a non-uniform affect on the strength on the TE wave in the ablation regime. If the intensity of the TE wave cannot be predicted, it cannot be accurately subtracted out. A method similar to that described in Section 6.2 where many waveforms are generated at each detection point to calculate the regression coefficients would be too strenuous for the detection system. Exposure of the detection surface, over long periods of time, to the detection laser degrades the reflective surface coating. This would contaminate the results.

Figure 21:
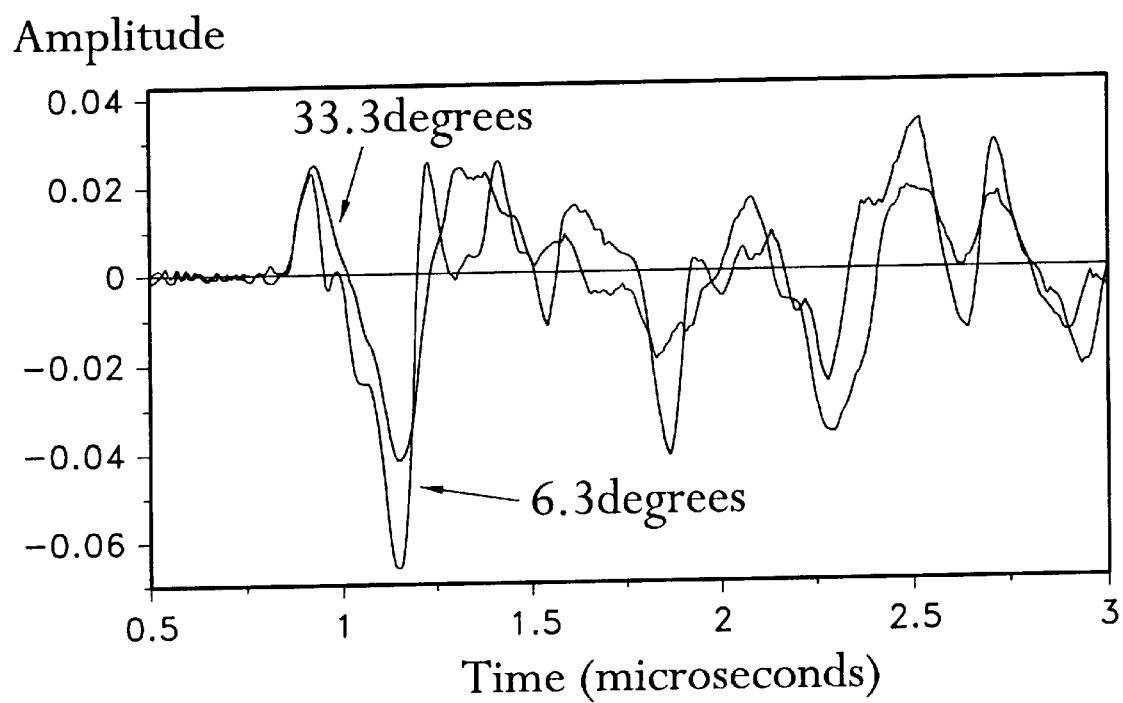
FIG. 21  Waveforms generated in the ablation regime, from two different positions and adjusted for in time for comparison. The high frequency aspects near the epicenter are not discernable further away.

A simpler method determines the influence of the AB wave on the combined waveform by subtracting the amplitude of an identified AB peak from a TE peak. The height of the AB peak that projects out of the TE waveform is measured and plotted with angle. Unfortunately this is more of a measure of the resolution of the two waves that stems from the attenuation of higher frequencies, than the directivity of the AB waveform. This can be seen by comparing waveforms taken from two different positions, as displayed in FIG. 21.

The graph displays two waves taken at 6 and 33 degrees from the epicenter. Although the waveforms exhibit the same basic shape, the higher frequency aspects are not discernible far from the epicenter. A true directivity pattern of an ablatic wave in a composite may only be obtainable using a custom-made half-cylindrical specimen with cylindrical symmetry.

Figure 22:
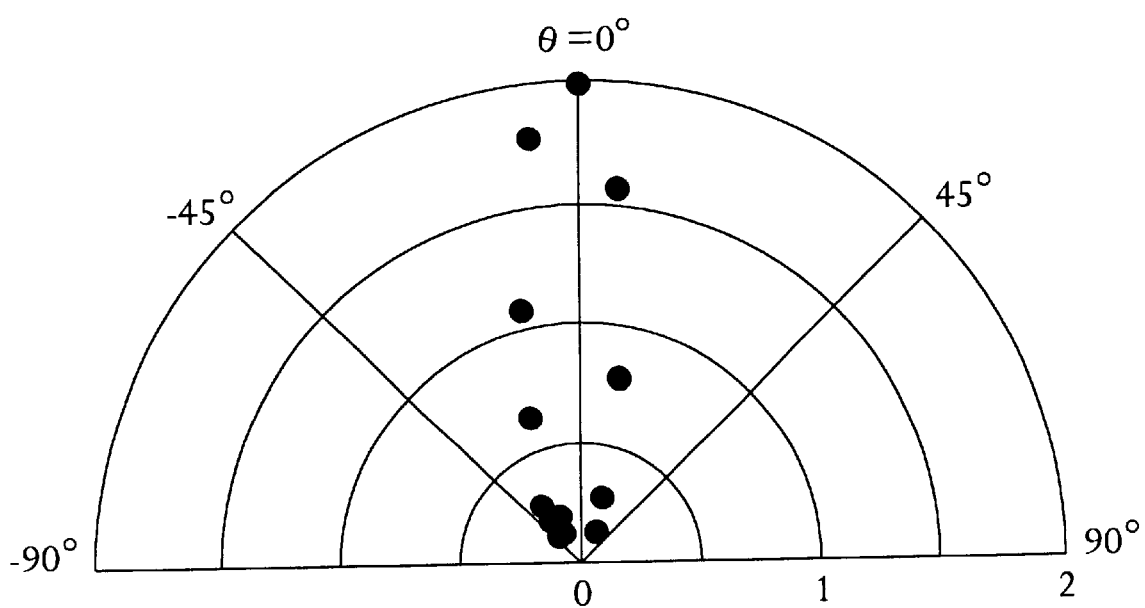
FIG. 22  Directivity pattern of resolved ablatic longitudinal waves in 2.9 mm thick Gr/PEEK composite. The attenuation of higher frequencies provides only a narrow region where the TE and AB waves can be resolved.

The results are shown in FIG. 22. The region in which the AB wave can be resolved in narrow. For this composite, the wave can only be seen at points less than 20 degrees (or 1.1 mm) of the epicenter. This does answer the question of why the AB wave seen so elusive. The narrow region for which the AB is resolved from the combined waveform is comparable to the size of the detection laser spot size (d$\approx$0.7 mm). Waveforms captured with small misalignments in laser beams will not shown the waveform.

6.5 Ablative Effects in Various Materials

6.5.1 Ablation Plume Signals in Various Materials

The characteristics of the plume can be directly related to characteristics of the AB wave.

Figure 23:
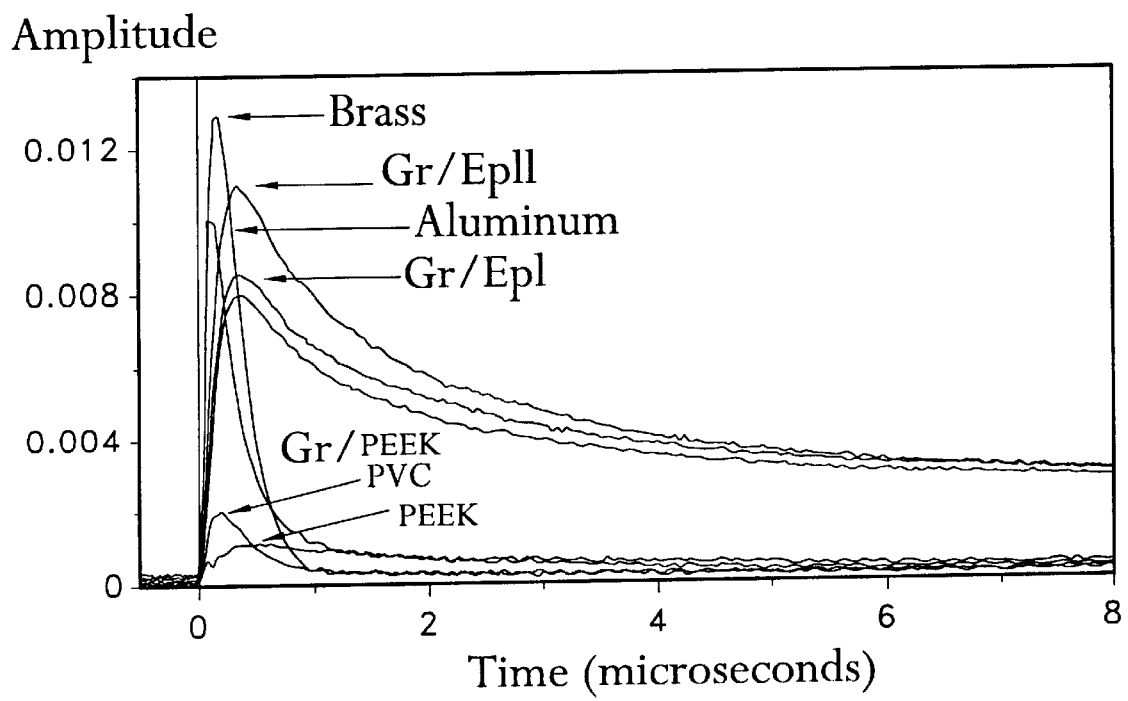
FIG. 23  Graph of ablation plume signals from various materials. The composite materials reach their maximum after the other materials achieve maximum.

Table 6.1 shows rise and initial fall times for the ablation plume signals of different materials as measured by the digital oscilloscope. All three composites show comparable times, which are significantly dissimilar than either the polymers or metals tested. The composites display faster rise times and much slower decay times. The signals are shown in FIG 23.

Since the decay of the ablation process is greater in the composites, their AB waves should be easier to resolve from the TE waves.

6.5.2 Ablatic Waveform in Aluminum

Figure 24:
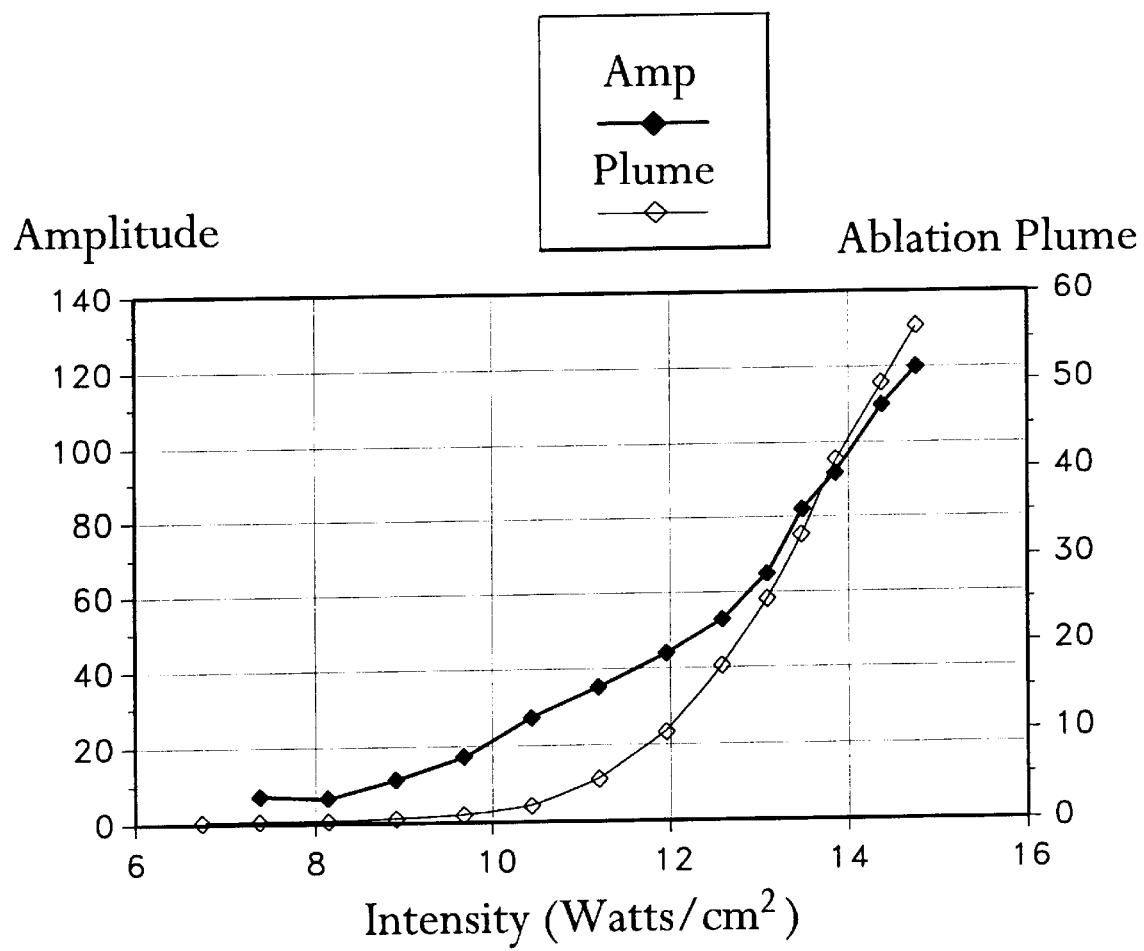
FIG. 24  Graph of amplitudes of the first longitudinal waves in aluminum as generating laser intensity is increased through the laser ablation threshold. The corresponding ablation detector is also shown.

Following the procedure in Section 6.2, laser-generated waveforms were detected in an aluminum sample. As a result of the high reflectivity, generation in the thermoelastic regime was very poor. Only waveforms at a few intensities could be detected before the ablation threshold is surpassed. Their amplitudes and the corresponding ablation detector data are displayed in FIG. 24.

The ablation threshold is reached at about 9 W/cm$^2$. Here the amplitudes take a drastic change in slope. A second change occurs at 13 W/cm$^2$. It appears that the generating efficiency of aluminum in ablation is much greater than the efficiency in the thermoelastic regime when compared to the composites.

Figure 25:
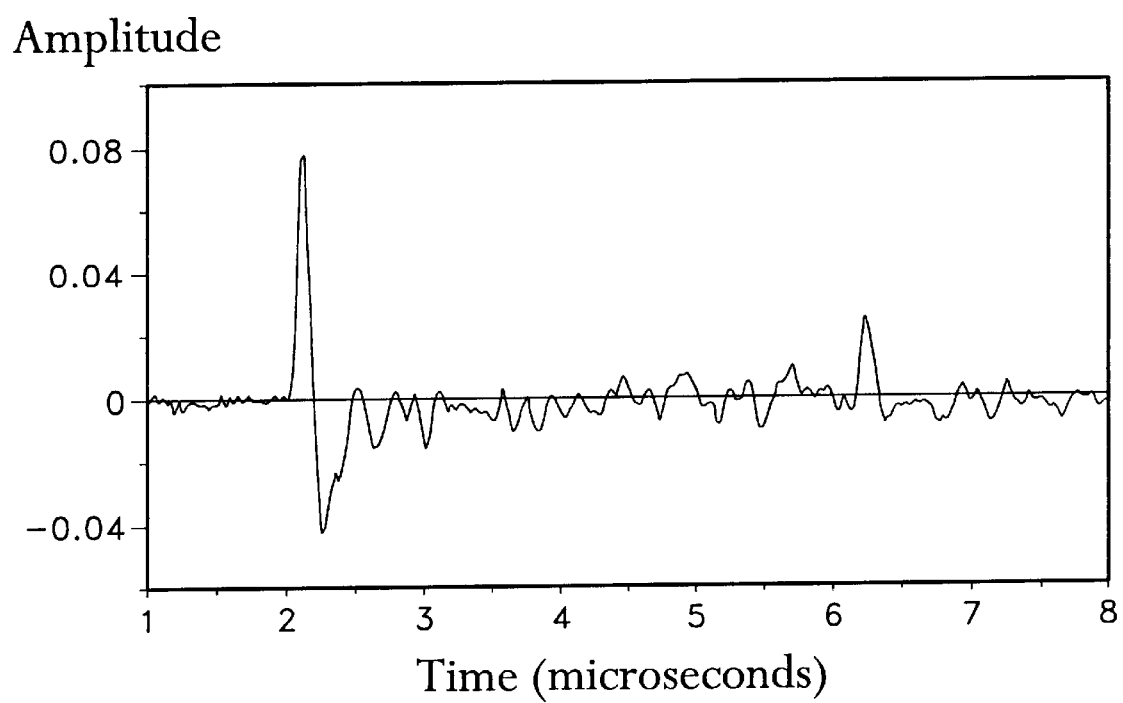
FIG. 25  Graph of an ultrasonic wave generated in the ablation regime, in aluminum. No resolution of the TE and AB waveforms could be seen at any intensity level.

The highest intensity waveform is shown in FIG. 25. No resolution of the two waveforms could be seen at any intensity level. This most likely is a result of a combination of two events. As a result of the greater generating efficiency, the AB obscures the TE wave at an intensity just above the threshold. The intensity region where the two peaks can be witnessed is therefore narrow. The intensity steps used in the experiment may be large compared to this region, and missed detection of the two-peak formation. Also, as seen in Table 6.1, ablation is a faster process in metals than in composites. The TE and AB waveforms may occur within a time period smaller than do the waveforms in graphite-fiber composites. The current system might not be fast enough to detect the resolution.

In the previous experiment, the generating laser beam was not focused to further increase the intensity. When working with Gaussian optics [40], light does not converge to a singular focal point. The focal point is expressed as the region of the narrowest convergence. Given the high reflectivity of aluminum, light focused on aluminum to achieve the ablation threshold will subsequently cause the breakdown of air adjacent to the sample. As reported in Scruby [21], the air-breakdown source is also sufficient to create an ultrasonic wave in the sample, and would also be modeled as a normal force. Whether the acoustic wave is generated by the ablation of aluminum or the breakdown of air is indeterminate. Using the original spot size of the laser avoids this hazard.

6.5.3 Ablatic Waveforms in AS-4/PEKK Composite

Figure 26:
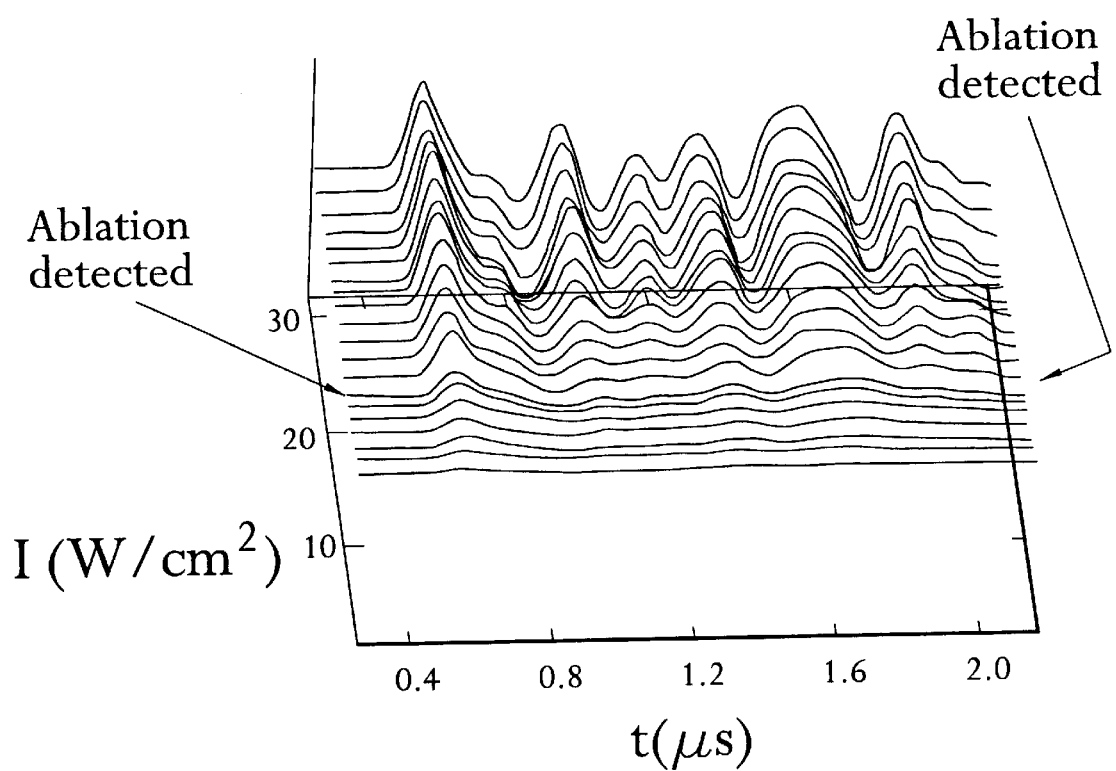
FIG. 26  Graph of evolution of the ablatic wave in 1.5 mm thick AS-4/PEKK [0/90]$_{2S}$ composite. The ablatic wave peak can be seen to emerge from the back slope of the thermoelastic longitudinal wave.

The ablatic wave experiment was repeated using a 1.5 mm thick AS-4/PEKK [0/90]$_{2S}$ composite. As before, a series of ultrasonic waveforms were generated and detected in the composite as the laser intensity was increased through the ablation threshold. The waveforms are exhibited in FIG. 26.

The first longitudinal wave occurs at 430 ns, followed by an echo at 1.3 µs. The first significant ablation is detected at an intensity of 11.3 W/cm$^2$. Following this, the ablatic wave peak, superimposed on the back slope of the longitudinal wave can be seen, especially at higher intensities. There is also a series of peaks occurring between echoes that can be attributed to a combination of the TE longitudinal and transverse waves, and the AB longitudinal and transverse waves. Since the sample is comparatively thin, the waves interfere with each other.

As in Section 6.2, three waveforms with the lowest intensities were averaged to form the TE basis function. The AB basis function was derived by averaging the three highest-intensity waveforms and subtracting off the scaled thermoelastic component. A series of regression fits were then performed on the waveforms using the basis functions. The resulting coefficients are displayed alongside their corresponding R$^2$ value in Table 6.2.

Figure 27:
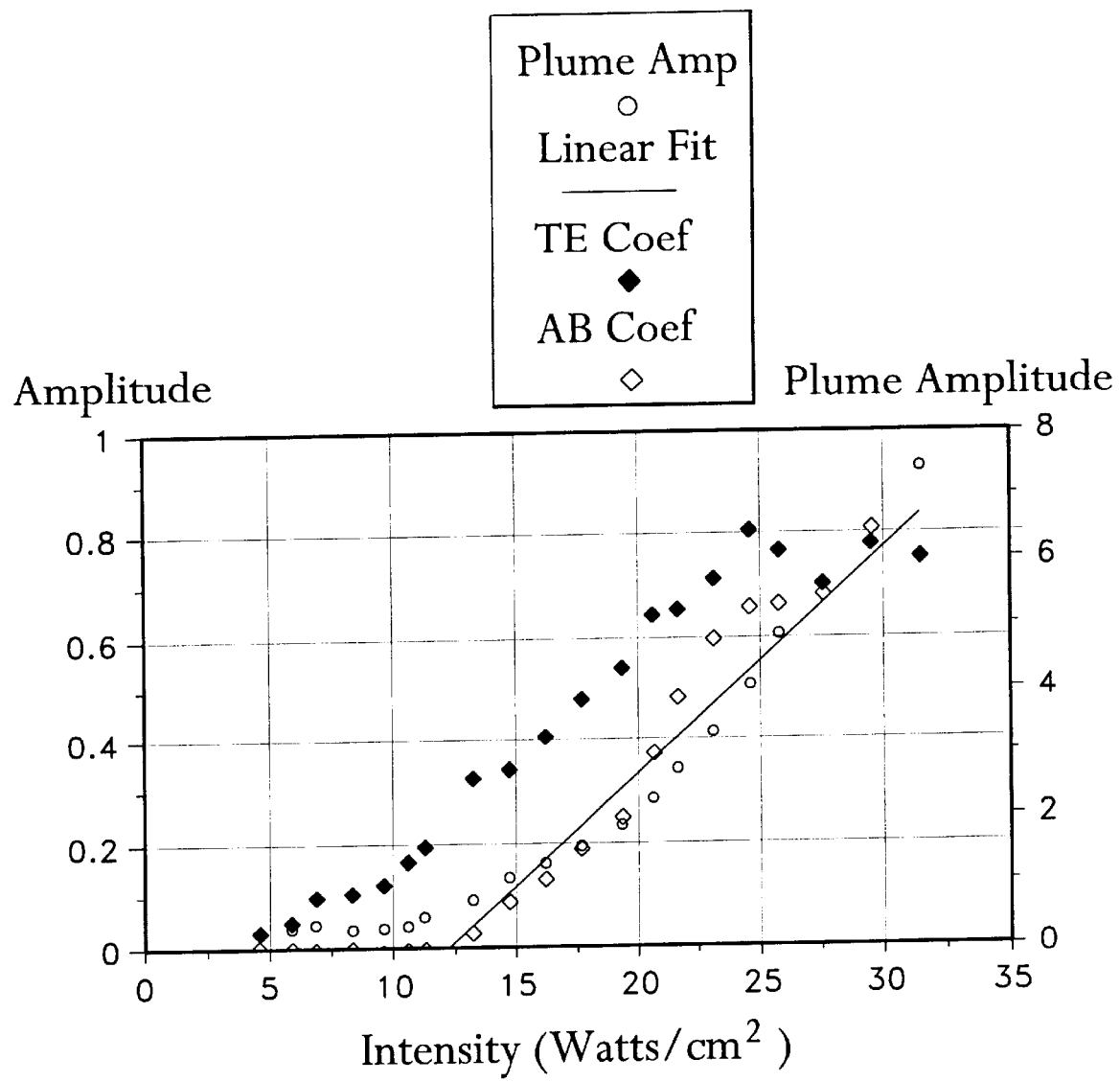
FIG. 27  Graph of thermoelastic (TE) and ablatic (AB) coefficients for 1.5 mm thick AS-4/PEKK [0/90]$_{2S}$ composite as a function of laser intensity. Also shown are the ablation plume amplitudes. The AB coefficients and ablation plume amplitudes exhibit similar thresholds.

The coefficients are plotted as a function of intensity, along with the signal amplitude of the ablation plume detector, in FIG. 27. The TE coefficients shown a discernible change in slope near the threshold. The AB coefficients are once again consistent with the ablation plume data, revealing a threshold near 12.5 W/cm$^2$.

There are two significant differences between the ablative affects in the composite and the graphite/PEEK composite. In contrast to previous experiments, the TE coefficients have an increase in slope following the detection of ablation. This is possibly a result of some contamination of the TE coefficient by the AB component. Contamination would result if the AB basis function contains a portion of the thermoelastic wave. The second difference is the greater ablation threshold measured in the AS-4/PEKK composite. This is likely a result of greater reflectivity of infrared light by the polymer. Increased reflectivity decreases the absorption of light, thus decreasing the energy deposited in the sample. The laser intensity calibration does not account for the reflectivity of the sample. As a result, the ablation threshold as measured by this method will increase. In addition, much higher intensities were needed to detect the two-peaked longitudinal wave. This can also be explained by the above reasoning.

6.6 Ablatic Waveform Dependence on Laser Intensity

Figure 28:
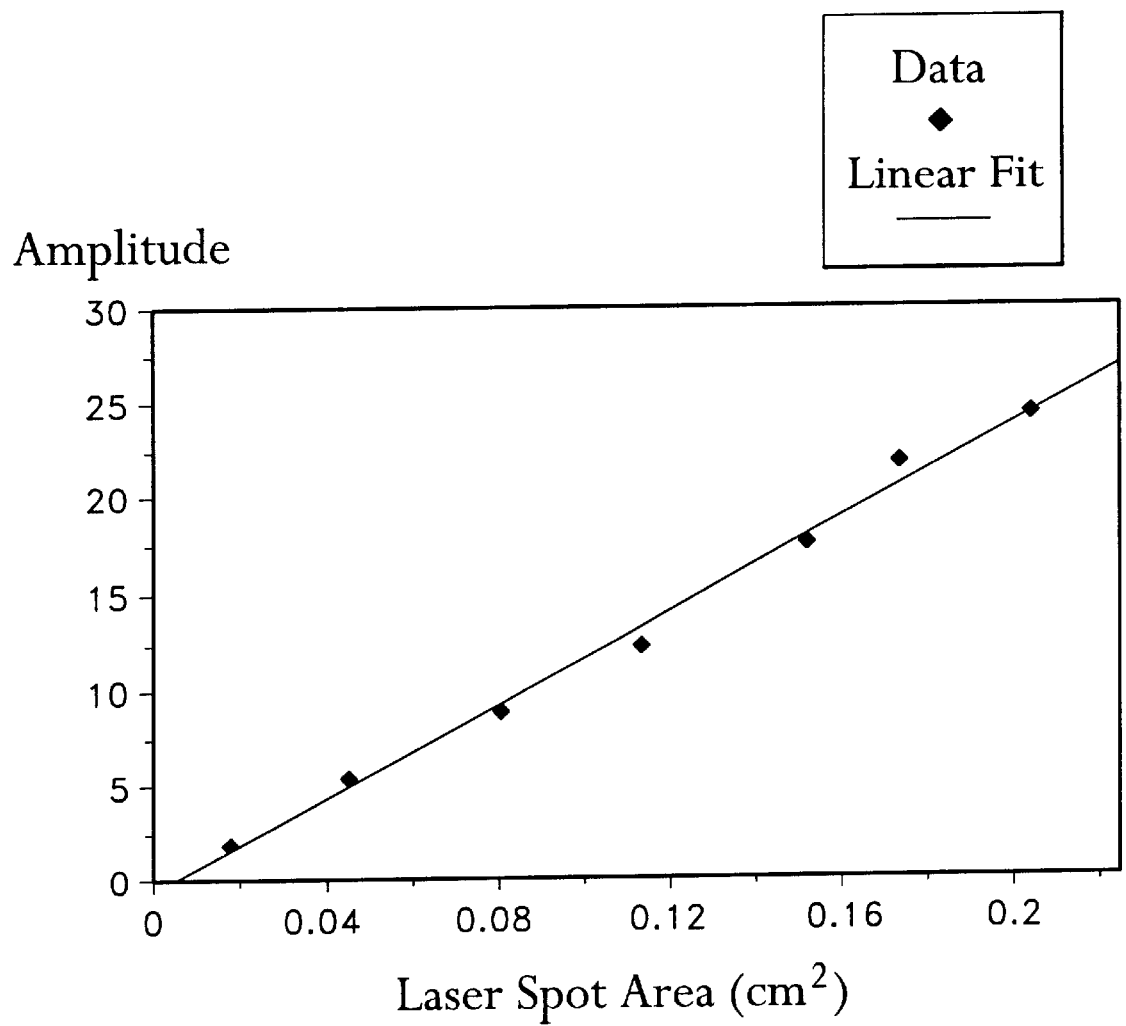
FIG. 28  Graph of ablation plume signal as a function of the generating spot size. The graph shows a linear relationship.

In attempt to model the ablatic wave's dependence on laser intensity, a unitless quantity $S_{ab}$ is defined as the strength of the ablation process. $S_{ab}$, by assumption, is linear with the light produced by the reaction. Empirically, as shown in FIG. 28, the ablation plume light is linear (R$^2$= 0.993) with the generating spot area.

This experiment used an aperture to vary the spot size, burn paper to measure the area, and corresponding data from the ablation detector. The laser pulse can be represented as $$I(r) = I_o e^{-\frac{r^2}{2a^2}} \tag{6.2}$$

where r is the distance from the center and a is the half-width at half maximum of the Gaussian distribution.

Figure 29:
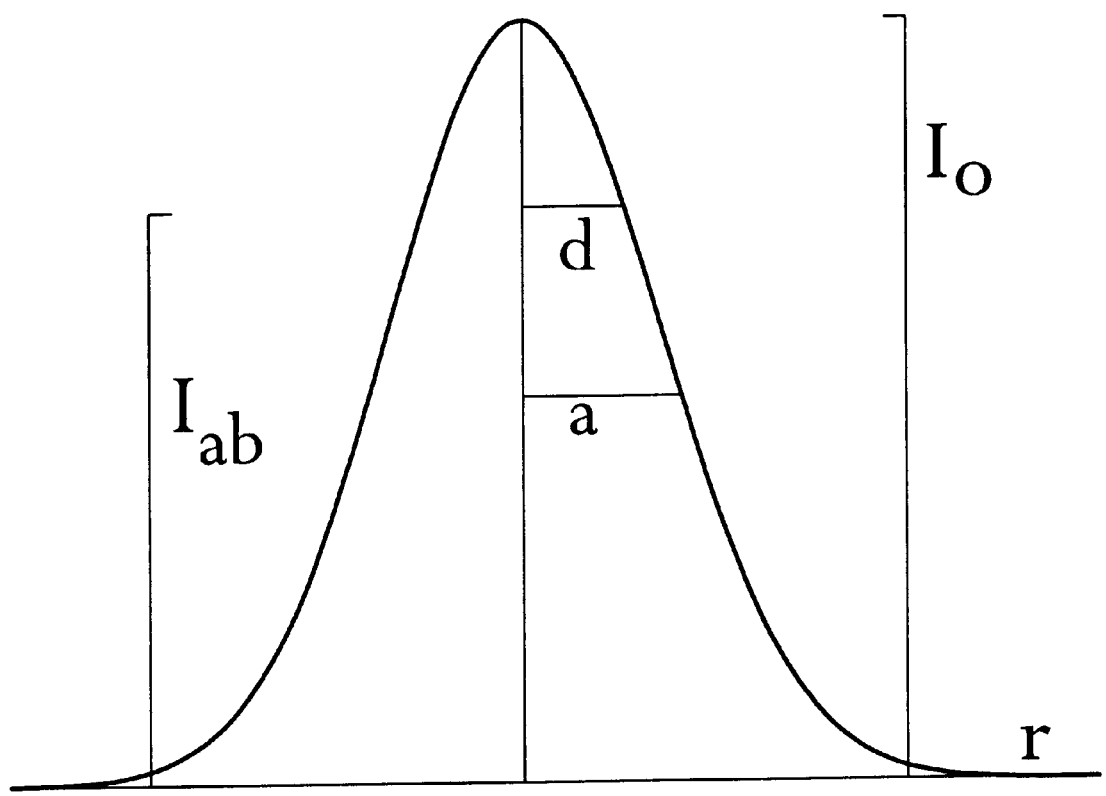
FIG. 29  Theoretical Gaussian profile of the generating laser pulse showing the parameters used in Equation 6.4. I$_{ab}$ is the ablation threshold intensity level.

The material will only ablate above a threshold $I_{ab}$ which from FIG. 29 does not encompass the entire area of the pulse. Therefore $$I_{ab} = I_o e^{-\frac{d^2}{2a^2}} \tag{6.3}$$

where d is the radius of the ablated area. Now, assuming $S_{ab}$ is proportional to the total intensity integrated over the ablated area $$S_{ab} \propto \int I(r) dA = \int_0^{2\pi} \int_0^d I_o e^{-\frac{r^2}{2a^2}} r dr d\phi \tag{6.4}$$

$$= 2\pi a^2 I_o \left(1 - e^{-\frac{d^2}{2a^2}}\right) = 2\pi a^2 (I_o - I_{ab})$$

showing $S_{ab}$ increases linearly with intensity above $I_{ab}$. If $S_{ab}$ is the cause of the ablatic wave, than the ablatic wave is also linear with laser intensity, or at least with the intensities tested here.

Figure 30:
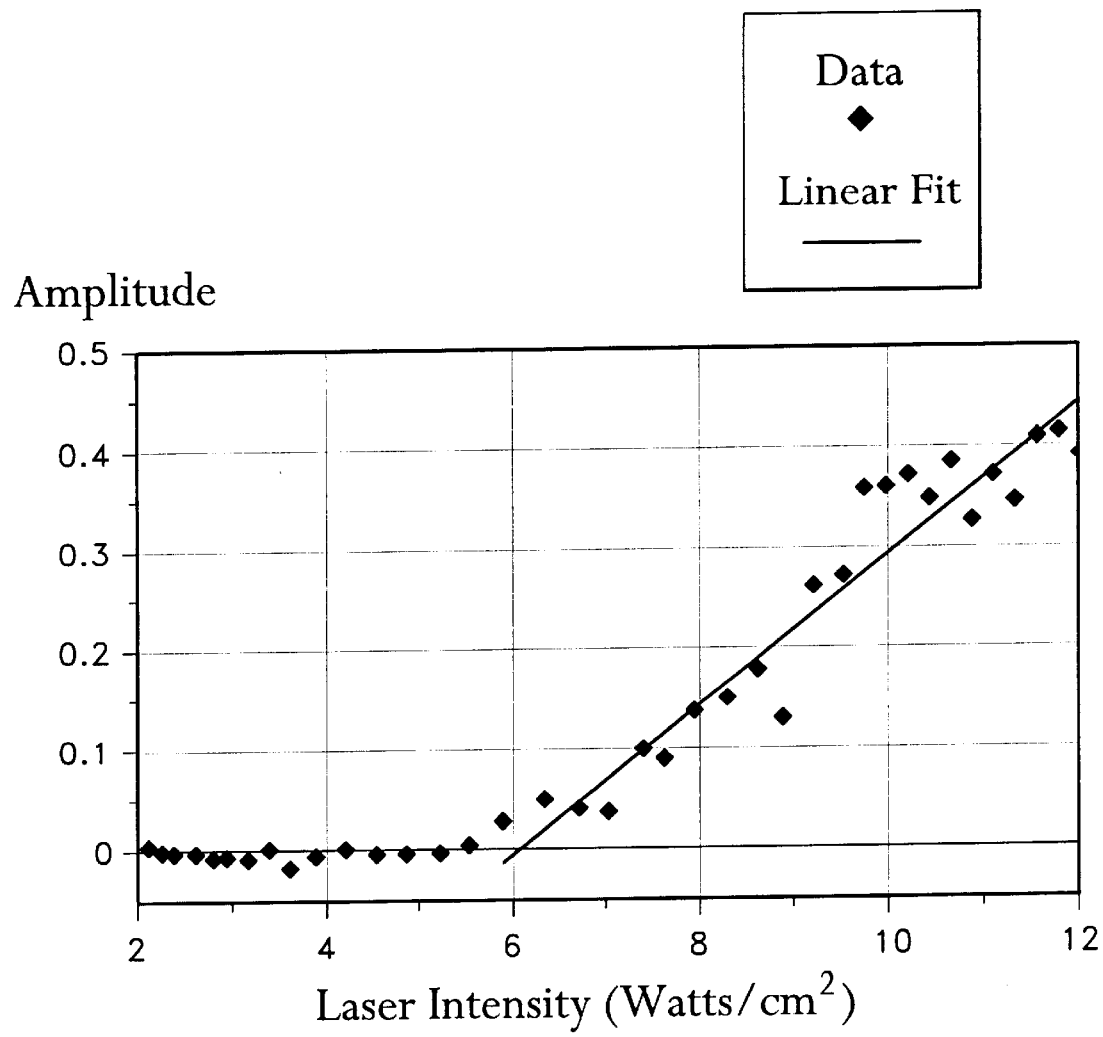
FIG. 30  Graph showing linear fit applied to ablatic wave coefficients from the experiment using the 2.9 mm graphite/PEEK composite. The fit shows a threshold at 6 W/cm$^2$ and has an R$^2$ value of 0.91.

A linear fit applied to the AB coefficients, shown in FIG. 30 reveals a threshold at 6 W/cm² with an R² value of 0.91.

TABLE 6.1

Characteristic times of ablation plumes from various materials, as detected by the ablation photodetector. Gr/epoxy I has a matte brown surface, indicating greater levels or epoxy, than the black glossy surface of Gr/epoxy II.

| Material | Rise Time (µs) | Decay Time (µs) | Time to First Max (µs) |
|---|---|---|---|
| Aluminum | 0.080 | 0.712 | 0.120 |
| Brass | 0.100 | 0.424 | 0.200 |
| Pure PEEK | 0.088 | 2.432 | 0.520 |
| Pure PVC | 0.068 | 0.652 | 0.200 |
| Gr/PEEK | 0.028 | 5.480 | 0.360 |
| Gr/Epoxy I | 0.032 | 5.860 | 0.360 |
| Gr/Epoxy II | 0.048 | 6.632 | 0.036 |

TABLE 6.2

Thermoelastic and ablatic separation coefficients for AS-4/PEKK composite. The closer the R² value is to 1.00, the closer the sum of the basis functions multiplied by their respective coefficients resembles the empirical waveform.
AS-4/PEKK Composite Waveform Coefficients

| Intensity (W/cm²) | TE Coefficient | AB Coefficient | R² Value |
|---|---|---|---|
| 4.62 | 0.030 | 0.001 | 0.985 |
| 5.89 | 0.050 | 0.000 | 0.996 |
| 6.88 | 0.097 | −0.004 | 0.986 |
| 8.35 | 0.106 | −0.004 | 0.986 |
| 9.63 | 0.122 | −0.009 | 0.950 |
| 10.61 | 0.167 | −0.005 | 0.973 |
| 11.30 | 0.194 | −0.003 | 0.974 |
| 13.26 | 0.326 | 0.029 | 0.979 |
| 14.74 | 0.342 | 0.088 | 0.949 |
| 16.21 | 0.407 | 0.132 | 0.956 |
| 17.68 | 0.481 | 0.190 | 0.968 |
| 19.35 | 0.541 | 0.249 | 0.982 |
| 20.63 | 0.645 | 0.374 | 0.969 |
| 21.61 | 0.656 | 0.484 | 0.984 |
| 23.09 | 0.713 | 0.599 | 0.981 |
| 24.56 | 0.806 | 0.660 | 0.956 |
| 25.74 | 0.765 | 0.664 | 0.982 |
| 27.51 | 0.701 | 0.681 | 0.992 |
| 29.47 | 0.779 | 0.807 | 0.998 |
| 31.44 | 0.751 | 0.745 | 0.991 |

Chapter 7

CONSEQUENCES OF LASER GENERATION

This chapter details several experiments, based on the interaction of a laser pulse with the surface of a solid, which have led to a better understanding of laser generation of ultrasonic waves in composites. Section 7.1 examines the ablation plume signal and its dependences on intensity, detection position, and source material. Section 7.2 displays micrographs of laser damaged composites.

7.1 Photodetection of the Ablation Plume

7.1.1 Parabolic Dependence of the Ablation Plume on Laser Intensity

To understand the parabolic dependence of the ablation detector response to ablation plumes with varying laser intensity, several experiments were performed. From visual observations (with protective goggles), the plume appeared to be approximately cylindrical with the length increasing with increasing laser intensity. The relationship was measured by photographing the plume at each intensity level and measuring the length of the plume off of the photographs.

Figure 31:
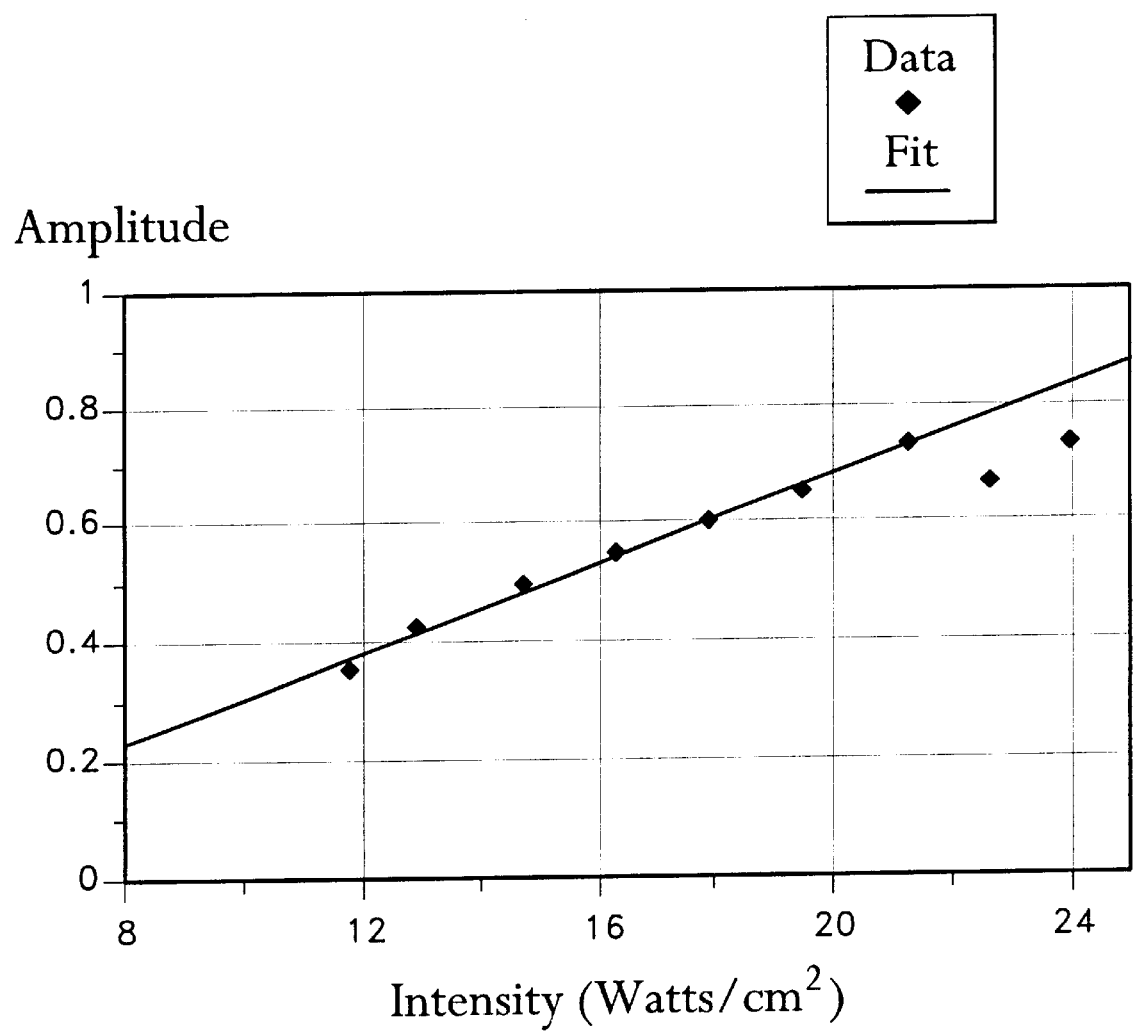
FIG. 31  Graph shown the dependence of the ablation plume length on source laser intensity. The plume was photographed at varying intensities. The length of the ablation plume was measured directly from the photograph.

As FIG. 31 shows, the length has a linear dependence on the intensity, yielding an R² value 0.902.[1] Thus one factor A of the parabolic dependence could be the result of the detector's wide field view.

[1] The R² value describes the amount of linearity in a least-squares fit. The closer to unity, the better the linearity of the data.

A second experiment consisted of placing a narrow slit in front of the detector to eliminate the wide field of view. The result, shown in FIG. 32, also shows a linear relationship with laser intensity, with R²=0.971. The A² dependence is therefore a result of the light produced in each segment of the plume multiplied by the contribution from the length of the plume.

Further proof was established by placing the ablation detector on the approximate cylindrical axis of the ablation plume. As shown in FIG. 33, this eliminates the A dependence that results from the length of the plume. The linear fit also shows a threshold above 5 W/cm² with R²=0.994. Unfortunately, since the relationship varies from linear to a parabolic depending on the position of the detector, the value of the threshold can also vary depending on position and how it is calculated.

7.1.2 Identification of the Source Material of Ablation

As stated earlier, the process of ablation is material dependent. It is therefore plausible that the photodetected ablation plume signal may be used to identify the material that is being ablated from the composite. Using this approach, plume signals were taken from pure PEEK, pure Graphite, and the composite.

As shown in FIG. 34, the graphite is almost a perfect match to the composite.

FIG. 35 shows the strong correspondence up to 300 µs. Since the AB wave has been directly connected to the ablation plume, as shown in Section 6.2, the AB wave in this composite is a direct consequence of the ablation of graphite.

7.2 Surface Damage to Composite Materials Created by Laser Impact

Surface damage created by the impact of laser pulses was investigated by visual microscopic observation of samples. With the microscope lens magnification at 10×, damage, created under three different conditions, was viewed on the 2.9 mm graphite/PEEK and the 8.9 mm graphite/epoxy samples.

The first condition consisted of 20 shots from the laser at a moderate intensity in the thermoelastic regime. Photos of a virgin area, and one shot with the laser are shown in FIGS. 36 and 37 for the PEEK matrix composite.

The fibers appear not to be affected. There is slight melting of the polymer, tending to increase with intensity. This is most likely the result of the fibers conducting thermal energy into the polymer. The effect is more dramatic in the epoxy sample, shown in FIGS. 37 and 38.

An increase of epoxy is apparent where laser impact has occurred. Here the fibers are conducting heat to epoxy just underneath the surface, and, under the localized expansion, the epoxy flows to the surface. This damage, however, is for the most part superficial, and probably insignificant when considering changes to the effectiveness of the composite.

The second condition consists of one shot in the ablation regime. This observation supports the ideas in Section 7.1.2, where graphite fibers were presumed to have absorbed the majority of the laser pulse, after the light is transmitted through the polymer surface. FIG. 40 shows the edge of surface damage created by the ablation on the graphite/PEEK composite.

The edges of the polymer are jagged, much like broken glass. This is consistent with the scenario that the fibers absorb the laser pulse, ablate, and shatter the thin polymer surface. Rounder edges would have been seen if the polymer absorbed more laser light.

FIG. 41 shows the third condition, 20 shots from the laser at ablation intensities, on the graphite/PEEK sample. Comparison of the two photos show increased damage to the fibers, as expected.

FIGS. 42 and 43 shows the edge of surface damage from one (A) and twenty shots (B) in the ablation regime, on the graphite/epoxy composite. After one shot, the woven top layer is ablated revealing a layer of aligned fibers underneath. Repeated shots remove further layers of fibers.

Chapter 8

APPLICATIONS OF LASER ULTRASONICS 8.1 Ultrasonic Scanning of Composite Materials The primary reason for current research in LU is the ultrasonic scanning of materials. A C-scanning[1] apparatus has been developed and integrated into the system [50],[2] shown in FIG. 44.

[1] A C-scan is a point-by-point scan in two dimensions.
[2] Additional improvements were made by Yuqiao Yang.

Two screw-driven arms provide movement of the sample in front of the stationary laser beam in the horizontal and vertical directions. The motion of the arms are controlled by the Macintosh lab computer via a multi-axis power/amplifier interface. The computer also controls the firing of the laser and data acquisition via Lab View software. A second computer can be added to add a second layer of stabilization to the servo circuit. Amplitudes of the first longitudinal waves are measured and plotted in gray-scale in two dimensions.

FIG. 45 shows a C-scan, taken with the CFP-based system in reflection configuration, of a 8.9 mm thick graphite/epoxy plate embedded with an Teflon flaw having the surface area of a quarter. Lighter areas show good reception of the ultrasonic signal while white areas show very little reception, implying a flaw.

FIG. 46 shows a C-scan, taken with the CFP-based system in transmission configuration, of a tow-placed panel (AS-4/PEKK, $[0/90]_{2S}$) alongside a more conventional immersion based C-scan [51]. The highlighted area shows tow-ply variations that match well with the original C-scan. The detection side of the panels were coated with aluminum paint to improve the reflectivity. If this system were to be customized for industrial use, a more elaborate configuration, such as described by McKie et al. [19] using a long-pulse amplifier, would be necessary.

8.2 Measurement of Properties at Elevated Temperatures

Another application of LU is measuring material properties at elevated materials. In this situation, LU has a decided advantage over contact transducers, which are susceptible to changes in temperature. The system was applied to measuring the sound velocity in solids as a function of the material temperature [52]. An oven has been constructed with ports allowing the lasers to impinge on the enclosed sample. Thermocouples embedded in the sample monitored the temperature changes. A laser extensometer was positioned normal to the lasers beams to accurately measure the thickness of the sample as it expands with temperature.

The setup is shown in FIG. 47. The sound velocity was easily found by dividing the thickness by the time of flight of the first longitudinal wave.

The results are shown in FIG. 48 for pure PEEK and 16 ply quasi-isotropic laminates of graphite/PEEK APC2 composite. Both curves show a transition beginning at the glass transition temperature, where the velocity falls off rapidly. Data from this experiment was used to model the bond of two composites during processing [52].

Other similar applications include measuring material parameters in enclosed areas and measuring the thickness of thin coatings undergoing chemical vapor deposition [53]. The elevated temperatures also mimic possible industrial production environments.

Chapter 9

GAS-COUPLED LASER ACOUSTIC DETECTION (GCLAD)

9.1 Introduction

An inherent paradox exists in laser ultrasonics. To optimize generation of an acoustic wave in a solid, the material must absorb as much laser light as possible. To achieve the best possible detection of the wave, the material must reflect as much laser light as possible. These objectives conflict under the same surface specifications. For graphite fiber reinforced composites, where generation efficiency is good, detection is poor. For metals, the opposite occurs. The primary solution is research labs, for composites, is to coat one side of section of the sample with reflective paint, as was done in the first part of this study. Although effective for research, this is not a viable solution for industrial applications. A long-pulse laser amplifier can be introduced into the detection system [19], providing around 1000 times the detection light in a 100 $\mu s$ pulse. This, however, adds another layer of complexity to the system, and more than $100,000 to the price tag. The recent introduction of air-coupled (AC) transducers provides a reasonable alternative [54]. Using a pulse laser to generate the ultrasonic wave, and the AC transducer to detect the pulse after it has been transmitted into the air medium, appears to be the most efficient use of the transducers. However, like their contact counterparts, AC transducers are restricted to a range of temperatures and susceptible to microphone ringing [55].

Based on the results of AC transducers, it is evident that there is a detectable ultrasonic wave in air that can be transmitted from a solid. Therefore, if a laser beam is passed through this region where the wave passes, it may affect either the frequency, phase, or path of the laser beam, since air is pressure dependent. Whether this disturbance could be detected was answered by a simple laboratory experiment. A piezoelectric translator was positioned near the path of the beam such that ultrasonic waves would travel in the air, and through the laser beam. Although initially very faint, the disturbance created in the air by the translator had affected the beam enough such that the acoustic wave was detected by the photodetector. Experiments, detailed in Chapter 10, confirmed that changes in the index of refraction in the air, caused by the ultrasonic wave, bend the laser beam off of its original path. The resulting misdirection of the beam on the photodiode yielded a detectable change in the signal voltage.

This offers an alternative to interferometric detection. The detection beam, instead of being reflected off the sample, can be passed parallel to the surface. An ultrasonic wave passes through the sample, and is transmitted to the air. The airborne wave is detected when it passes through the laser beam. There is no dependence on surface reflectivity or optical smoothness of the surface. This provides a solution to the paradox mentioned above. In addition, there is not need for a stabilization circuit, specialized optics, or realignment when one sample is exchanged for another. This technique can be performed in any gaseous environment and has a uniform frequency response. This technique has since been designated Gas-Coupled Laser Acoustic Detection or GCLAD.

9.2 Background

9.2.1 Air-Coupled Ultrasonic Detection

Air-coupled detection of ultrasound has been accomplished by a variety of transducers [56]. One conventional method used a flexible metallic membrane stretched over a roughened backing plate [57]. The response is mainly governed by small pockets of air trapped between the membrane and the backplate. Piezo-ceramic transducers in their conventional (contact) form of not function well in air due to the large acoustic impedance mismatch between the air and the ceramic. Using a layered structure, such as the ceramic-epoxy composite structure described by Hutchins et al. [55], the mismatch can be reduced. Most AC transducers have narrow bandwidths usually in the high kiloHertz region. Recent advances using micromachining have enabled Ladabaum et al. [58] to fashion narrowband transducers which achieve detection of frequencies as high as 11.4 MHz, and Schindel et al. [59] to build wideband transducers possessing a bandwidth of 2 MHz.

The difficulty of detecting megahertz frequencies is increased by the acoustical absorption in air. Above 200 kHz, where classical absorption dominates, the attenuation of the wave is exponential [60]. The pressure amplitude p of a wave at a distance z from the initial position can be expressed as $$p = p_o \exp(-\alpha z) \quad (9.1)$$

where $p_o$ is the root-mean-square pressure amplitude of an acoustical plane wave at the initial position and $\alpha$ is the absorption coefficient in inverse meters. Above 200 kHs, the absorption coefficient is governed by the empirical formula [60].

$$\alpha \approx 2 \times 10^{-14} \text{ mm}^{-1}/(\upsilon/\text{Hz})^2 \quad (9.2)$$

where $\upsilon$ is the acoustic frequency. This can also be expressed as an extinction distance $$\text{extinction distance} = 5 \times 10^{13}/(\upsilon/\text{Hz})^2 \text{ mm} \quad (9.3)$$

The extinction distance represents the distance over which the amplitude of a waveform drops to 1/e of its original value. As a result of the inverser-squared dependence, the extinction distance reduces from about 1.25 m at 200 kHz to only 2 mm at 5 MHz. Hickling and Marin [60] exhibit data showing the dependence of absorption on temperature and relative humidity over a range of frequencies.

9.2.2 Laser Beam Deflection Techniques

Applications using laser beam deflection techniques can be divided into three categories: deflection by a reflection off a moving surface, deflection by a temperature gradient, and deflection by a pressure gradient. The first method entails reflecting a laser beam off the surface of the sample at a specific angle and detecting the change in angle when an ultrasonic comes to the surface. This method is still dependent on the surface qualities.

Deflection by a temperature gradient, called photothermal laser beam deflection (PTD) [61] or the "mirage effect" [62], has been used to obtain the thermal diffusivities of bulk solids and thin films. A chopped light beam periodically heats the surface of the beam. The thermal energy is radiated from the surface into the surrounding medium. Probe beams are pass through this area and deflected by the temperature gradients. The deflection is measured by position-sensitive detectors. This method has also been used to quantify the density [63] and velocity [64] of the ablation plume particles. The laser beam is directed through the plasma, deflected by the differences in the index of refraction, and detected by a position sensitive detector. Although similar to GCLAD, this technique does not require the same level of sensitivity. A review of this subject is included in reference [65].

The third method, deflection by a pressure gradient, includes GCLAD and the acoustooptic effect. In the acoustooptic effect, sounds waves traveling in a medium, typically water or glass, create a diffraction grating which can deflect a laser beam. The angle of deflection can be varied by changing the frequency of the sound waves. The creation of a diffraction grating distinguishes the acoustooptic effect from GCLAD. Transient beam deflection in transparent liquids [66] and solids [67] has been accomplished by a number of groups. In these cases, the increased index of refraction provides greater deflection angles, requiring less sensitivity. To the best of our knowledge, GCLAD is the first reported instance of detecting acoustic waves in a gaseous medium by laser beam deflection caused by transient changes in the index of refraction.

9.3 GCLAD Theory

The detection of acoustic waves in a gaseous medium by beam deflection of a laser beam can be generalized as follows: A continuous wave laser beam is pass through a region where an acoustic disturbance is expected. The variations in gas density, caused by the acoustic disturbance, create similar variations in the index of refraction of the medium. The laser beam is deflected from the original path by these variations. A photodetector, placed a significant distance away from the interaction, captures the light. The detector is specially designed such that slight changes in the position of the laser's Gaussian-shaped intensity distribution on the photocell result in a similar change in the photodetector's output. An aperture mounted on the detector allows only the preferred portions of the intensity distribution to fall on the photodiode.

GCLAD theory involves four relationships: the transmission of an acoustic wave from a solid to gaseous medium; the air borne wave's influence on the index of refraction; the laser beam deflection created by the change in the index of refraction; and photodetector's signal voltage's dependence on the deflection angle.

9.3.1 Transmission of an Acoustic Pulse from Solid to Gas

When a normal longitudinal acoustic wave arrives at an interface between two mediums, part of the wave is reflected and part is transmitted into the second medium. A wave, represented by the pressure $$p_i(x,t) = \hat{p} e^{i(wt-kx)} \quad (9.4)$$

incident on the interface, separates into $$p_r(x,t) = R\hat{p} e^{i(wt-kx+\beta)} \quad (9.5)$$

and $$p_t(x,t) = T\hat{p} e^{i(wt-kx)} \quad (9.6)$$

where β represents a phase change, and R and T are the reflection and transmission factors [68]. From Equation 9.6, it is apparent that the airborne wave is representative of the solid wave. The factors are defined for normal incidence by $$R = \frac{Z_0' - Z_0}{Z_0' + Z_0} \quad (9.7)$$

and $$T = \frac{2Z_0'}{Z_0' + Z_0} \quad (9.8)$$

where $Z_0$ and $Z_0'$ are the characteristic impedances for the two mediums.

For transmission of a wave from a solid to gaseous medium, $Z_0$ is typically five orders of magnitude larger than $Z_0'$. For example, the characteristic impedance is $4.70 \times 10^6$ kg·m$^{-2 \cdot s-1}$ for a carbon/epoxy composite, and 427 kg·m$^{-2}$·s$^{-1}$ for air [69]. In this case, R=0.9998 and T=1.82×10$^{-4}$. Therefore, the amplitude of the transmitted wave is about four orders of magnitude smaller than the original wave amplitude.

9.3.2 Relationship between a Pressure Disturbance and the Index of Refraction The relationship between the index of refraction n and air pressure p can be expressed as $$n^2 - 1 \approx \frac{3pA}{RT} \quad (9.9)$$

where A is the molar refractivity, R is the universal gas constant, and T is the absolute temperature [40]. The sound wave enters as a small perturbation of the pressure. At 1 atm, the index of refraction in air is 1.0002939 [40] for 532 nm wavelength light. The right hand side of Equation 9.9 is therefore much smaller than one. Binomial expansion and approximation to the first order yields $$n - 1 \approx \frac{3Ap}{2RT}. \quad (9.10)$$

Introduction of the perturbations n≡n$_0$+Δn and p≡p$_0$+Δp, where Δn and Δp are small changes in the index of refraction n$_0$ and pressure p$_0$, allows Equation 9.10 to be cast in the forms $$\frac{\Delta n}{n_0 - 1} \approx \frac{\Delta p}{p_0}. \quad (9.11)$$

Equation 9.11 shows a changes in pressure leads to a proportional change in the index of refraction.

9.3.3 Beam Deflection by a Change in the Index of Refraction

Consider a cylindrical coordinate system where the non-perturbed laser beam serves as the z-axis and z=0 is positioned as the point of beam deflection. Acoustic disturbances will travel perpendicular to the beam, parallel to the r-axis. The Equation governing the relation between a ray of light and the index of refraction n(r, Φ, z) of the medium is the eikonal Equation [40], $$\frac{\partial}{\partial s} n(r, \phi, z) \frac{\partial R(r, \phi, z)}{\partial s} = \nabla n(r, \phi, z) \quad (9.12)$$

where R(r, Φ, z) is the ray trajectory, and s is the scalar path length. For a paraxial ray and primarily radial dependence for n(r, Φ, z), Equation 9.12 becomes $$\frac{\partial^2 r(z)}{\partial z^2} = \frac{\nabla n(r)}{n(r)} \quad (9.13)$$

$$\frac{\partial^2 r(z)\hat{r}}{\partial z^2} = \frac{1}{n(r)} \frac{\partial n(r)}{\partial r} \hat{r}$$

$$\frac{\partial^2 r(z)}{\partial z^2} = \frac{1}{n(r)} \frac{\partial n(r)}{\partial r}.$$

Therefore r(z) can be found for a given n(r).

A Fortran computer program has been written to solve Equation 9.13 for a set of variable. Consider an index of refraction with an acoustic disturbance of the form $$n(r, z) = n_0 + n_a e^{-\frac{r^2}{2s_i^2}} e^{-\frac{z^2}{2a_i^2}} \quad (9.14)$$

where $n_a$ is the maximum change created by the disturbance. The extent of the disturbance is represented by $s_i$ and $a_i$, which approximates the width and wavelength of the source. To depict an ultrasonic waveform, generated by a 1 MHz transducer and traveling through the path of the laser beam, the variable are chooses as $n_0$=1.0002939

$n_a$2.939×10$^{-5}$ $a_i$=2 cm $s_i$=0.35 mm v=350 m/s  (9.15)

where v is the speed of sound. The results of solving the eikonal equation, using these numbers, are shown along with n(t, 0) in FIG. 49.

Comparison with the original disturbance suggests that the resulting signal is a differentiation of the index of refraction. An analytical solution would show if this can be extended to all frequency ranges.

Since the variables involved are comparatively small, approximations can be made which will simplify the analysis of the eikonal equation. Consider an acoustic disturbance traveling in the r direction. The index of refraction consists of a constant, and a small acoustic modulation, n(r)=n$_0$+n$_a$ (r). Equation 9.13 takes the form $$\frac{\partial^2 r(z)}{\partial z^2} = \frac{1}{n_0 + n_a(r)} \frac{\partial n_a(r)}{\partial r} \quad (9.16)$$

$$\approx \frac{1}{n_0} \frac{\partial n_a(r)}{\partial r}.$$

The angle of deflection is assumed very small. Using the coordinate axis given in FIG. 50

$$\theta = \tan^{-1}\left(\frac{dr}{dz}\right) \approx \frac{dr}{dz}. \quad (9.17)$$

Substitution into Equation 9.16 yields $$\frac{\partial \theta}{\partial z} = \frac{1}{n_0} \frac{\partial n_a(r)}{\partial r}. \quad (9.18)$$

Upon integration $$\theta = \frac{1}{n_0} \int \frac{\partial n_a(r)}{\partial r} dz. \quad (9.19)$$

Given uniform ambient conditions, the acoustic wave will travel a constant velocity. For a wave traveling in the r direction, the acoustic pressure and hence $\Delta n$ are approximately a function of the variable r-vt. Therefore $$\frac{\partial n_a(r-vt)}{\partial r} = \frac{\partial n_a}{\partial t} \frac{\partial t}{\partial r} = -\frac{1}{v} \frac{\partial n_a(r-vt)}{\partial t}. \quad (9.20)$$

Equation 9.19 can be written as $$\theta = \frac{-1}{n_0 v} \int \frac{\partial n_a(r-vt)}{\partial t} dz. \quad (9.21)$$

Equation 9.21 demonstrates that the resulting beam deflection depends on the time derivative of the disturbance. Taking into account the discussion in Section 9.3.1, the amount of beam deflection is directly proportional to the first time derivative of the surface displacement.

If $n_a(r-vt)$ is approximately constant in a region defined from −b to +b along the z axis, Equation 9.21 becomes $$\theta = \frac{-1}{n_0 v} \int_{-b}^{+b} \frac{\partial n_a(r-vt)}{\partial t} dz = \frac{-2b}{n_0 v} \frac{\partial n_a(r-vt)}{\partial t} \quad (9.22)$$

revealing a direct proportionality between the length of the disturbance and the deflection angle.

9.3.4 Detection of the beam Deflection

Next, the dependence of the photo-detected signal on deflection angle will be derived. Let the probe laser intensity equal $$I(r) = \frac{I_0}{\pi a^2} e^{-(r/a)^2} \quad (9.23)$$

such that $$2\pi \int_0^\infty I(r) r dr = I_0. \quad (9.24)$$

The beam is directed through an variable aperture to a photodiode. The aperture provides a means to control the amount of light entering the photodetector. The photodiode converts the incident power into electrical current. The current is converted by a electronic circuit to a voltage signal and amplified to allow processing. Thus, the signal voltage $V(\theta)$ is proportional to the light intensity integrated over the area of the photodiode. For a single diode of rectangular geometry, this is $$V(\theta) = k \int I(x,y) dx dy \quad (9.25)$$

$$= \frac{kI_0}{\pi a^2} \int_{x_1}^{x_2} \int_{y_1}^{y_2} e^{-(x/a)^2} e^{-(y/a)^2} dx dy$$

$$= \frac{kI_0}{4} [\text{erf}(x_1/a) - \text{erf}(x_2/a)][\text{erf}(y_1/a) - \text{erf}(y_2/a)]$$

where k represents the sensitivity of the photodetector, and $x_{1,2}$ and $y_{1,2}$ are the rectangular boundaries of the photodetector aperture. A diagram of the intensity distribution and the corresponding aperture for single-element detection (SEP) is shown in FIG. 51. A change in the position of the laser beam is equivalent to a change in the position of the photodiode. The beam deflection enters Equation 9.25 as $$V(\theta) = \quad (9.26)$$

$$\frac{kI_0}{4}\left[\text{erf}\left(\frac{x_1+z_0\theta}{a}\right) - \text{erf}\left(\frac{x_2+z_0\theta}{a}\right)\right]\left[\text{erf}\left(\frac{y_1+z_0\theta}{a}\right) - \text{erf}\left(\frac{y_2+z_0\theta}{a}\right)\right]$$

where $z_0\theta$ is the change in the transverse position of the laser beam on the photodiode. For deflection in the x-direction, the y dependence is constant, and can be absorbed into the constant k. The error function has the expansion $$\text{erf}(x) = \frac{2}{\sqrt{\pi}}\left[x - \frac{x^3}{3} + \frac{x^5}{10} - \ldots\right]. \quad (9.27)$$

Expansion of Equation 9.26 and approximation to first order results in $$V(\theta) \approx \frac{kI_0}{2\sqrt{\pi}}\left[\frac{x_1 - x_2}{a} + \frac{x_1^3 - x_2^3}{3a^3} + z_0\theta x_1^2 - \frac{x_2^2}{a^3}\right]. \quad (9.28)$$

Equation 9.28 contains the essential characteristics of single-element photodetection. The signal is composed of a constant dc voltage and the beam deflection signal. The best results are obtained when the photodetector is positioned such that only one slope of the Gaussian-shaped intensity distribution falls on the photodiode. As the beam deflects, the distribution of intensity on the diode changes resulting in a proportional voltage change. A high-pass filter can be used to remove the dc signal before amplification.

The above calculation may not suffice if the light incident on the photodiode is limited by the circular aperture. Consider a Gaussian beam incident on a circular region in the xy-plane. Let the beam intensity be proportional to $e^{-(r/a)^2}/(\pi a^2)$. This is normalized to unity. Let the circle have a radius b and an origin at $(x_0, 0)$. The fraction of the laser intensity incident on the circle is $$F(x_0, b) = \frac{1}{\pi a^2} \int_0^b \rho d\rho \int_0^{2\pi} e^{-(r/a)^2} d\phi, \quad (9.29)$$

where $(\rho, \Phi)$ are polar coordinates with an origin at the center of the circle. The coordinate r can be expressed as $$r^2 = \rho^2 + x_0^2 - 2\rho x_0 \cos\phi. \qquad (9.30)$$

Thus $$F(x_0, b) = \frac{2}{\pi a^2} e^{-(x_0/a)^2} \int_0^b \rho d\rho e^{-(\rho/a)^2} \int_0^\pi e^{-(x_0/a)(\rho/a)\cos\phi} d\phi. \qquad (9.31)$$

This simplifies further through the definition of the modified Bessel function [70]

$$I_0(\alpha) = \frac{1}{\pi} \int_0^\pi e^{\alpha \cos x} dx, \qquad (9.32)$$

and the substitution u=p/a:

$$F(x_0, b) = 2e^{-(x_0/a)^2} \int_0^{(b/a)} e^{-u^2} I_0(ux_0/a) u du. \qquad (9.33)$$

The modified Bessel function can be expressed as an ascending series [70]

$$I_0(\alpha) = \sum_{k=0}^\infty \frac{(\alpha/2)^{2k}}{k!k!}. \qquad (9.34)$$

Thus $$F(x_0, b) = 2e^{-(x_0/a)^2} \sum_{k=0}^\infty \frac{(x_0/a)^{2k}}{k!k!} \int_0^{(b/a)} e^{-u^2} u^{2k+1} du \qquad (9.35)$$

$$= e^{-(x_0/a)^2} \sum_{k=0}^\infty \frac{(x_0/a)^{2k}}{k!k!} G_k(b/a),$$

where $$G_k = \int_0^{(b/a)^2} e^{-v} v^k dv. \qquad (9.36)$$

These can be evaluated by integration by parts to obtain $$G_k = kG_{k-1} - (b/a)^{2k} e^{-(b/a)^2}; \quad G_0 = 1 - e^{-(b/a)^2} \qquad (9.37)$$

Some typical results are shown in FIG. 52. Movement of the detector along the x-axis maps out the Gaussian distribution of the laser spot. The beam deflected signal is calculated by substituting $x_0+z\theta$ for $x_0$.

An alternative detector has been developed to take advantage of the entire beam profile. This design uses a quad-element photodiode configured as a dual-element photodetector (DEP) to form a position-sensitive detector [63]. For example, a beam deflection to the right would cause an increase in the voltage from the right element $V_+(\theta)$ and a decrease in the voltage from the left $V_-(\theta)$. Upon subtraction, $$V(\theta) = V_+(\theta) - V_-(\theta), \qquad (9.38)$$

DEP provides twice the signal of each element separately. The corresponding aperture coordinates are shown in FIG. 51 From Equation 9.28, $$V_+(\theta) \approx \frac{kI_0}{2\sqrt{\pi}} \left[ \frac{x_0 - x_1}{a} + \frac{x_0^3 - x_1^3}{3a^3} + z_0\theta x_0^2 - \frac{x_1^2}{a^3} \right] \qquad (9.39)$$

and $$V_-(\theta) \approx \frac{kI_0}{2\sqrt{\pi}} \left[ \frac{x_1 - x_2}{a} + \frac{x_1^3 - x_2^3}{3a^3} + z_0\theta x_1^2 - \frac{x_2^2}{a^3} \right] \qquad (9.40)$$

where $x_1$ is the distance from the center of the diode to the center of the intensity distribution. Substitution into Equation 9.38 results in $$V(\theta) = \frac{kI_0}{2\sqrt{\pi}} \left[ \frac{x_0 + x_2}{a} + \frac{x_0^3 + x_2^3}{3a^3} + z_0\theta \frac{x_0^2 + x_2^2}{a^3} \right]. \qquad (9.41)$$

If the photodetector is centered on the beam, i.e. $x_0 = -x_2$, then $$V(\theta) = \frac{kI_0 x_0^2 z_0 \theta}{a^3 \sqrt{\pi}} \qquad (9.42)$$

$$= \frac{k' I_0 z_0 \theta}{a^3}$$

where k' is a combined constant reflecting the sensitivity of the photodetector.

Comparing Equation 9.42 with Equation 9.28, DEP has at least twice the sensitivity than SEP. However, in practice, SEP has been found to be less sensitive to environmental vibrations, and may be more appropriate in certain industrial applications. In each case, the detectors can be placed on a servo mechanism to expedite initial alignments using their respective dc voltages.

Substitution of Equation 9.21 into Equation 9.42 yields $$V(\theta) = \frac{-k' I_0 z_0}{n_0 v a^3} \int \frac{\partial n_a(r - vt)}{\partial t} dz. \qquad (9.43)$$

By connecting the results of Equation 9.43 and Sections 9.3.1 and 9.3.2, the resulting photodetected signal is found to be proportional to the first time derivative of the solid surface displacement. In this vein, the acoustic signal will resemble one achieved by CFP-based detection.

9.3.5 Dependence on Propagation Angle

The sensitivity of the system to the direction of propagation of the airborne waveform can be examined theoretically. Consider a plane wave traveling at an angle $\Phi$ with respect to the probe beam. The wave extends in the z-direction from $-b$ to $b$. The index of refraction is $$n(r) = n_0 + n_a e^{i(k \cdot r - \omega t)} \qquad (9.44)$$

$$= n_0 + n_a e^{i(kr\cos\Phi - \omega t)}.$$

Substitution into Equation 9.19 yields $$\theta = \frac{ikn_a}{n_0} \int_{-b}^{+b} e^{i(kr\cos\Phi - \omega t)} \cos\Phi dz \qquad (9.45)$$

$$= \frac{2bikn_a}{n_0} e^{i(kr\cos\Phi - \omega t)} \cos\Phi.$$

The resulting signal is a phase-shifted replica of the original acoustic wave, decreasing by a factor $\cos\Phi$ as $\Phi$

Chapter 10

EXPERIMENTAL VERIFICATION OF GCLAD

One advantage of using GCLAD over interferometric techniques is the simplicity and versatility in the experimental setup. In its simplest form, shown in FIG. 53, the pulsed Nd:YAG laser generates the wave into the material to be tested.

The cw Nd:YAG laser is directed parallel to the test sample. A fast photodetector is positioned to accept the beam. A Panametrics [71] 1 MHz piezoelectric transducer is also positioned along the beam path for alignment and optimization purposes. The following chapter details experiments performed to verify that the detected signal was indeed a result of beam deflection by an acoustic wave.

10.1 Verification of the Air as the Transport Medium

An experiment was designed to verify that the transport medium between the sound source and the laser beam was air. A contact piezoelectric transducer was mounted on a carbon/epoxy composite to serve as the sound source. It was placed near the detection laser beam such that the wave traveled from the transducer, into the composite, into the air, and then passed through the laser beam. A sample wave is shown in FIG. 54.

The distance between sample and laser beam was varied from 1 mm to 30 mm, while the time of flight was recorded, and plotted as shown in FIG. 55.

A linear regression fit reveals a slope of 350±3 m/s ($R^2$=0.998) which agrees with the speed of sound in air. Calculation of the intercept provides the composite's sound velocity of 3.6 mm/$\mu$s.

A similar experiment was performed in an enclosed environment. A transparent plastic bad, equipped with ports for the probe beam, was placed over the testing region. Helium was pumped into the enclosed environment with the intention of increasing sound velocity. The ultrasonic waves launched into the air/helium mixture were found to have a significantly higher velocity, 420 m/s, than the waves detected in air alone. These tests provided convincing evidence that the detected acoustic waves are transported by a gas medium.

10.2 Attenuation of Ultrasonic Wave Amplitude in Air

The attenuation of the ultrasonic wave in air was measured. Using the same setup described above, the amplitude of the wave was measured as a function of distance. The results are shown in FIG. 56.

On important feature of this graph is that sizable acoustic waves can still be detected beyond 2 inches even though the frequencies involved are in the megahertz range. The attenuation coefficient $\alpha$ was calculated by assuming that the signal amplitude decayed according to the one-dimensional Equation $$A = A_0 e^{-\alpha r} \qquad (10.1)$$

where r is the distance from source to laser beam, and A is the signal amplitude. The regression fit yielded $\alpha$=0.0182±0.0003 mm$^{-1}$ with a $R^2$ value of 0.990. According to Equation 9.2, the attenuation coefficient is 0.02 mm$^{-1}$ for a frequency of 1 MHz. This agrees well with technique used above.

10.3 Dependence on Detection Beam Width

A series of experiments was performed to investigate the system dependence on the width of the probe laser beam. A combination of convex and concave lenses provided the means to expand and decrease the width of the beam, from the original 0.7 mm diameter, at the point of deflection. Larger beam widths tended to wash out the signal, particularly when using the single-element photodetector. The reasoning is that an airborne acoustic pulse has a wavelength on the order of 0.35 mm at 1 MHz. This pulse takes about 2 $\mu$s to traverse the original beam. A detector with a small aperture can record the wave at different points inside the laser beam. If the aperture size is increased, the different "phases" of the waveform as it travels across the beam tend to cancel themselves out. Use of a larger beam width increases this effect. The optimum condition exists when the beam width is smaller than the wave length of the acoustic pulse.

Unfortunately, decreasing the beam width near the deflection point also decreases the amount of interaction between the acoustic wave and laser beam. This can be compensated for by using a cylindrical lens to focus the beam. The lens is aligned such that the acoustic travel time through the beam is limited, but the amount of interaction is not adversely affected.

FIG. 57 shows two GCLAD signals, one which uses a convex spherical lens to narrow the beam width, and another which uses a cylindrical lens. In this case, the signal-to-noise ratio has almost doubled.

10.4 Sensitivity to the Distribution of Sound Field

One possible disadvantage GCLAD has to typical laser ultrasonics, as demonstrated by Equation 9.21, is that the beam integrates over the width of the acoustic disturbance. This reduces the spatial resolution on the axis of the laser beam. If the sound wave diverges significantly in air, any search for small defects would fail.

To test the sensitivity of the detection system on non-direct waveforms, a sound baffle with a 0.2 cm wide slit was placed between the beam and sound source. A 1 MHz transducer, placed 2.45 cm from the beam, transmitted an acoustic pulse through the slit and into the path of the beam. The baffle was positioned 6.5 mm from the beam and translated parallel to the beam in attempt to map out the acoustic field. The amplitudes of the waveforms were then recorded as a function of the baffle position. The experiment was repeated twice, with the transducer placed at 3.29 and 3.92 cm from the laser beam.

The results, shown in FIG. 58, show the detected pattern does not spread appreciably as the transducer is moved further away from the beam. The 2 cm window, where significant signal is obtainable, is roughly the same dimension of the transducer used to generate the wave. The dependence of the system on the angle of waveform propagation was examined theoretically in Section 9.3.5. Qualitative experiments, where the angle the acoustic source was decreased with respect to the probe beam, have exhibited a steady decline of signal.

10.5 Variation of Ultrasonic Amplitude with Laser Intensity

Next, the dependence of the detection system on the laser intensity was tested. A setup, shown in FIG. 59, was configured where the laser beam passes through a half-wave plate, and is redirected by a polarizing beam splitter (PBS).[1] Rotating the wave plate varies the polarization of the beam from vertical to horizontal polarization. The PBS reflects the vertical component pass the sound source and to the detector. Preliminary tests have shown the signal is independent of the laser polarization.[2] Hence, as the polarization is varied, the intensity of light changes. The intensity of the laser beam was recorded by measuring the dc level of the SEP signal.

[1] The PBS transmits horizontally polarized light and redirects vertically polarized light.
[2] These tests replaced the PBS with a plane mirror in the setup, varied the polarization, but kept the intensity constant. This had no affect on the signal.

The acoustic wave amplitude, as shown in FIG. 60, was found to be directly proportional to the incident intensity as Equation 9.28 predicts. The slope of the line, 10.82 mvolts/volt ($R^2$=0.998), provides a measure of the sensitivity of the photodetector.

10.6 Verification of Beam Deflection

If the detected signal is the result of the beam being deflected by the sound wave, then the amplitude of the signal will increase with the distance $z_o$ (see FIG. 53) between the beam deflection point and the single-element photodetector, as Equation 9.28 predicts. With the laser beam carefully aligned, the position of the acoustic source, a piezoelectric transducer, was varied along the length of the beam, while the perpendicular distance from source to beam was held constant. The amplitudes of the sound waves were recorded as a function of distance and are displayed in FIG. 61.

For each run, the transducer was placed on a different side of the laser beam, to insure the results are not due to a variation in the perpendicular distance. Both runs demonstrate that the signal amplitude increases with increasing separation. This provides empirical evidence that beam deflection is indeed the mechanism which causes the change in incident intensity on the photodiode.

The non-zero y-intercept in FIG. 61 is not in total agreement with the theoretical prediction. The theory does not account for the divergence of the probe beam.[3] A larger beam width at the point of detection can result in either an improved signal or a more complicated signal (see Section 10.3). As the transducer is positioned closer to the detector, the signal does approach zero amplitude, but not in a linear fashion. A preferred approach to this experiment would keep the laser to acoustic source distance constant while the photodetector is moved.

[3] the experiment was repeated without lenses to eliminate their influence. The dependence was similar.

A second experiment was devised to measure the actual deflection angle caused by the sound wave. The single-element photodetector was mounted on a translation table providing movement transversely to the beam axis. A stationary piezoelectric transducer served as the sound source. Once aligned, the table was moved in 0.00625" increments while measurements of peak-to-peak amplitudes and dc level of the detector were taken.

As shown in FIG. 62, the dc level follows the Gaussian intensity distribution of the laser beam, while the signal amplitude reflects the first derivative of the intensity distribution. This suggests that the detected signal is indeed a result of the slight deflections of the beam from the original position on the photodiode.

To verify this, the integration of a Gaussian beam intensity over a circular aperture, derived in Section 9.3.4, can be applied. By introducing a beam width of α=0.04 inches and aperture radius of b=0.01 inches into Equation 9.35, the calculation follows the contour of the empirical data well, as shown in FIG. 63.

Taking the first derivative of Equation 9.35 yields $$\frac{\partial F(x_0, b)}{\partial x_0} = 2e^{-(x_0/a)^2} \sum_{k=0}^{\infty} \frac{(x_0/a)^{2k}}{k!k!} G_k(b/a)\left(2k\frac{a}{x_0} - \frac{x_0}{a}\right). \quad (10.2)$$

This equation is also plotted in FIG. 63. Although the derivative is adequate beyond ±0.04 inches, it is insufficient near the center. One possible remedy is to replace each data point with an average of the points around it. This was applied using an average of twelve points, and the calculation is more consistent with the empirical data.

If the signal is indeed a result of the change in slope, than the signal should undergo a polarity change as the detector is moved from one side of the beam to the other. FIG. 64 shows that this is the case.

10.7 Calculation of the Angle of Deflection

The change in beam deflection angle θ was computed for the SEP using data from FIG. 64 by first assuming a linear region between any two measurements. Then the fraction of signal change is set equal to the fraction of beam change $$\frac{\text{Signal Amplitude}}{\text{incremental change in dc voltage}} = \quad (10.3)$$

$$\frac{\text{beam deflection angle}}{\text{incremental change in detection angle}}.$$

This approximates to $$\Theta = \frac{\Delta\theta_0}{V_i - V_{i-1}} \frac{A_i + A_{i+1}}{2} \quad (10.4)$$

where $\Delta\theta_o$ is the angle between increments, $V_i - V_{i-1}$ is the dc voltage difference between successive increments, and ½($A_i + A_{i+1}$) is the average signal amplitude between successive measurements. The beam deflection angle was found to be around $2 \times 10^{-5}$ degrees. This translates into about 0.7 μm maximum deflection for a 2 m $z_o$ distance. However, based on the strength of the signals taken here, deflections an order of magnitude smaller are detectable.

A similar approached was used for the dual-element detector (DEP). The dc voltage level of the DEP was measured as function of the transverse position.

As shown in FIG. 65, for a narrow region, the voltage is proportional to the transverse position of the detector. The slope of the line provides the calibration of the detection system. The beam deflection angle can be calculated from $$\theta = \text{SignalAmp} \times \text{slope}\left(\frac{\text{inches}}{\text{volt}}\right) \times \frac{360}{2\pi z_0} \text{degrees/volt}, \quad (10.5)$$

which in this case $$\theta = \text{SignalAmp} \times 1.024 \times 10^{-2} \text{ degrees/volt} \quad (10.6)$$

for a slope of $8.604 \times 10^{-3}$ inches/volt and $z_o$=48.0 inches. A transducer generated waveform, calibrated by the above method, is shown in FIG. 67.

Chapter 11

ULTRASONIC APPLICATIONS OF GCLAD

Application of GCLAD to the field of ultrasonics has many advantages over interferometric techniques. Since the test sample does not become a part of the detection system, alignment of the sample with this system is not as crucial. Samples can be substituted with ease. Examples of laser generated/GCLAD detected waveforms are shown in Section 11.1. This concept also holds for performing C-scans on composite panels. Examples are shown in Section 11.2 Section 11.3 discusses alternative configurations.

11.1 Laser Generated/GCLAD Detected Waveforms

In interferometric detection techniques, the test sample serves as one mirror of the interometer. With GCLAD, alignment of the system is independent of the sample. Hence, materials can be substituted into the setup quite easily. To demonstrate, laser generated/GCLAD detected ultrasonic waveforms were taken in a variety of polymer/graphite composites, shown in FIG. 67.

Included on the graph are a 3.0 mm thick graphite/PEEK pultruded rod, the 2.9 mm thick graphite/PEEK composite used in Chapter 6, and a 1.5 mm thick graphite/PEEK tow-placed panel (AS-4/PEKK, $[0/90]_{2S}$). The generating spot size was 0.8 cm². A 40 gain amplifier was employed and the resulting waveforms were digitally averaged over 25 shots. The distance from sample to beam was about 5 mm. The delay times are attributed to small variations in this distance. The generating spot size was 0.8 cm². The graph exhibits many longitudinal wave echoes, the transverse wave, and mode conversion of the transverse wave to a longitudinal wave. Also apparent is the attenuation of higher frequencies that was discussed in Section 6.4. GCLAD detected waves in 6.0 mm thick PEEK and 9.0 mm thick PVC are displayed in FIG. 68.

11.2 GCLAD C-scans of Composite Materials

FIG. 69 shows a C-scan of the 8.9 mm graphite/epoxy composite with an embedded Teflon flaw shown previously in FIG. 45. The C-scan was performed using the apparatus described in Section 8.1 and air-coupled detection. The intensity of the generating laser was adjusted to be slightly below the ablation threshold. The detection beam was positioned about 4 mm from the sample, and followed a 6 m path, folded with mirrors, to the photodetector. Each pixel is the average of eight waveforms. The scan exhibits drastic contrast between flawed and unflawed regions. Of particular importance is the resolution of the edge of the flaw. This gives an indication of the size of the defect that can be detected. Here, the edge never appears to be more than two pixels, or 2 mm thick. This is consistent with detection using 1.5 MHz frequencies.

FIG. 70 shows a C-scan performed on one section of the tow-placed panel (AS-4/PEKK, $[0/90]_{2S}$) first shown in FIG. 46. The area scanned was 25×25 mm with 625 total points taken. As before the light areas show good ultrasonic reception. In this case, the laser beam was not centered on the photodiode, resembling a single-element diode. As discussed in Section 9.3, this helps to provide a more consistent scan.

11.3 Compact Configuration

One possible drawback to beam deflection detection is $z_o$ should be significant in order to obtain a reasonable signal. This distance will depend on laser quality, sound amplitude and detector sensitivity. There is, however, a decided advantage in keeping $z_o$ the same, and reducing the size of the system. A series of mirrors placed after the sound source can accomplish this. Another possibility is arranging two plane rectangular mirrors such that they face each other. Directing the beam at a slight angle to their axis will result in multiple reflections of each. Each reflection yields another increase in signal, proportional to the separation distance.

Another possibility is to pass the laser beam in front of the sound source several times before it is sent to the photodetector. As long as the beam is deflected in the same direction, each pass with increase the signal an amount proportional to the beam deflection angle.

For example, a loop configuration is shown in FIG. 71. The setup uses three standard mirrors, and one partially reflecting mirror with reflectivity R. Laser light enters the loop through the partially reflecting mirror, as shown. The mirrors are aligned such that the beam follows the same path, with a small amount of light transmitted to the photodetector, for each round trip.

For a typical setup using the DEP detector, Equation 9.42 can be represented by $$S_o(\theta) = C_o I_o \theta \quad (11.1)$$

where C describes the characteristics of the photodetector. Equation 11.1 represents the strength of the signal. For the compact setup, $S(\theta)$ will be the sum of each trip around the loop, taking into account the reflectivity of the output mirror. Therefore $$\begin{aligned} S_c(\theta) &= C\theta I_0\left(a+\frac{3}{2}b+c\right)(1-R)+C\theta I_1(1-R)[2(a+b)+ \\ &\quad \left(a+\frac{3}{2}b+c\right)]+C\theta I_2(1-R)\left[4(a+b)+\left(a+\frac{3}{2}b+c\right)\right]+\ldots \\ &= C\theta I_o(1-R)\left[\left(a+\frac{3}{2}b+c\right)+R\left[2(a+b)+\left(a+\frac{3}{2}b+c\right)\right]+ \right. \\ &\quad \left. R^2\left[4(a+b)+\left(a+\frac{3}{2}b+c\right)\right]+\ldots\right] \\ &= C\theta I_o(1-R)\left[\left(a+\frac{3}{2}b+c\right)\sum_{i=0}^{\infty}R^i+2(a+b)\sum_{i=0}^{\infty}iR^i\right] \\ &= C\theta I_o\left[\frac{a+\frac{3}{2}b+c}{1-R}+\frac{2R(a+b)}{(1-R)^2}\right] \\ &= C\theta I_o\left[l_1+\frac{2Rl_2}{1-R}\right] \end{aligned} \quad (11.2)$$

where $$l_1 \equiv a+\frac{3}{2}b+c \quad (11.3)$$

$$l_2 \equiv a+b.$$

The dependence of Equation 11.2 is easily seen if $$c \equiv a+\frac{1}{2}b. \quad (11.4)$$

Equation 11.2 becomes $$S_c(\theta) = \frac{C\theta I_o l_1}{1-R}. \quad (11.5)$$

The signal amplitude grows rapidly as R approaches one. The advantage over the basic configuration is seen by letting $z_o = l_1$, and dividing Equation 11.1 by Equation 11.5. The result is $$\frac{S_c}{S_o} = \frac{1}{1-R}. \tag{11.6}$$

A reflectivity of 0.95 yields in a gain of 20 in signal amplitude for similar sized configurations.

11.4 Gas-coupled Laser Acoustic Generation

There exists the possibility of generating the the ultrasonic pulse in the material without striking the sample with the laser pulse. The laser beam can be directed at an alternative sample located close to the sample. With the right configuration the shock wave created by ablating the dummy sample, would strike the test sample [34].

In a second scheme [72], the laser beam is directed parallel to the surface of the sample. A convex lens would focus the beam to a point at the desired generation site. At this point, the air would be ionized, sending a shock wave towards the sample. As before, shock wave creates the ultrasonic wave in the sample. The beam is then directed to a suitable beam dump.

Chapter 12

GCLAD IN THE AUDIBLE FREQUENCY RANGE

The lack of a frequency dependence of GCLAD led to its application in the audible frequencies. A dual-element photodetector was built specifically to achieve this purpose. Two applications have since developed. The first, realized in Section 12.1.1, involves measuring the frequency response in an enclosed cavity. An acoustic sine wave generated by a speaker is launched into the cavity. The laser beam is directed through ports across the center of the cavity. The waves deflect the probe beam proportionally. Since light is massless, the laser beam does not impede the travel of the sound waves. Then the signal amplitude is measured as the frequency of the sine waves is changed. Signal amplitude data is calibrated for beam deflection angle. A plot of the deflection angle with frequency reveals the frequency response of the cavity.

In the second application, the photodetector is connected through an amplifier system to an input of a portable stereo. In this scenario, the system operates as a common recording microphone. Recorded sounds are easily heard upon playback of the tape cassette. Several sounds, recorded digitally, are shown in Section 12.2.

12.1 Audible Frequency Response of a Cavity

12.1.1 Measurement of the Frequency Response

To facilitate the first application, ports for a research speaker, a conventional microphone, and the laser probe beam, were drilled in an aluminum cylindrical cavity with interior dimensions shown in FIG. 72. A Hewlett-Packard function generator (model 3325A) drove the University Sound UD-12 speaker coupled to the cavity. The probe beam was directed through the center of the cavity, as shown, and a dual-element photodetector, built specifically for audible frequency range, was positioned about 6 meters down the beam path. The photodetector is connected through a high-pass filter to the oscilloscope. A conventional microphone was inserted on the opposite side of the speaker, flush with the wall of the cavity. A Labview program controlled the frequency sweep and the data acquisition.

As the frequency was increased from 2 to 5 kHz, GCLAD and microphone amplitudes were recorded concurrently. The results are shown in FIG. 73. The GCLAD amplitudes have been calibrated[1] for the beam deflection angle according to the procedure outlined in Section 10.7. The microphone signal amplitudes were calibrated for pressure with a B&K microphone calibrator[74]. The detected angles are consistent with the pressures measured by the microphone in this frequency range. The graph exhibits major resonant peaks at about 2.2 and 4.3 kHz. However, diverse results are obtained at higher frequencies, as shown in FIG. 74.

[1] The audible frequency DEP provided a sensitivity of 14.2 volts per millimeter.

The advantage of the laser probe is, unlike the microphone, the light introduces no change in the acoustics of the cavity by its presence.

FIG. 73 provides a calibration from beam deflection angle to sound wave pressure in this frequency range. A beam deflection of $0.43 \times 10^{-3}$ degrees results from a 720 Pascal change in pressure. This can be confirmed by considering the cavity pressure at the 4.3 kHz resonance (see Section 12.1.2)

$$p = p_0 + p_1 \sin\frac{\pi \zeta}{L} \tag{12.1}$$

where L=40 mm is the length of the cavity, $p_o \approx 10^5$ Pa is the atmospheric pressure, and $p_1$=720 Pa is the maximum acoustic pressure. The coordinate axis, shown in FIG. 72, is chosen such that $\hat{\zeta}$ corresponds to the cylindrical axis of the cavity, and $\hat{z}'$ to the undeflected laser beam. The gradient of the pressure in the plane bisection of the cavity ($\zeta$=0), is $$|\nabla p| = \frac{\pi p_1}{L}. \tag{12.2}$$

From Equation 9.11, the corresponding change in the index of refraction is $$\nabla n \approx (n_0 - 1)\frac{\nabla p}{p_0}. \tag{12.3}$$

According to the eikonal equation (Equation 9.13)

$$\frac{\partial^2 r(z')}{\partial z'^2} = \frac{\nabla n(\zeta)}{n(\zeta)} \approx (n_0 - 1)\frac{\nabla p}{p_0}. \tag{12.4}$$

The beam deflection angle can be derived by integrating Equation 12.4 along the z'-axis, or $$\theta = \frac{\partial r(z')}{\partial z'} \approx (n_0 - 1)\int_{-a}^{a} \frac{|\nabla p|}{p_0} dz' \tag{12.5}$$
$$\approx (n_0 - 1)2\pi \frac{ap_1}{p_0 L}$$

where $\alpha$=30 mm is the radius of the cavity. After substitution of the variables into Equation 12.5, $\theta$=$0.57 \times 10^{-3}$ degrees, which is within 20% of the experimental value.

12.1.2 Calculation of the Frequency Response

The discrepancies in frequency response of the two detection methods can be explained by studying the acoustics of the cavity. Consider the acoustic field in a gas-filled cylindrical cavity of radius $\alpha$ and length L. In the limit of vanishing thermal and viscous boundary layers, and at pressures sufficiently low that the walls can be considered rigid, the boundary condition on gas motion is the vanishing of the velocity component normal to the walls. The acoustic pressure under these approximations can be expressed as a series of functions $$\Phi_{lmn\sigma}(r, \phi, z) = J_m(\zeta_{mn}r)\binom{\cos m\phi}{\sin m\phi}\cos(l\pi z/L). \quad (12.6)$$

These functions are expressed in cylindrical coordinates concentric with the axis of symmetry, with the cylinder end walls at z=0 and z=L. The functions $J_m(\zeta)$ are cylindrical Bessel functions. The quantities $\zeta_{mn}$ are the roots of $J'_m(\zeta)=0$, numbered n=0, 1, . . . in order of increasing magnitude. The index σ is 0 for the cos mφ function and 1 for the sin mφ function.

An acoustic source in the center of the wall at z=0 will generate a pressure distribution.

$$p(r, \phi, z) = \sum_{lmn\sigma} \frac{A_{lmn\sigma}\Phi_{lmn\sigma}}{f^2 - (f_{lmn\sigma} + ig_{lmn\sigma})^2}, \quad (12.7)$$

where $A_{lmn\sigma}$ is a coupling coefficient, $g_{lmn\sigma}$ depends on the damping of the sound, and $$f_{lmn\sigma} = c\sqrt{(\zeta_{mn}/a)^2 + (l\pi/L)^2}, \quad (12.8)$$

where c is the speed of sound in the gas. The frequencies $f_{lmn\sigma}$ are the eigenfrequencies of the cylindrical cavity. Note that there are two modes for each eigenfrequency owing to the lack of dependence of the eigenfrequencies on the index σ. The coupling coefficient $A_{lmn\sigma}$ is proportional to the integral of $\Phi_{lmn\sigma}$ over the source. For a circular source on axis this will vanish for m≠0. (Slight geometric imperfections may lead to small, rather than vanishing, values for these coefficients.) A microphone on-axis at the other end of the cylinder will have a response proportional to the integral of $\Phi_{lmn\sigma}$ over the microphone. These factors will also vanish for m≠0. Thus the cavity spectrum observed when the microphone response is measured as a function of source frequency $f$ is expected to have strong peaks at the frequencies $f_{l0n}$.

Consider detection of the sound field by the bending of a light beam passing through the cylinder along a diameter at angle $\phi_0$ and z=L/2. The GCLAD signal is proportional to the gradient of the acoustic pressure integrated over the path length. Hence $$\int (l\pi/L)J_m(\zeta_{mn}r/a)\binom{\cos m\phi_0}{\sin m\phi}\sin(l\pi/2)ds, \quad (12.9)$$

where the integration over the path element ds runs along a full diameter. The integrals are $$-(l\pi/L)\sin(l\pi/2)\int_{-a}^{0} J_m(\zeta_{mn}r/a)\binom{\cos m\phi_0}{\sin m\phi_0}dr \quad (12.10)$$

$$+(l\pi/L)\sin(l\pi/2)\int_{0}^{a} J_m(\zeta_{mn}r/a)\binom{\cos m(\phi_0+\pi)}{\sin m(\phi_0+\pi)}dr$$

-continued $$= [1+(-1)^m]\sin(l\pi/2)\int_0^a J_m(\zeta_{mn}r/a)\binom{\cos m\phi_0}{\sin m\phi_0}dr.$$

This will vanish for even l and odd m.

Table 12.1 lists some values of the roots $\zeta_{mn}$ needed for analysis of the data.

The dimensions of the experimental cavity are α=0.03 m and L=0.04 m. Values of the eigenfrequencies $f_{lmn}$ calculated for these dimensions and a nominal speed of sound (c=345 m/s) are shown in Table 12.2.

From Table 73, a large resonant peak at 4.313 kHz should be detected by both the microphone and GCLAD. A review of FIG. 12.2 shows this is the case. The calculation also predicts a resonance at 7.013 kHz will easily be detected by the microphone, but not by GCLAD. This is confirmed in FIG. 74.

12.2 The Laser Microphone

Using a typical microphone, the pressure wave creates an impulse on a membrane which is connected to an electrical circuit. Thus, sound is converted into a mechanical motion which is than converted into an electrical signal. Since light is massless, there is no mechanical step in GCLAD. Sound is directly converted to an electrical signal. Taking advantage of this difference results in an improved microphone.

Qualitative tests were performed using a variety of sound sources. The resulting signals were then recorded on the digital oscilloscope.

As an example, FIG. 75 shows the result of the syllable "ba" be spoken near the beginning of the laser beam.

FIG. 76 shows a high B-natural (510 Hz) as played on a bassoon in the laboratory. This note, which is in the highest octave of the bassoon's register, was particularly resonant. The laser microphone is affected by air currents, but not substantially more than ordinary microphones. In addition, the laser beam was enclosed by long glass tubes to test the influence of dust particles in the beam path. The insertion of the tubes had no noticeable affect on the noise level of the system, suggesting that the influence is insignificant in laboratory conditions.

Based on the previous success, the photodetector was connected to an electrical circuits, which was connected to the input of a portable stereo. The circuit consisted of several passive filters, and an active integrating circuit, reversing the differentiation occurring as a result of the eikonal relationship. Using various sound sources, the sound was recorded using GCLAD, and onto standard audible tape. Upon playback, the sound quality was comparable to that recorded by the stereo's microphone. A recording of William Osborne's Rhapsody for Bassoon was especially clear.

A background white noise was apparent during these tests. Through the process of elimination, the origin seemed to be the laser itself. Upon further study, the noise appeared to be broadband throughout the audible frequency range. A laser parameter called "short term noise" could explain this. It is an intensity fluctuation which is tested in the 10 Hz to 10 MHz frequency range. According to a Coherent engineer [45], the DPSS-532 laser's short term noise value of <0.25% is comparatively excellent. Since diode-pumped lasers are relatively new, this could explain why this phenomenon has not been seen previously. A comparative study of lasers should resolve this.

TABLE 12.1

Roots $\zeta_{mn}$ of the equation $J'_m(\zeta) = 0$ necessary to compute the eigenfrequencies of a cylindrical cavity.

| m | n | l |
|---|---|---|
| 0 | 0 | 0.00000 |
| 0 | 1 | 3.83171 |
| 0 | 2 | 7.01559 |
| 1 | 0 | 1.84118 |
| 1 | 1 | 5.33144 |
| 1 | 2 | 8.53632 |
| 2 | 0 | 3.05424 |
| 2 | 1 | 6.70613 |
| 2 | 2 | 9.96947 |
| 3 | 1 | 4.20119 |
| 3 | 2 | 8.01524 |
| 3 | 3 | 11.34592 |
| 4 | 1 | 5.31755 |
| 4 | 2 | 9.28240 |
| 4 | 3 | 12.68191 |
| 5 | 1 | 6.41562 |
| 5 | 2 | 10.51986 |
| 5 | 3 | 13.98719 |

TABLE 12.2

Eigenfrequencies calculated with a = 0.03 m and L = 0.04 m, c = 345 m/s. The last columns indicate qualitatively the levels of coupling to the generation source and to the two detection methods.

| | | | | | Detection | |
|---|---|---|---|---|---|---|
| l | m | n | $f_{lmn}$ | Generation | Microphone | GCLAD |
| 0 | 1 | 0 | 3370 | weak | weak | weak |
| 1 | 0 | 0 | 4313 | strong | strong | strong |
| 1 | 1 | 0 | 5473 | weak | weak | weak |
| 0 | 2 | 0 | 5590 | weak | weak | weak |
| 0 | 0 | 1 | 7013 | strong | strong | weak |
| 1 | 2 | 0 | 7060 | weak | weak | strong |
| 0 | 3 | 1 | 7689 | weak | weak | weak |
| 1 | 0 | 1 | 8233 | strong | strong | strong |
| 2 | 0 | 0 | 8625 | strong | strong | weak |
| 1 | 3 | 1 | 8816 | weak | weak | weak |
| 2 | 1 | 0 | 9260 | weak | weak | weak |
| 0 | 4 | 1 | 9733 | weak | weak | weak |
| 0 | 1 | 1 | 9758 | weak | weak | weak |
| 2 | 2 | 0 | 10278 | weak | weak | strong |
| 1 | 4 | 1 | 10645 | weak | weak | strong |
| 1 | 1 | 1 | 10669 | weak | weak | weak |
| 2 | 0 | 1 | 11116 | strong | strong | weak |
| 2 | 3 | 1 | 11555 | weak | weak | weak |
| 0 | 5 | 1 | 11742 | weak | weak | weak |

Chapter 13

COMPARISON OF CFP-BASED DETECTION AND GCLAD

In this chapter, comparisons of the two detection systems will be made in the areas of frequency distribution, simplicity and cost, and working conditions. A comparison at this time, however, may be premature. CFP-based detection has been studied for at least ten years by a variety of groups, as discussed in Chapter 5. Commercial scanning systems are available based on this research [73]. On the other hand, the only intensive research study performed with GCLAD is presented in this work. Consequently, the current status of CFP-based detection will be compared to the promise of GCLAD.

The frequency response of the CFP-based system was discussed in Section 5.4. Under ideal conditions, the system in reflection mode has a flat frequency response from 1 MHz to 75 MHz. In working conditions, frequencies as high as 30 MHz have been obtained for our system. The limitations have been attributed to the photodetector's electronics. For the majority of research presented, this range has been adequate. The frequency response of GCAL is dependent on the frequency response in the gaseous medium. As mentioned in Section 9.2, frequency falls off exponentially with distance. Detection on the order of 10 MHz would take a combination of high amplification and a short distance from source to beam. The line source detection also integrates over the width of the sound wave. This could result in the higher frequency components interfering with each other. Since smaller defects can only be detected at higher frequency ranges, the CFP-based system may be more applicable at these frequencies. However, around 1 MHz, the two systems have shown comparable results when using the same detector/amplifier system on coated surfaces.

In Section 5.5, the CFP-based system was cited as the best interferometric technique when testing materials with optically rough surfaces. The system, however, cannot compete with a system that provides the same results, yet is independent of the surface roughness. Even if the surface reflectivity is good, it will vary from point to point, adversely affecting the results. Fluctuations in the distance from the system to the sample during scanning change how the beam is focused on the sample. This affects the sensitivity and stabilization of the CFP-based system, producing less reliable results. These fluctuations would only affect the GCLAD system by the further attenuation of the sound wave in air. Substitution of test samples also requires realignment for the CFP-based system. This is of no concern for GCLAD. For nondestructive purposes, this is perhaps the main advantage.

The CFP-based system does have an advantage when considering ambient temperature changes. As the temperature in gas changes, so does the speed of the sound travelling through it. The GCLAD waveform would shift in time accordingly. If time-of-flight measurements are required, GCLAD could be performed in a controlled environment. The same measurement can also be taken by measuring the time between the first waveform and its first echo. A third method, where a preferred wavelength waveform is launched into the test sample, has also been suggested. By measuring the frequency of the detected signal, the velocity of sound in the material can be determined. A known sound source could also be introduced to serve as a real time calibration. These methods, however, are usually not necessary with a CFP-based system.

The primary expense in either of the two systems is the purchase of lasers. Compared to this, the cost of the interferometer is a secondary consideration. However, the cost of the etalon, its stabilization system and the accompanying optics are significantly higher than the broadband mirrors which may or may not be included in GCLAD. The four element photodiodes do cost more than the single element diodes,[1] but not enough to compensate. The simplicity of design also saves time in construction, alignment, and operation.

[1] The quad element diodes typically cost around $250, compared to $20 for the single element diodes [48].

Chapter 14

CONCLUSION

In this study, aspects of applying a laser-based ultrasonic inspection system to the evaluation of polymer/graphite composite materials were presented. Specifically these were: the conversion of the confocal Fabry-Perot based detection system to a reflection configuration in order to take advantage of the higher frequency response; the investigation of thermoelastic and ablative generation of ultrasonic waves in composites; and the development of a gas-coupled laser detection system for use in both audible and ultrasonic frequency ranges.

Conversion of the CFP-based system to a reflection configuration resulted from the desire to get a finer resolution in scans than could be obtained in the previous transmission configuration. The frequency response of each made was derived and calculated using empirical parameters in Chapter 5. The reflection mode exhibited the behavior of a high-pass optical filter compared to the band-pass behavior of the transmission mode. An experimental comparison of waveforms detected in each mode confirmed the improved frequency response. With additional implemented improvements in the photodetector/amplifier system, waveforms with rise times as low as 35 ns can now be detected. Better resolution of longitudinal and transverse waves is also observed. Although the system may be simpler to use in transmission mode, the frequency response desired cannot be achieved due to theoretical limitations.

The improved frequency response led to a re-evaluation of the ablative generation effects on the laser-generated ultrasound in composites. The evolution of the ablatic waveform can be witnessed experimentally without post-analysis, as generation progresses from thermoelastic to ablative mode. Improved calibration techniques allowed the correlation of the onset of the ablatic wave and laser ablation. The detection of a transverse wave in the ablation regime, where it had been absent in the thermoelastic regime, provides evidence of a different generation mechanism. A determination of the the generation mechanism of the ablatic waveform was attempted by measuring its directivity pattern and comparing it to the directivity pattern in the thermoelastic regime. This experiment was inconclusive since the higher frequency components necessary to resolve the waveforms attenuated too rapidly. The practice of detecting the light plume produced by ablation was used to verify that the cause of ablation in composites is the absorption of laser light by the graphite fibers. Albation in graphite was found to have significantly longer decay times than the other materials tested. Identification of the graphite fibers as the source material was also confirmed by visual observations of micrographs.

The reliance of the CFP-based detection results on surface reflectivity and optical smoothness of the test sample created the need for a new detection technique. As a result, a system based on airborne sound wave interaction with laser light, designated Gas-coupled Laser Acoustic Detection (GCLAD), was developed. Changes in the air's index of refraction, caused by the compression and rarefaction of the acoustic wave, deflect the laser beam from its original position on a photodiode. The theory, based on the eikonal equation, was derived in Section 9.3. The results show a direct proportionality on laser intensity, beam deflection angle, and the distance from sound source to detector. These were verified empirically in Chapter 10, in addition to measuring the velocity and attenuation of ultrasonic waves in air. Laser-generated waveforms were captured using GCLAD in a variety of materials along with initial C-scans. Possible alternatives to the fundamental set-up were also presented. The system was then compared to the existing CFP-based system. Although CFP-based detection has an advantage in frequency response, this should be compensated by the simplicity and surface-independent qualities of GCLAD.

Bibliography

[1] J. N. Caron, *Methods for Studying Ablation Phenomena using Laser Ultrasonics*, Master's Thesis, University of Delaware, 1995.

[2] W. Sachse, A. G. Every, and I. Grabec, "Quantitative Ultrasonic Measurements in Composite Materials", *Nondestructive Evaluation*, Vol. 10, p. 77, 1991.

[3] B. T. Aström, *Manufacturing of Composite Materials*, (Chapman & Hill:London), 1997.

[4] J. P. Monchalin, "Optical Detection of Ultrasound at a Distance Using a Confocal Fabry-Perot Interferometer," *Applied Physics Letters*, Vol. 47, p. 14, 1985.

[5] V. I. Danilovskaya, *Journal of Applied Mathematics and Mechanics*, Vol. 14, p. 316, 1950.

[6] J. E. Michaels, *Planetary Space Science*, Vol. 7, p. 427, 1960.

[7] R. M. White, "Generation of Elastic Waves by Transient Surface Heating," *Journal of Applied Physics*, Vol. 14, No. 12, p. 3559, 1963.

[8] F. A. McDonald, "On the Calculation of Laser-Generated Ultrasound Pulses", *Journal of Nondestructive Evaluation*, Vol. 9, no. 4, p. 223, 1990.

[9] J. B. Spicer, *Laser Ultrasonics in Finite Structures: Comprehensive Modelling with Supporting Experiment*, Ph.D. Thesis, Johns Hopkins University, 1991.

[10] G. C. Wetsel, "Ultrasonic-Wave Generation by Harmonic Heating in Composite Structures", *Applied Physics Letters*, Vol. 41, p. 511, 1982.

[11] G. C. Wetsel, "Photothermal Generation of Thermoelastic Waves in Composite Media", *IEEE Transactions on Ultrasonics, Ferroelectrics, and Frequency Control*, Vol. UFFC-33, no. 5, p. 450, 1986.

[12] L. P. Scudder, D. A. Hutchins, and J. T. Mottram, "The Ultrasonic Impulse Response of Unidirectional Carbon Fibre Laminates", *Ultrasonics*, Vol. 32, no. 5, p. 347, 1994.

[13] M. Paul, B. Haberer, A. Hoffmann, M. Spies, and W. Arnold, "Determination of the Elastic Behavior of Carbon-reinforced Carbon Materials using Laser-Ultrasound and Theoretical Modeling", preprint.

[14] C. Corbel, F. Guillois, D. Royer, M. A. Fink, and R. R. De Mol, "Laser-Generated Elastic Waves in Carbon-Epoxy Composite", *IEEE Transactions on Ultrasonics, Ferroelectrics, and Frequency Control*, Vol. UFFC-40, no. 6, p. 710, 1993.

[15] M. Dubois, M. Choquet, J. P. Monchalin, F. Enguehard, and L. Betrand, "Absolute Optical Absorption Spectra in Graphite Epoxy by Fourier Transform Infrared Photoacoustic Spectroscopy", *Optical Engineering*, Vol. 32, no. 9, p. 2255, 1993.

[16] B. R. Tittmann, R. S. Linebarger, and R. C. Addison Jr., "Laser-Based Ultrasonics on Gr/Epoxy Composite, " *Journal of Nondestructive Evaluation*, Vol. 9, No. 4, p. 229, 1990.

[17] J. P. Monchalin, J. D. Aussel, P. Bouchard, and R. Heon, "Laser-Ultrasonics for Industrial Applications", *Review of Progress in Quantitative Nondestructive Evaluation*, Vol. 7B, p. 1607, 1988.

[18] H. I. Ringermacher and A. D. W. McKie, "Laser Ultrasonics for the Evaluation of Composites and Coatings", *Materials Evaluation*, Vol. 53, no. 12, p. 1365, 1995.

[19] A. D. W. McKie and R. C. Addison, "Practical Considerations for the Rapid Inspection of Composite Materials using Laser-based Ultrasound", *Ultrasonics*, Vol. 32, no. 5, p. 333, 1994.

[20] J. Krautkrämer and H. Krautkrämer, *Ultrasonic Testing of Materials*, (Springer-Verlag:Berlin), 1990.

[21] C. B. Scruby and L. E. Drain, *Laser Ultrasonics*, (Adam Hilger:Bristol), 1990.

[22] J. N. Caron, Y. Yang, J. B. Mehl, and K. V. Steiner, "Thermoelastic/Ablatic Generated Ultrasound in Graphite/Polymer Composites Detected with a CFP-based System in Reflection Configuraiton", *Review of Progress in Quantitative Nondestructive Evaluation*, Vol. 15, 1996.

[23] R. J. Dewhurst, D. A. Hutchins, and S. B. Palmer, "Quantitative Measurements of Laser-generated Acoustic Waveforms", *Journal of Applied Physics*, Vol. 53, no. 6, p. 4064, 1982.

[24] J. C. Gonthier, M. Dubois, F. Enguehard, and L. Betrand, "Influence of the Pulse Energy Distribution on the Efficiency of Ultrasound Generation by Laser", *Journal De Physique IV*, Vol. 4, p. C7-685, 1994.

[25] J. W. Wagner, J. B. Deaton, J. B. Spicer, and A. D. W. McKie, "Laser Generation of Narrowband and Directed Ultrasound for Noncontact Ultrasound Testing", *IEEE Ultrasonics Symposium Proceedings*, Vol. 2, p. 661, 1990.

[26] J. Yang, N. DeRidder, C. Ume, and J. Jarzynski, "Non-contact Optical Fibre Phased Array Generation of Ultrasound for Non-destructive Evaluation of Materials and Processes", *Ultrasonics*, Vol. 31, no. 6, p. 387, 1993.

[27] M. Noroy, D. Royer, and M. Fink, "The Laser-generated Ultrasonic Phased Array: Analysis and Experiments", *Journal of the Acoustical Society of America*, Vol. 94, no. 4, p. 1934, 1993.

[28] J. S. Steckenrider, T. W. Murray, J. W. Wagner, and J. B. Deaton Jr., "Sensitivity Enhancement in Laser Ultrasonics using a Versatile Laser Array System", *Journal of the Acoustical Society of America*, Vol. 97, no. 1, p. 273, 1995.

[29] R. J. Gutfeld, D. R. Vigliotti, C. S. Ih, and W. R. Scott, "Thermoelastic Hologram for Focused Ultrasound", *Applied Physics Letters*, Vol. 42, no. 12, p. 1018, 1983.

[30] J. W. Wagner, J. B. Deaton Jr., and J. B. Spicer, "Generation of Ultrasound by Repetitively Q-switching a Pulsed Nd:YAG Laser", *Applied Optics*, Vol. 27, no. 22, p. 4696, 1988.

[31] J. C. Miller (Ed.), *Laser Ablation*, (Springer-Verlag:Berlin), 1994.

[32] P. E. Dyer, and R. Srinivasan, "Nanosecond Photoacoustic Studies on Ultra-violet Laser Ablation of Organic Polymers," *Applied Physics Letters*, Vol. 48, no. 10, p. 445, 1986.

[33] D. A. Hutchins, R. J. Dewhurst, and S. B. Palmer, "Directivity Patterns of Laser-Generated Ultrasound in Aluminum," *Journal of the Acoustical Society of America*, Vol. 70, no. 5, p. 1362, 1981.

[34] S. B. Palmer, et al., *Review of Progress in Quantitative Nondestructive Evaluation*, 1996.

[35] L. M. Kukreja, and P. Hess, "Comment on 'Nanosecond Photoacoustic Studies on Ultraviolet Laser Ablation of Organic Polymers'," *Applied Physics Letters*, Vol. 62(2), No. 11, p. 205, 1993.

[36] R. Srinivasan, "Interaction of Laser Radiation with Organic Polymers", p. 107 in reference [31].

[37] X. Chen, J. Mazumder, and A. Purohit, "Optical Emission Diagnostics of Laser-induced Plasma for Diamond-like Film Deposition", *Applied Physics A*, Vol. 52, p. 328, 1991.

[38] G. Hernandez, *Fabry-Perot Interferometers*, (Cambridge: Cambridge University Press), 1986.

[39] M. Hercher, "The Sperical Mirror Fabry-Perot Interferometer", *Applied Optics*, Vol. 7, no. 5, p. 951, 1968.

[40] M. Born and E. Wolf, *Principles of Optics*, (Pergamon Press: London), 1959.

[41] Q. Shan, S. M. Jawad, and R. J.Dewhurst, "An Automatic Stabilization System for a Confocal Fabry-Perot Interferometer used in Detection of Laser-generated Ultrasound", *Ultrasonics*, Vol. 31, no. 2, p. 105, 1993.

[42] R. J. Dewhurst and Q. Shan, "Modelling of Confocal Fabry-Perot Interferometers for the Measurement of Ultrasound", *Measurement Science and Technology*, Vol. 5, no. 6, p. 655.

[43] J. P. Monchalin and R. Heon, "Laser Ultrasonic Generation and Optical Detection with a Confocal Fabry-Perot Interferometer", *Materials Evaluation*, Vol. 44, p. 1231, 1986.

[44] Coherent Laser Group, 5100 Patrick Henry Drive, Santa Clara, Calif. 95054.

[45] Burleigh Instruments, Inc., Burleigh Park, Fishers, N.Y. 14453.

[46] Tektronix, Inc., P.O. Box 500, Beaverton, Oreg., 97077.

[47] R. G. White, and D. C. Emmony, "Active Feedback Stabilisation of a Michelson Interferometer Using a Flexure Element," *Journal of Physics E: Scientific Instruments*, Vol. 18, p. 658, 1985.

[48] E G & G Optoelectronics Canada, 22001 Dumberry Road, Vaudreuil, Quebec, J7V 8P7, Canada.

[49] Continuum, 3150 Central Expressway, Santa Clara, Calif. 95051.

[50] Haffner, S. M., "Feasibility Study of a Laser Ultrasonic System for Nondestructive Evaluation of Composite Structures," Senior Thesis, University of Delaware, CCM Report #95-21, 1995.

[51] K. V. Steiner, K. Krieger, J. B. Mehl, J. N. Caron, and Y. Yang, "Infrared Thermography and Laser-based Ultrasonic Methods for On-line Porosity Sensing during Thermoplastic Composites Fabrication", *Proceedings of the NTIAC Conference*, St. Louis, Mo., Oct. 1, 1996.

[52] K. D. Tackitt, J. W. Gillespie, J. N. Caron, and J. B. Mehl, "High Temperature Measurements of Ultrasonic Wave Speed using a Laser Ultrasonic Technique", preprint.

[53] H. I. Ringermacher, F. A. Reed, and J. R. Strife. "Laser Ultrasonics for Coating Thickness Evaluation at 1200° C.", *Review of Progress in Quantitative Nondestructive Evaluation*", Vol. 12, p. 1356, 1995.

[54] W. M. D. Wright, D. W. Schindel, and D. A. Hutchins, "Studies of Laser-generated Ultrasound using a Micromachined Silicon Electrostatic Transducer in Air", *Journal of the Acoustical Society of America*, Vol. 95, no. 5, p. 2567, 1994.

[55] D. A. Hutchins, W. M. D. Wright, and G. Hayward, "Air-Coupled Piezoelectric Detection of Laser-Generated Ultrasound", *IEEE Transactions on Ultrasonics, Ferroelectrics, and Frequency Control*, Vol. 41, no. 6, p. 796, 1994.

[56] W. Manthey, N. Kroemer, and V. Mágori, "Ultrasonic Transducers and Transducer Arrays for Applications in Air", *Measurement Science Technology*, Vol. 3, p. 249, 1992.

[57] W. Kuhl, G. R. Schodder, and F.-K. Schröder, "Condenser Transmitters and Microphones with Solid Dielectric for Airborne Ultrasonics", *Acoustics*, Vol. 4, p. 519, 1954.

[58] I. Ladabaum, B. T. Khuri-Yakub, and D. Spoliansky, "Micromachined Ultrasonic Transducers (MUTs)", preprint.

[59] D. W. Schindel and D. A. Hutchins, "Through-thickness Characterization of Solids by Wideband Air-coupled Ultrasound", *Ultrasonics,* Vol. 33, no. 1, p. 11, 1995.

[60] R. Hickling and S. P. Marin, "The Use of Ultrasonics for Gauging and Proximity Sensing in Air", *Journal of the Acoustical Society of America,* Vol. 79, no. 4, p. 1151, 1986.

[61] H. Machlab, W. A. McGahan, and J. A. Woollam, "Thermal Diffusivity Measurements by Photothermal Laser Beam Deflection (PTD): Data Analysis using the Levenberg-Marquardt Algorithm", *Thin Solid Films,* Vol. 215, p. 103, 1992.

[62] A. C. Boccara, D. Fournier, and J. Badoz, "Thermo-optical Spectroscopy: Detection by the 'Mirage Effect'", *Applied Physics Letters,* Vol. 36, no. 2, p. 130, 1980.

[63] C. L. Enloe, R. M. Gilgenbach, and J. S. Meachum, "Fast, Sensitive Laser Deflection System Suitable for Transient Plasma Analysis", *Review of Scientific Instruments,* Vol. 59, no. 9, p. 1597, 1987.

[64] J. A. Sell, D. M. Heffelfinger, P. L. G. Ventzek, and R. M. Gilgenbach, "Photoacoustic and Photothermal Beam Deflection as a Probe of Laser Ablation of Materials", *Journal of Applied Physics,* Vol. 69, no. 3, p. 1330, 1991.

[65] A. Mandelis (ed.), *Principles and Perspectives of Photothermal and Photoacoustic Phenomena,* (Elsevier:New York), 1992.

[66] J. Diaci and J. Možina, "Multiple-pass Laser Beam Deflection Probe for Detection of Acoustic and Weak Shock Waves in Fluids", *Review of Scientific Instruments,* Vol. 66, no. 9, p. 4644, 1995.

[67] X. Jia, G. Quentin, and L. Adler, "A Laser Interferometric Method for Small- and Finite-Amplitude Ultrasonic Waves' Detection in Transparent Media", *Review of Progress in Quantitative Nondestructive Evaluation,* Vol. 15A, p. 623, 1996.

[68] H. Kuttruff, *Ultrasonic, Fundamentals and Applications,* (Elsevier Science Publishers LTD:London), 1991.

[69] A. S. Birks, R. E. Green, and P. McIntire (eds.), *Ultrasonic Testing,* (American Society for Nondestructive Testing: Columbus, Ohio), 1991.

[70] G. Arfken, *Mathematical Methods for Physicists,* (Academic Press: San Diego), 9185.

[71] Panametrics, 221 Crescent St., Waltham, Mass., 02154.

[72] C. Edwards, G. S. Taylor, and S. B. Palmer, "Ulstrsonic Generation with a Pulsed TEA $CO_2$ Laser", *Journal of Physics D: Applied Physics,* Vol. 22, p. 1266, 1989.

[73] Ultra-Optec, 27, deLauzon, Boucherville, Quebec, Canada.

[74] A. G. Bell, "On the Production and Reproduction of Sound by Light," *The Journal of American Science,* Vol. 20, no. 118, p. 305, 1880.

What is claimed is:

1. A non-contacting method of detecting and measuring ultrasonic waves in solid materials comprising the following steps:

a) generating an ultrasonic wave in a solid material that is in contact with a gas so as to cause said solid material to generate an acoustic field in said gas;

b) passing a light beam through said gas and said acoustic field and in a direction which will cause said light beam to hit one or more sensors after said light beam has passed through said gas and said acoustic field without said light beam hitting any surface of said solid material, said acoustic field causing a deflection of said light beam as said light beam passes through said gas and said acoustic field; and c) measuring the deflection of said light beam with said one or more sensors.

2. A method of detecting and measuring an acoustic field in a gas comprising the following steps:

a) passing a light beam through a gas that contains an acoustic field and in a direction which will cause said light beam to pass through said acoustic field and hit one or more sensors after said light beam has passed through said gas and said acoustic field, said acoustic field causing a deflection of said light beam as said light beam passes through said gas and said acoustic field; and b) measuring the deflection of said light beam with said one or more sensors.

3. The method of claim 1, wherein said light beam is a laser beam.

4. The method of claim 1, wherein said one or more sensors comprise at least one photodetector.

5. The method of claim 1, wherein said ultrasonic wave in said solid material is generated by vibrating said solid material.

6. The method of claim 1, wherein said ultrasonic wave in said solid material is generated by hitting a surface of said solid material with a laser beam.

7. The method of claim 1, wherein said ultrasonic wave in said solid material is generated by an acoustic transducer.

8. The method of claim 5, wherein said ultrasonic wave in said solid material is generated by vibrating said solid material with a device which physically contacts at least one surface of said solid material.

9. The method claim 2, wherein said light beam is a laser beam.

10. The method of claim 2, wherein said one or more sensors comprise at least one photodetector.

11. A system for detecting and measuring acoustic fields in a gaseous medium comprising:

a) a light beam source which is capable of producing a light beam which passes through said gaseous medium;

b) one or more sensors capable of sensing said light beam and producing one or more electronic signals upon sensing that said light beam has hit said one or more sensors;

c) one or more devices which:
i) receive the one or more electronic signals from said one or more sensors and determine if said light beam has been deflected from a first position to one or more additional or different positions, and
ii) if said light beam has been so deflected, measure the extent of the deflection of said light beam.

12. The system of claim 11, wherein the system also includes a container which contains said gaseous medium, said container having a port through which said light beam enters the gaseous medium contained within said container.

13. The system of claim 12, wherein said one or more sensors are located inside of said container and in contact with said gaseous medium.

* * * * *

UNITED STATES PATENT AND TRADEMARK OFFICE
CERTIFICATE OF CORRECTION

PATENT NO. : 6,041,020
DATED : March 21, 2000
INVENTOR(S) : Caron et al.

It is certified that error appears in the above-identified patent and that said Letters Patent is hereby corrected as shown below:

<u>Title Page, Abstract,</u>

Line 12, just prior to the beginning of "2)", the following sentences should be inserted:

-- With improvements in photodetector design, rise times of the first longitudinal waves as low as 35 ns can be detected. This also permits improved resolution of waveforms created by concurrent but distinct generation processes. Theory and application of the CFP-based system is discussed. --

Line 19, just prior to the beginning of "3)", the following sentences should be inserted:

-- The evolution of waveforms as a function of laser intensity, identification of graphite fibers as the ablation source material, and surface damage on composites created by the laser light impact are discussed. --

Line 25, at the end, the following sentences should be inserted:

-- Theory and experimental verification are provided. Applications in both the ultrasonic and audible frequency ranges are discussed and demonstrated. --

Signed and Sealed this

Seventh Day of August, 2001

*Attest:*

*Attesting Officer*

NICHOLAS P. GODICI
*Acting Director of the United States Patent and Trademark Office*